US012781195B2

(12) United States Patent
Porteus et al.

(10) Patent No.: US 12,781,195 B2
(45) Date of Patent: Nov. 3, 2026

(54) ORTHOGONAL SAFETY SWITCHES TO ELIMINATE GENETICALLY ENGINEERED CELLS

(71) Applicant: The Board of Trustees of the Leland Stanford Junior University, Stanford, CA (US)

(72) Inventors: Matthew H. Porteus, Stanford, CA (US); Michael K. Cromer, Stanford, CA (US); Renata Martin, Stanford, CA (US); Jonas Fowler, Stanford, CA (US); Kyle Loh, Stanford, CA (US)

(73) Assignee: The Board of Trustees of the Leland Stanford Junior University

( * ) Notice: Subject to any disclaimer, the term of this patent is extended or adjusted under 35 U.S.C. 154(b) by 645 days.

(21) Appl. No.: 17/904,075

(22) PCT Filed: Feb. 19, 2021

(86) PCT No.: PCT/US2021/018882

§ 371 (c)(1),
(2) Date: Aug. 11, 2022

(87) PCT Pub. No.: WO2021/173449

PCT Pub. Date: Sep. 2, 2021

(65) Prior Publication Data

US 2023/0085945 A1 Mar. 23, 2023

Related U.S. Application Data

(60) Provisional application No. 62/981,191, filed on Feb. 25, 2020.

(51) Int. Cl.

| | |
|---|---|
| ***A61K 48/00*** | (2006.01) |
| ***A61K 35/545*** | (2015.01) |
| ***C07K 7/08*** | (2006.01) |
| ***C12N 5/074*** | (2010.01) |
| ***C12N 9/12*** | (2006.01) |
| ***C12N 9/64*** | (2006.01) |
| ***C12N 15/63*** | (2006.01) |
| ***C12N 15/86*** | (2006.01) |
| ***C12N 15/90*** | (2006.01) |

(52) U.S. Cl.

CPC .............. *C12N 5/0696* (2013.01); *C07K 7/08* (2013.01); *C12N 9/1211* (2013.01); *C12N 9/6472* (2013.01); *C12N 15/635* (2013.01); *C12N 15/86* (2013.01); *C12N 15/907* (2013.01); *C12Y 304/22062* (2013.01); *C07K 2319/00* (2013.01); *C12N 2750/14143* (2013.01)

(58) Field of Classification Search

None

See application file for complete search history.

(56) References Cited

FOREIGN PATENT DOCUMENTS

| | | | |
|---|---|---|---|
| WO | WO2017079673 | 5/2017 | |
| WO | WO-2017079673 A1 * | 5/2017 | ........ C07K 14/70503 |
| WO | WO2019173636 | 9/2019 | |

OTHER PUBLICATIONS

Wu, Y., et al. "Using gene editing to establish a safeguard system for pluripotent stem-cell-based therapies. iScience 22, 409-422." 2019, (Year: 2019).*

Liang, Qin, et al. "Linking a cell-division gene and a suicide gene to define and improve cell therapy safety." Nature 563.7733 (2018): 701-704. (Year: 2018).*

Cheng, Fuyi, et al. "Protecting against wayward human induced pluripotent stem cells with a suicide gene." Biomaterials 33.11 (2012): 3195-3204. (Year: 2012).*

Lo, Chiu-An, Alexander W. Greben, and Brian Edwin Chen. "Generating stable cell lines with quantifiable protein production using CRISPR/Cas9-mediated knock-in." Biotechniques 62.4 (2017): 165-174. (Year: 2017).*

Manghwar, Hakim, et al. "CRISPR/Cas systems in genome editing: methodologies and tools for sgRNA design, off-target evaluation, and strategies to mitigate off-target effects." Advanced science 7.6 (2020): 1902312. (Year: 2020).*

Rong, Zhili, et al. "A scalable approach to prevent teratoma formation of human embryonic stem cells." Journal of Biological Chemistry 287.39 (2012): 32338-32345. (Year: 2012).*

Stavrou, Maria, et al. "A rapamycin-activated caspase 9-based suicide gene." Molecular Therapy 26.5 (2018): 1266-1276. (Year: 2018).*

Straathof, Karin C., et al. "An inducible caspase 9 safety switch for T-cell therapy." Blood 105.11 (2005): 4247-4254. (Year: 2005).*

* cited by examiner

*Primary Examiner* — Tracy Vivlemore

*Assistant Examiner* — Fatimah Khalaf Matalkah

(74) *Attorney, Agent, or Firm* — Pamela J. Sherwood; Andrew R. Guzman; Bozicevic, Field & Francis LLP

(57) ABSTRACT

Compositions and methods are provided for depletion of pluripotent cells. In one embodiment of the invention, methods are provided for depletion of pluripotent cells from a mixed population of differentiated cells and stem cells, to provide a population of cells substantially free of pluripotent stem cells.

7 Claims, 47 Drawing Sheets

Specification includes a Sequence Listing.

D *NANOG*$^{iCasp9\text{-}YFP}$; *ACTB*$^{TK\text{-}mPlum}$ hPSCs are karyotypically normal

E *NANOG* and iCasp9 mRNAs are linked in *NANOG*$^{iCasp9\text{-}YFP}$ hESCs

C

A Genetic knock-in efficiencies

| Locus | Size/Type of Insertion | Editing Efficiency |
|---|---|---|
| *NANOG* | 2082 bp (*iCasp9- YFP*) | 1.45% |
| *ACTB* | 1965 bp (*OiCasp9- mPlum*) | 11.7% |

B $NANOG^{iCasp9\text{-}YFP}$; $ACTB^{OiCasp9\text{-}mPlum}$ hPSCs are karyotypically normal

F AP21967 eliminates ACTB$^{OiCasp9\text{-}mPlum}$ hESC-derived teratomas in all treated mice

*NANOG$^{iCasp9\text{-}YFP}$ACTB$^{OiCasp9\text{-}mPlum}$; PiggyBac-AkaLuciferase hPSCs*

SEQUENCE LISTING

<160> NUMBER OF SEQ ID NOS: 74

<210> SEQ ID NO 1
<211> LENGTH: 23
<212> TYPE: DNA
<213> ORGANISM: Artificial sequence
<220> FEATURE:
<223> OTHER INFORMATION: synthetic sequence

<400> SEQUENCE: 1
actcatcttc acacgtcttc agg 23

<210> SEQ ID NO 2
<211> LENGTH: 23
<212> TYPE: DNA
<213> ORGANISM: Artificial sequence
<220> FEATURE:
<223> OTHER INFORMATION: synthetic sequence

<400> SEQUENCE: 2
ccgcctagaa gcatttgcgg tgg 23

<210> SEQ ID NO 3
<211> LENGTH: 22
<212> TYPE: DNA
<213> ORGANISM: Artificial sequence
<220> FEATURE:
<223> OTHER INFORMATION: synthetic sequence

<400> SEQUENCE: 3
gagctggttc agaaggccaa ac 22

<210> SEQ ID NO 4
<211> LENGTH: 26
<212> TYPE: DNA
<213> ORGANISM: Artificial sequence
<220> FEATURE:
<223> OTHER INFORMATION: synthetic sequence

<400> SEQUENCE: 4
ccttgctcag ttacagactt catgca 26

<210> SEQ ID NO 5
<211> LENGTH: 19
<212> TYPE: DNA
<213> ORGANISM: Artificial sequence
<220> FEATURE:
<223> OTHER INFORMATION: synthetic sequence

<400> SEQUENCE: 5
tggacagtta cgcgcacat 19

<210> SEQ ID NO 6
<211> LENGTH: 21
<212> TYPE: DNA
<213> ORGANISM: Artificial sequence
<220> FEATURE:
<223> OTHER INFORMATION: synthetic sequence

<400> SEQUENCE: 6
cgagtaggac atgctgtagg t 21

<210> SEQ ID NO 7
<211> LENGTH: 20
<212> TYPE: DNA
<213> ORGANISM: Artificial sequence
<220> FEATURE:
<223> OTHER INFORMATION: synthetic sequence

<400> SEQUENCE: 7
agtgagaggc aacctggaga 20

<210> SEQ ID NO 8
<211> LENGTH: 20
<212> TYPE: DNA
<213> ORGANISM: Artificial sequence
<220> FEATURE:
<223> OTHER INFORMATION: synthetic sequence

<400> SEQUENCE: 8
acactcggac cacatccttc 20

<210> SEQ ID NO 9
<211> LENGTH: 21
<212> TYPE: DNA
<213> ORGANISM: Artificial sequence
<220> FEATURE:
<223> OTHER INFORMATION: synthetic sequence

<400> SEQUENCE: 9
catgagtgtg gatccagctt g 21

<210> SEQ ID NO 10
<211> LENGTH: 21
<212> TYPE: DNA
<213> ORGANISM: Artificial sequence
<220> FEATURE:
<223> OTHER INFORMATION: synthetic sequence

<400> SEQUENCE: 10
cctgaataag cagatccatg g 21

<210> SEQ ID NO 11

<211> LENGTH: 22
<212> TYPE: DNA
<213> ORGANISM: Artificial sequence
<220> FEATURE:
<223> OTHER INFORMATION: synthetic sequence

<400> SEQUENCE: 11
agcctaaatg atggtgcttg gt 22

<210> SEQ ID NO 12
<211> LENGTH: 22
<212> TYPE: DNA
<213> ORGANISM: Artificial sequence
<220> FEATURE:
<223> OTHER INFORMATION: synthetic sequence

<400> SEQUENCE: 12
ccttgtcaaa gtatgcagca gt 22

<210> SEQ ID NO 13
<211> LENGTH: 23
<212> TYPE: DNA
<213> ORGANISM: Artificial sequence
<220> FEATURE:
<223> OTHER INFORMATION: synthetic sequence

<400> SEQUENCE: 13
aaactacagg tcaagtggta gcc 23

<210> SEQ ID NO 14
<211> LENGTH: 21
<212> TYPE: DNA
<213> ORGANISM: Artificial sequence
<220> FEATURE:
<223> OTHER INFORMATION: synthetic sequence

<400> SEQUENCE: 14
tcctgcataa gcacatcctg a 21

<210> SEQ ID NO 15
<211> LENGTH: 19
<212> TYPE: DNA
<213> ORGANISM: Artificial sequence
<220> FEATURE:
<223> OTHER INFORMATION: synthetic sequence

<400> SEQUENCE: 15
aaatgcggcc cctgtttct 19

<210> SEQ ID NO 16
<211> LENGTH: 19
<212> TYPE: DNA
<213> ORGANISM: Artificial sequence
<220> FEATURE:
<223> OTHER INFORMATION: synthetic sequence

<400> SEQUENCE: 16
cagtgcgtct tgaggagca 19

<210> SEQ ID NO 17
<211> LENGTH: 22
<212> TYPE: DNA
<213> ORGANISM: Artificial sequence
<220> FEATURE:
<223> OTHER INFORMATION: synthetic sequence

<400> SEQUENCE: 17
tctagctcct ataccaccac ca 22

<210> SEQ ID NO 18
<211> LENGTH: 22
<212> TYPE: DNA
<213> ORGANISM: Artificial sequence
<220> FEATURE:
<223> OTHER INFORMATION: synthetic sequence

<400> SEQUENCE: 18
tcgtctccaa cttatctcct cc 22

<210> SEQ ID NO 19
<211> LENGTH: 20
<212> TYPE: DNA
<213> ORGANISM: Artificial sequence
<220> FEATURE:
<223> OTHER INFORMATION: synthetic sequence

<400> SEQUENCE: 19
tcccagaatg caacccagac 20

<210> SEQ ID NO 20
<211> LENGTH: 22
<212> TYPE: DNA
<213> ORGANISM: Artificial sequence
<220> FEATURE:
<223> OTHER INFORMATION: synthetic sequence

<400> SEQUENCE: 20
ggtgagtcac tggatacacc aa 22

<210> SEQ ID NO 21
<211> LENGTH: 21
<212> TYPE: DNA
<213> ORGANISM: Artificial sequence
<220> FEATURE:
<223> OTHER INFORMATION: synthetic sequence

<400> SEQUENCE: 21
aggaccaccg catctctaca t 21

<210> SEQ ID NO 22
<211> LENGTH: 21
<212> TYPE: DNA
<213> ORGANISM: Artificial sequence
<220> FEATURE:
<223> OTHER INFORMATION: synthetic sequence

<400> SEQUENCE: 22
aagtctggct cgttctcagt g 21

<210> SEQ ID NO 23
<211> LENGTH: 20
<212> TYPE: DNA
<213> ORGANISM: Artificial sequence
<220> FEATURE:
<223> OTHER INFORMATION: synthetic sequence

<400> SEQUENCE: 23
tgcttccctg agacccagtt 20

<210> SEQ ID NO 24

<211> LENGTH: 25
<212> TYPE: DNA
<213> ORGANISM: Artificial sequence
<220> FEATURE:
<223> OTHER INFORMATION: synthetic sequence

<400> SEQUENCE: 24
gatcacttct ttcctttgca tcaag 25

<210> SEQ ID NO 25
<211> LENGTH: 20
<212> TYPE: DNA
<213> ORGANISM: Artificial sequence
<220> FEATURE:
<223> OTHER INFORMATION: synthetic sequence

<400> SEQUENCE: 25
ggtaccccga catccacttg 20

<210> SEQ ID NO 26
<211> LENGTH: 20
<212> TYPE: DNA
<213> ORGANISM: Artificial sequence
<220> FEATURE:
<223> OTHER INFORMATION: synthetic sequence

<400> SEQUENCE: 26
taatctccgg cctagccaaa 20

<210> SEQ ID NO 27
<211> LENGTH: 20
<212> TYPE: DNA
<213> ORGANISM: Artificial sequence
<220> FEATURE:
<223> OTHER INFORMATION: synthetic sequence

<400> SEQUENCE: 27
cgcacggaat ttgaacagta 20

<210> SEQ ID NO 28
<211> LENGTH: 20
<212> TYPE: DNA
<213> ORGANISM: Artificial sequence
<220> FEATURE:
<223> OTHER INFORMATION: synthetic sequence

<400> SEQUENCE: 28
ggatcaggga cctgtcacac 20

<210> SEQ ID NO 29
<211> LENGTH: 22
<212> TYPE: DNA
<213> ORGANISM: Artificial sequence
<220> FEATURE:
<223> OTHER INFORMATION: synthetic sequence

<400> SEQUENCE: 29
tcatgcaggt gtgtgagtcc at 22

<210> SEQ ID NO 30
<211> LENGTH: 22
<212> TYPE: DNA
<213> ORGANISM: Artificial sequence
<220> FEATURE:
<223> OTHER INFORMATION: synthetic sequence

<400> SEQUENCE: 30
agtcattgcc taggagcagc ac 22

<210> SEQ ID NO 31
<211> LENGTH: 22
<212> TYPE: DNA
<213> ORGANISM: Artificial sequence
<220> FEATURE:
<223> OTHER INFORMATION: synthetic sequence

<400> SEQUENCE: 31
ttaccaagtc gggaaggcga at 22

<210> SEQ ID NO 32
<211> LENGTH: 22
<212> TYPE: DNA
<213> ORGANISM: Artificial sequence
<220> FEATURE:
<223> OTHER INFORMATION: synthetic sequence

<400> SEQUENCE: 32
catcctcttt ggcatttcgg gg 22

<210> SEQ ID NO 33
<211> LENGTH: 20
<212> TYPE: DNA
<213> ORGANISM: Artificial sequence
<220> FEATURE:
<223> OTHER INFORMATION: synthetic sequence

<400> SEQUENCE: 33
cggaattacc tgccacctgt 20

<210> SEQ ID NO 34
<211> LENGTH: 20
<212> TYPE: DNA
<213> ORGANISM: Artificial sequence
<220> FEATURE:
<223> OTHER INFORMATION: synthetic sequence

<400> SEQUENCE: 34
ggtctgtgag ttccccgatg 20

<210> SEQ ID NO 35
<211> LENGTH: 20
<212> TYPE: DNA
<213> ORGANISM: Artificial sequence
<220> FEATURE:
<223> OTHER INFORMATION: synthetic sequence

<400> SEQUENCE: 35
ctgcagcacc ggcaccgttt 20

<210> SEQ ID NO 36
<211> LENGTH: 20
<212> TYPE: DNA
<213> ORGANISM: Artificial sequence
<220> FEATURE:
<223> OTHER INFORMATION: synthetic sequence

<400> SEQUENCE: 36
cccaacggct ggacgcacac 20

<210> SEQ ID NO 37

<211> LENGTH: 24
<212> TYPE: DNA
<213> ORGANISM: Artificial sequence
<220> FEATURE:
<223> OTHER INFORMATION: synthetic sequence

<400> SEQUENCE: 37
cgtcaacggc tccagcaaga acaa 24

<210> SEQ ID NO 38
<211> LENGTH: 26
<212> TYPE: DNA
<213> ORGANISM: Artificial sequence
<220> FEATURE:
<223> OTHER INFORMATION: synthetic sequence

<400> SEQUENCE: 38
gccgcttctc gctctcgttc agaagt 26

<210> SEQ ID NO 39
<211> LENGTH: 24
<212> TYPE: DNA
<213> ORGANISM: Artificial sequence
<220> FEATURE:
<223> OTHER INFORMATION: synthetic sequence

<400> SEQUENCE: 39
cgctatggag cagacgtatg gcga 24

<210> SEQ ID NO 40
<211> LENGTH: 22
<212> TYPE: DNA
<213> ORGANISM: Artificial sequence
<220> FEATURE:
<223> OTHER INFORMATION: synthetic sequence

<400> SEQUENCE: 40
aatgcgcaag cggatggcgt tg 22

<210> SEQ ID NO 41
<211> LENGTH: 24
<212> TYPE: DNA
<213> ORGANISM: Artificial sequence
<220> FEATURE:
<223> OTHER INFORMATION: synthetic sequence

<400> SEQUENCE: 41
tggttatgtt gctggacatg ggtg 24

<210> SEQ ID NO 42
<211> LENGTH: 25
<212> TYPE: DNA
<213> ORGANISM: Artificial sequence
<220> FEATURE:
<223> OTHER INFORMATION: synthetic sequence

<400> SEQUENCE: 42
ggaagccgtg acagaatgac tacct 25

<210> SEQ ID NO 43
<211> LENGTH: 22
<212> TYPE: DNA
<213> ORGANISM: Artificial sequence
<220> FEATURE:
<223> OTHER INFORMATION: synthetic sequence

<400> SEQUENCE: 43
ggaagcactg tttgccaaga cc 22

<210> SEQ ID NO 44
<211> LENGTH: 22
<212> TYPE: DNA
<213> ORGANISM: Artificial sequence
<220> FEATURE:
<223> OTHER INFORMATION: synthetic sequence

<400> SEQUENCE: 44
ctgttgttgg cggcacttag ct 22

<210> SEQ ID NO 45
<211> LENGTH: 21
<212> TYPE: DNA
<213> ORGANISM: Artificial sequence
<220> FEATURE:
<223> OTHER INFORMATION: synthetic sequence

<400> SEQUENCE: 45
gcagatgcaa aagtccaggt g 21

<210> SEQ ID NO 46
<211> LENGTH: 22
<212> TYPE: DNA
<213> ORGANISM: Artificial sequence
<220> FEATURE:
<223> OTHER INFORMATION: synthetic sequence

<400> SEQUENCE: 46
caggttgcga agaactctgt tt 22

<210> SEQ ID NO 47
<211> LENGTH: 19
<212> TYPE: DNA
<213> ORGANISM: Artificial sequence
<220> FEATURE:
<223> OTHER INFORMATION: synthetic sequence

<400> SEQUENCE: 47
ccgcacccgt caatgactt 19

<210> SEQ ID NO 48
<211> LENGTH: 21
<212> TYPE: DNA
<213> ORGANISM: Artificial sequence
<220> FEATURE:
<223> OTHER INFORMATION: synthetic sequence

<400> SEQUENCE: 48
ccgtcgtaaa acttggcaaa g 21

<210> SEQ ID NO 49
<211> LENGTH: 20
<212> TYPE: DNA
<213> ORGANISM: Artificial sequence
<220> FEATURE:
<223> OTHER INFORMATION: synthetic sequence

<400> SEQUENCE: 49
ctgcccaccc tcaacttctc 20

<210> SEQ ID NO 50

<211> LENGTH: 21
<212> TYPE: DNA
<213> ORGANISM: Artificial sequence
<220> FEATURE:
<223> OTHER INFORMATION: synthetic sequence

<400> SEQUENCE: 50
gcaggatcga ctcgtgtttg t 21

<210> SEQ ID NO 51
<211> LENGTH: 21
<212> TYPE: DNA
<213> ORGANISM: Artificial sequence
<220> FEATURE:
<223> OTHER INFORMATION: synthetic sequence

<400> SEQUENCE: 51
tcgggacttg gtttatcacc t 21

<210> SEQ ID NO 52
<211> LENGTH: 19
<212> TYPE: DNA
<213> ORGANISM: Artificial sequence
<220> FEATURE:
<223> OTHER INFORMATION: synthetic sequence

<400> SEQUENCE: 52
gcaagcggca gtagaccag 19

<210> SEQ ID NO 53
<211> LENGTH: 20
<212> TYPE: DNA
<213> ORGANISM: Artificial sequence
<220> FEATURE:
<223> OTHER INFORMATION: synthetic sequence

<400> SEQUENCE: 53
ccagatgagt gtgggtcaga 20

<210> SEQ ID NO 54
<211> LENGTH: 20
<212> TYPE: DNA
<213> ORGANISM: Artificial sequence
<220> FEATURE:
<223> OTHER INFORMATION: synthetic sequence

<400> SEQUENCE: 54
tgctcaggat gtaagccaaa 20

<210> SEQ ID NO 55
<211> LENGTH: 21
<212> TYPE: DNA
<213> ORGANISM: Artificial sequence
<220> FEATURE:
<223> OTHER INFORMATION: synthetic sequence

<400> SEQUENCE: 55
ggagcgagat ccctccaaaa t 21

<210> SEQ ID NO 56
<211> LENGTH: 23
<212> TYPE: DNA
<213> ORGANISM: Artificial sequence
<220> FEATURE:
<223> OTHER INFORMATION: synthetic sequence

<400> SEQUENCE: 56
ggctgttgtc atacttctca tgg 23

<210> SEQ ID NO 57
<211> LENGTH: 19
<212> TYPE: DNA
<213> ORGANISM: Artificial sequence
<220> FEATURE:
<223> OTHER INFORMATION: synthetic sequence

<400> SEQUENCE: 57
agcccagaac actggtctc 19

<210> SEQ ID NO 58
<211> LENGTH: 21
<212> TYPE: DNA
<213> ORGANISM: Artificial sequence
<220> FEATURE:
<223> OTHER INFORMATION: synthetic sequence

<400> SEQUENCE: 58
actcaggatt tcaatggtgc c 21

<210> SEQ ID NO 59
<211> LENGTH: 20
<212> TYPE: DNA
<213> ORGANISM: Artificial sequence
<220> FEATURE:
<223> OTHER INFORMATION: synthetic sequence

<400> SEQUENCE: 59
agagctacga gctgcctgac 20

<210> SEQ ID NO 60
<211> LENGTH: 20
<212> TYPE: DNA
<213> ORGANISM: Artificial sequence
<220> FEATURE:
<223> OTHER INFORMATION: synthetic sequence

<400> SEQUENCE: 60
agcactgtgt tggcgtacag 20

<210> SEQ ID NO 61
<211> LENGTH: 23
<212> TYPE: DNA
<213> ORGANISM: Artificial sequence
<220> FEATURE:
<223> OTHER INFORMATION: synthetic sequence

<400> SEQUENCE: 61
actcatcttc acacgtcttc agg 23

<210> SEQ ID NO 62
<211> LENGTH: 23
<212> TYPE: DNA
<213> ORGANISM: Artificial sequence
<220> FEATURE:
<223> OTHER INFORMATION: synthetic sequence

<400> SEQUENCE: 62
ccgcctagaa gcatttgcgg cgg 23

<210> SEQ ID NO 63

<211> LENGTH: 18
<212> TYPE: DNA
<213> ORGANISM: Artificial sequence
<220> FEATURE:
<223> OTHER INFORMATION: synthetic sequence

<400> SEQUENCE: 63
ccaccattat agatctct 18

<210> SEQ ID NO 64
<211> LENGTH: 20
<212> TYPE: DNA
<213> ORGANISM: Artificial sequence
<220> FEATURE:
<223> OTHER INFORMATION: synthetic sequence

<400> SEQUENCE: 64
tgtcattacg atgcagcaaa 20

<210> SEQ ID NO 65
<211> LENGTH: 20
<212> TYPE: DNA
<213> ORGANISM: Artificial sequence
<220> FEATURE:
<223> OTHER INFORMATION: synthetic sequence

<400> SEQUENCE: 65
agttcatgcg cttcaaggag 20

<210> SEQ ID NO 66
<211> LENGTH: 21
<212> TYPE: DNA
<213> ORGANISM: Artificial sequence
<220> FEATURE:
<223> OTHER INFORMATION: synthetic sequence

<400> SEQUENCE: 66
tgaatggggg ttgaatgatt a 21

<210> SEQ ID NO 67
<211> LENGTH: 19
<212> TYPE: DNA
<213> ORGANISM: Artificial sequence
<220> FEATURE:
<223> OTHER INFORMATION: synthetic sequence

<400> SEQUENCE: 67
ctcagatcat tgctcctcc 19

<210> SEQ ID NO 68
<211> LENGTH: 20
<212> TYPE: DNA
<213> ORGANISM: Artificial sequence
<220> FEATURE:
<223> OTHER INFORMATION: synthetic sequence

<400> SEQUENCE: 68
agaagtgggg tggcttttag 20

<210> SEQ ID NO 69
<211> LENGTH: 21
<212> TYPE: DNA
<213> ORGANISM: Artificial sequence
<220> FEATURE:
<223> OTHER INFORMATION: synthetic sequence

<400> SEQUENCE: 69
gcacatcttg ccaggatttt a 21

<210> SEQ ID NO 70
<211> LENGTH: 20
<212> TYPE: DNA
<213> ORGANISM: Artificial sequence
<220> FEATURE:
<223> OTHER INFORMATION: synthetic sequence

<400> SEQUENCE: 70
tcctatgaag gatgggagga 20

<210> SEQ ID NO 71
<211> LENGTH: 21
<212> TYPE: PRT
<213> ORGANISM: thosea asigna virus 2A

<400> SEQUENCE: 71

Gly Ser Gly Glu Gly Arg Gly Ser Leu Leu Thr Cys Gly Asp Val Glu
1 5 10 15

Glu Asn Pro Gly Pro
20

<210> SEQ ID NO 72
<211> LENGTH: 22
<212> TYPE: PRT
<213> ORGANISM: porcine teschovirus-1 2A

<400> SEQUENCE: 72

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 73
<211> LENGTH: 23
<212> TYPE: PRT
<213> ORGANISM: equine rhinitis A virus

<400> SEQUENCE: 73

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 74
<211> LENGTH: 25
<212> TYPE: PRT
<213> ORGANISM: foot-and-mouth disease virus 18

<400> SEQUENCE: 74

Gly Ser Gly Val Lys Gln Thr Leu Asn Phe Asp Leu Leu Lys Leu Ala
1 5 10 15

Gly Asp Val Glu Ser Asn Pro Gly Pro
20 25

ORTHOGONAL SAFETY SWITCHES TO ELIMINATE GENETICALLY ENGINEERED CELLS

CROSS REFERENCE

This application claims priority to U.S. Provisional Application No. 62/981,191, filed Feb. 25, 2020, which is incorporated herein in its entirety for all purpose.

GOVERNMENT SUPPORT RESEARCH

This invention was made with Government support under contract OD024558 awarded by the National Institutes of Health. The Government has certain rights in the invention.

BACKGROUND OF THE INVENTION

Increasing numbers of hPSC-derived cell therapies have been transplanted into patients, with over 30 ongoing or completed clinical trials for multiple indications, including spinal cord injury, macular degeneration and Type 1 Diabetes. The breadth of these clinical trials highlights the promise of hPSC-derived cell therapies. However, hPSC-based therapies present unique safety risks compared to adult-derived cell therapies. To realize the potential of hPSC-derived therapies, strategies to mitigate these unique risks need to be further developed. These risks fall into two main categories.

First, hPSC differentiation often yields a heterogeneous cell population, and even a small number of residual undifferentiated hPSCs (as few as 10,000) can form a teratoma in vivo. If billions of hPSC-derived cells are to be transplanted into a patient, even 0.001% remaining hPSCs might be therapeutically unacceptable; thus a 5-log depletion of undifferentiated hPSCs will be critical. Indeed, transplantation of certain hPSC-derived liver and pancreatic populations yielded teratomas in animal models, which would be concerning if they similarly arose in human patients.

Second, differentiated cell-types of the wrong lineage can, upon transplantation, generate tissue overgrowths or unwanted tissues altogether. For example, transplantation of PSC-derived neural populations into animal models generated neural overgrowths or cysts in some cases. These safety issues may be further exacerbated as hPSCs are engineered to be "hypoimmunogenic" in order to minimize their rejection by patients' immune systems. Notably, if hPSC-derived "hypoimmunogenic" cells become malignantly transformed or virally infected, they may not be adequately controlled by the recipient's immune system.

Specific and inducible safety switches for transplanted hPSC therapies are of great clinical interest, and are provided herein.

SUMMARY

Safety switches for the elimination of genetically engineered cells, and methods of use thereof, are provided. The safety switches are nucleic acid constructs encoding a switch protein that inducibly causes cell death or stops cell proliferation. The safety switch is inserted at a defined, specific target locus in the genome of an engineered cell, usually at both alleles of the target locus. The switch is activated by contacting with an effective dose of a clinically acceptable orthologous small molecule, which may be referred to as an orthologous activating agent. When activated, the safety switch causes the cell to stop proliferation, in some embodiments by activating apoptosis of the cell.

The safety switch is inserted at a targeted site of the genome, where it is operably linked to the promoter of a gene of interest, without disrupting expression of the gene of interest. In some embodiments the safety switch is integrated to replace the stop codon of the gene of interest. The switch protein in this embodiment may be flanked by self-cleaving peptide sequences to provide for cleavage of the gene of interest protein and the switch protein.

In some embodiments the gene of interest for targeting a safety switch is specifically expressed only in pluripotent cells, and may be referred to as a "selective switch". Desirably the protein encoded by the gene of interest is required for maintaining a pluripotent state. A selectively expressed gene will have undetectable levels of transcript in differentiated cells. In some embodiment the gene of interest is NANOG, which is shown herein to be both highly selectively expressed, and to be required for the pluripotent state. A selective switch integrated at the NANOG locus, when activated, will selectively kill only pluripotent cells, because NANOG is not expressed in differentiated cells. An important feature of the selective safety switch is the ability to achieve a greater than $10^6$-fold killing of pluripotent cells when contacted with the orthologous activating agent in vitro. This high level of killing allows a population of engineered cells to be purged of pluripotent cells prior to in vivo use.

In some embodiments a second safety switch is integrated at a second target locus. The second gene of interest can be selected to be a gene that is ubiquitously expressed and preferably required for cell survival. In some embodiments the second gene of interest is a housekeeping gene. In some embodiments the second gene of interest is beta actin (ACTB). A safety switch integrated at the ubiquitous locus may be referred to as a "general switch". Activation of a general switch will kill or stop replication of both differentiated cells of various lineages, and of pluripotent cells, thereby generally deleting engineered cells. It may be noted that it is the site of integration that determines whether a switch is selective or general, not the sequence of the safety switch itself.

In embodiments where a cell is engineered to comprise a first, selective safety switch and a second, general safety switch, the two switches are activated by different orthologous activating agents.

In some embodiments the protein encoded by the safety switch protein is a protein that induces apoptosis upon dimerization. In some embodiments the protein is a human caspase protein, e.g. caspase 1, caspase 2, caspase 3, caspase 4, caspase 5, caspase 6, caspase 7, caspase 8, caspase 9, caspase 10, caspase 14, etc. In certain embodiments the protein is human caspase 9. The caspase protein is fused to a sequence that provides for chemically induced dimerization (CID), in which dimerization occurs only in the presence of the orthologous activating agent. One or more CID domains may be fused to the caspase protein, e.g. two different CID domains may be fused to the caspase protein. In some embodiments the CID domain is a dimerization domain of FKBP or FRB (FKBP-rapamycin-binding) domain of mTOR, which are activated with rapamycin analogs. The CID may be one or both of an Frb domain comprising amino acids 2025-2114 of human mTor with amino acid substitutions Lys2095 to Pro, Thr2098 to Leu, and Trp2101 to Phe, which is dimerized by AP21967 (AP21); and an F36V mutant of human FKBP domain ($FKBP^{F36V}$), which is activated by AP20187 (AP20). The dose of activating agent may be, for example, from about 0.1 nm to about 100 nm, e.g. 0.5 nm, 1 nm, 5 nm, 10 nm, 50 nm, etc. If administered in vivo, the dose may be comparable to rapamycin, e.g. a trough serum concentration of around 10 to 50 nm, administered at from about 1 to about 5 mg/M$^2$.

In other embodiments the protein encoded by the safety switch is a thymidine kinase of viral origin that phosphorylates nucleoside analogs such as acyclovir, ganciclovir, etc. causing a termination of chain elongation and halting cell proliferation. Examples include, without limitation, the thymidine kinase from herpesviruses, e.g. HSV, VZV, CMV, EBV, etc. In some embodiments the switch protein is TK$^{HSV}$, and the activating agent is ganciclovir. The dose of orthogonal activating agent may be from about 0.5 mg/kg to about 5 mg/kg.

Compositions are provided of genetic sequences encoding safety switches. Examples of constructs are provided in FIG. 2C, FIG. 4B, and FIG. 6B. The genetic construct comprises the coding sequence for the switch protein, which is optionally flanked by self-cleaving peptide sequences. Optionally, downstream of the switch protein and self-cleaving peptide sequence, a selectable marker sequence may be present. The selectable marker for research purposes may be a fluorescent protein, luminescent protein, etc. The selectable marker for clinical purposes may be a human protein, e.g. CD19, CD20, EGFR, truncated NGFR, and the like. High efficiency engineering systems may not require a selectable marker. The genetic construct may comprise homologous sequences for recombination at the target locus. The safety switch genetic sequence may be provided in a viral vector suitable for integration. In some embodiments the viral vector is an AAV vector, e.g. any one of the AAV serotypes AAV1, AAV2, AAV3, AAV4, AAV5, AAV6, AAV7, AAV8, AAV9, AAV10, AAV11, etc. In some embodiments the vector is AAV6.

Kits are provided for insertion of the safety switch into a cell, e.g. a pluripotent cell. A kit will comprise a vector encoding at least one, and preferably two different safety switches. A kit may further comprise agents for precise genetic recombination, e.g. a cas9 protein and suitable guide RNAs for a locus of interest, including without limitation NANOG, ACTB, etc. Kits may further comprise orthologous activating agents, e.g. acyclovir or ganciclovir; AP20, AP21, etc.

Methods are provided for engineering a safety switch or multiple safety switches into a cell. A cell, usually a pluripotent cell, is contacted with a cas9 protein and guide RNA for insertion into the target locus. In some embodiments the Cas9 is provided as a ribonucleoprotein complex with sgRNA, which is electroporated into the cell. The cell is then contacted with the vector comprising the safety switch. Depending on the efficiency of the process, the cells can be selected for the presence of the safety switch. Cells can be produced and grown under GMP conditions for use in human therapy, and may be banked for further use.

In one embodiment of the invention, methods are provided for depletion of pluripotent cells from a mixed population of differentiated cells and stem cells, to provide a population of cells substantially free of pluripotent stem cells. Generally, therapeutic cells are differentiated from the initial pluripotent population to a desired differentiated cell type. Following differentiation, the cells are contacted with an effective dose of the orthologous activating agent for the selective switch, for a period of from about 12, about 24, about 36, about 48 hours, to cause a greater than $10^6$-fold reduction in the number of pluripotent cells in the population, while leaving viable differentiated cells.

In one embodiment of the invention, methods are provided for depletion of engineered cells that may be differentiated or that may be pluripotent. Following transfer of the engineered cells to a subject, there can be cause to wish to generally deplete the engineered cells, e.g. if the cells show excess proliferation, are the cause of undesirable immune responses, and the like. In such cases, the orthologous activating agent for the general switch is provided to the subject in a dose effective to deplete the engineered cells, e.g. from about 0.1 mg/kg to about 100 mg/kg, e.g. 0.1 mg/kg, 0.5 mg/kg, 1 mg/kg, 10 mg/kg, 50 mg/kg, etc., and ranges in between.

In one embodiment a composition of engineered cells is provided. In some embodiments the cells are human cells. In some embodiments the cells are pluripotent. The cells may be provided in a pharmaceutically acceptable excipient, in frozen form, etc. The cells comprise a first, selective safety switch integrated at the stop codon of NANOG, which safety switch comprises a sequence encoding caspase protein fused to a CID domain activated by an orthologous agent. In some embodiments the CID domain is FKBP$^{F36V}$ activated by AP20.

In some embodiments the cell comprises a second, general safety switch, integrated at the stop codon of a housekeeping gene. In some embodiments the housekeeping gene is ACTB. In some embodiments the safety switch comprises a sequence encoding a caspase protein fused to a second CID domain activated by a second orthologous agent. In some embodiments the CID domain is Frb, activated by AP21, which also activates FKBP$^{F36V}$.

In other embodiments the cell comprises a second, general safety switch, integrated at the stop codon of a housekeeping gene, which safety switch comprises a sequence encoding a viral TK that phosphorylates acyclovir or ganciclovir. In some embodiments the viral TK is a herpesvirus TK. In some embodiments the TK is HSV TK.

DETAILED DESCRIPTION OF THE EMBODIMENTS

Figure 1:
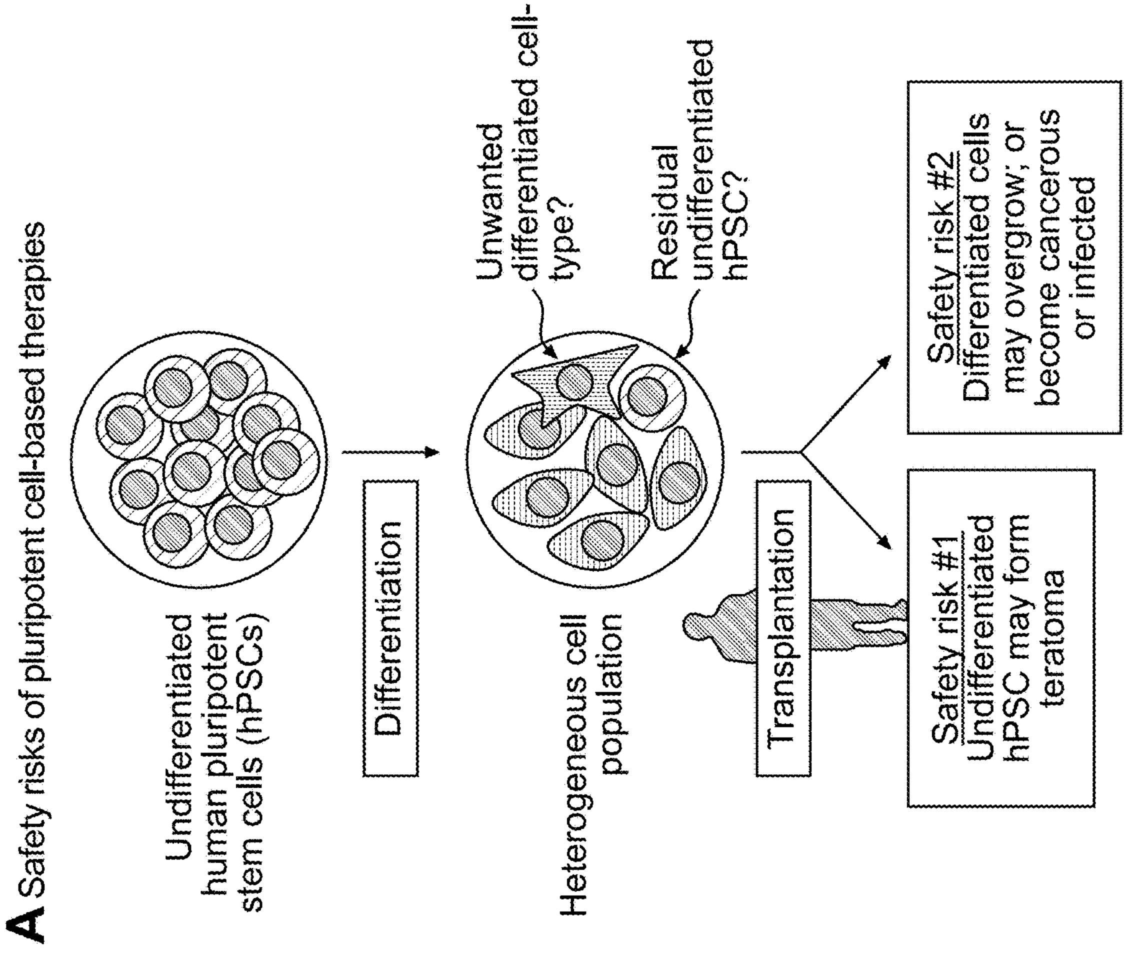
FIG. 1: Genetically engineered safeguards for human pluripotent stem cell-based therapies A) Safety risks of hPSC-based cell therapies. B) Summary of the safeguards described in this study. C) Applications of the safeguards described in this study. D) Small molecules used to activate respective safeguards.
Figure 1:
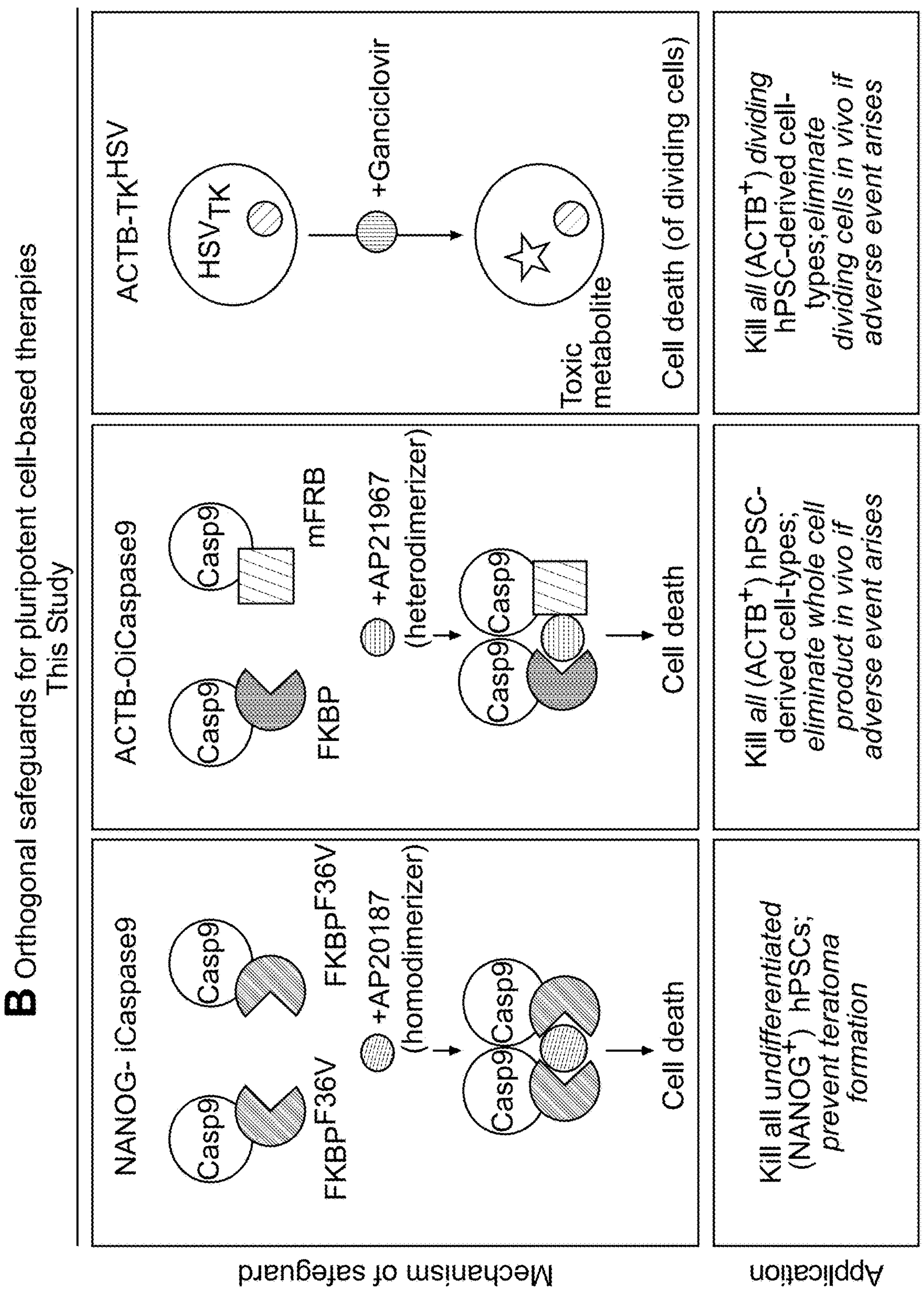
Figure 1:
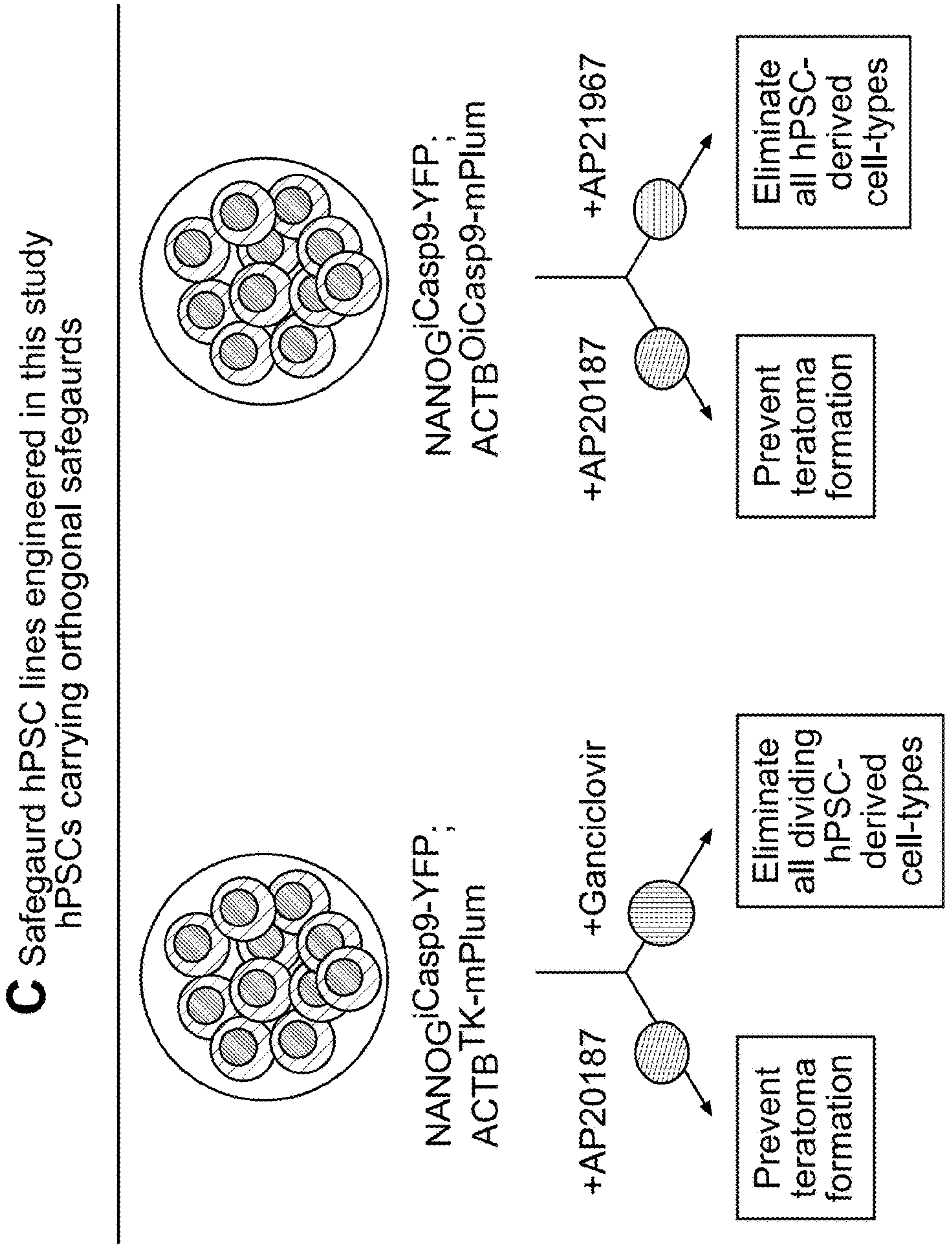
Figure 1:
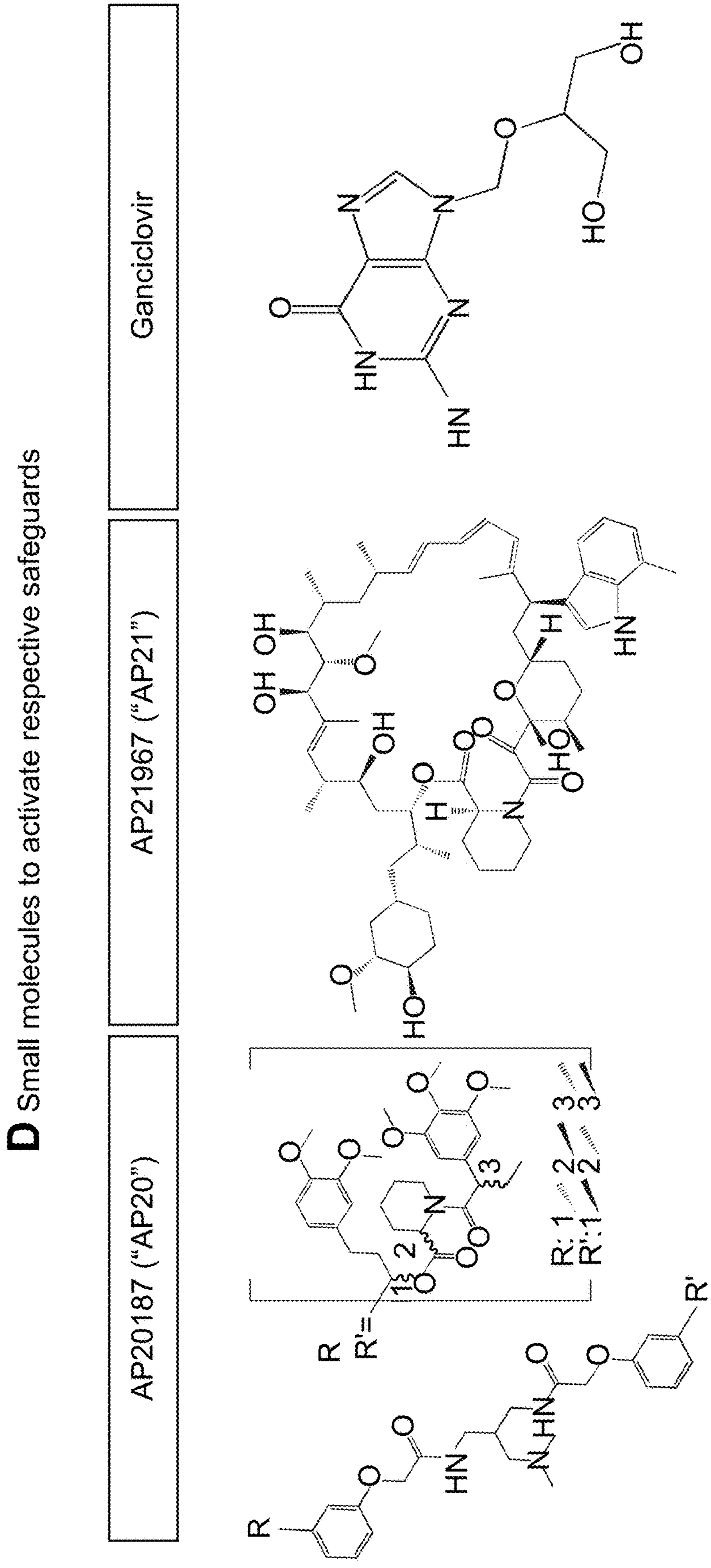

Compositions and methods are provided for depletion of pluripotent cells in vitro or in vivo by activation of a genetic safety switch. Pluripotent cells include iPS cells, embryonic stem cells, teratoma cancer stem cells, germ cell cancers (i.e. teratocarcinomas), etc. In one embodiment of the invention, methods are provided for depletion of pluripotent cells from a mixed population of differentiated cells and stem cells, to provide a population of cells substantially free of pluripotent stem cells. Compositions and methods are also provided for depletion of engineered differentiated cells by activation of a genetic safety switch.

For further elaboration of general techniques useful in the practice of this invention, the practitioner can refer to standard textbooks and reviews in cell biology, tissue culture, embryology, and cardiophysiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998). With respect to the culture of heart cells, standard references include The Heart Cell in Culture (A. Pinson ed., CRC Press 1987), Isolated Adult Cardiomyocytes (Vols. I & II, Piper & Isenberg eds, CRC Press 1989), Heart Development (Harvey & Rosenthal, Academic Press 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Safety switch. As used herein, a safety switch refers to genetic sequence encoding a protein that causes cell death when activated. The safety switch is inserted at a defined, specific target locus in the genome of an engineered cell, usually at both alleles of the target locus. The switch is activated by contacting with an effective dose of an orthologous activating agent. A safety switch is inserted at a selective, or a general (ubiquitous) site in the genome.

Selective site. A selective site is a site in the genome operably linked to the promoter of a gene that is selectively expressed in pluripotent cells, and that is required for maintenance of a pluripotent state. It is shown herein that a number of genes previously believed to be selectively expressed are, in fact, undesirably expressed in differentiated cells. In contrast, NANOG expression is highly selective, and is rapidly downregulated after transition to a differentiated cell type. NANOG is located at Chr 12: 7.79-7.8 Mb of the human genome, and the reference sequence for mRNA is NM_001297698. An exemplary guide RNA for integration at the NANOG locus is provided in the examples as SEQ ID NO:61, 5'-ACTCATCTTCACACGTCTTCAGG-3'.

General Site. A general, or ubiquitous site is a site in the genome operably linked to the promoter of a gene that is ubiquitously expressed in all cells, and that is required for viability of the cells. Beta actin (ACTB) is provided as a useful example for this purpose. ACTB is located at Chr 7: 5.53-5.56 Mb in the human genome. The mRNA refseq in Genbank is NM_001101. An exemplary guide RNA for integration at ACTB is provided in the examples as SEQ ID NO:62, 5'-CCGCCTAGAAGCATTTGCGGCGG-3'.

Many other genes are ubiquitously expressed, e.g. see Ramskold et al. PLoS Comput Biol 5(12): e1000598, which lists such genes. Included in this group are housekeeping genes, which include transcription factors; RNA splicing proteins; translation factors; tRNA synthesis proteins; RNA binding protein; ribosomal proteins; RNA polymerase; protein processing proteins; heat shock proteins; histones; cell cycle proteins; cytoskeletal proteins; metabolism proteins;

Cytochrome C oxidase; proteasome proteins; ubiquitin and ubiquitin-conjugating proteins; ribonuclease; thioreductase; organelle synthesis proteins; channels and transporters; receptors; signaling proteins such as kinases; growth factors; etc. One of skill in the art can readily select from the numerous genes that are well-characterized by sequence and expression.

Caspase proteins. Caspase proteins, which may be referred to as suicide proteins, cause cell death by apoptosis upon dimerization. In some embodiments the protein is a human caspase protein, e.g. caspase 1, caspase 2, caspase 3, caspase 4, caspase 5, caspase 6, caspase 7, caspase 8, caspase 9, caspase 10, caspase 14, etc. For use in a safety switch, the caspase should only dimerize upon activation with an activation agent, and thus the sequence of an inducible caspase is mutated to delete the native dimerization domain.

Under physiological conditions, caspase 9 is activated by the release of cytochrome C from damaged mitochondria. Activated caspase 9 then activates caspase 3, which triggers terminal effector molecules leading to apoptosis. An inducible caspase 9 protein is truncated to delete its physiological dimerization domain (caspase activation domain (CARD), referred to as caspase 9. Δ caspase 9 has low dimerizer-independent basal activity. In a safety switch construct, an inducible caspase protein is linked to a CID domain.

Chemically induced dimerization (CID) domains provide for dimerization only in the presence of the orthologous activating agent. One or more CID domains may be fused to the inducible caspase protein, e.g. one or two different CID domains may be fused to the caspase protein. Examples of CID domains include, without limitation, FKBP and mTOR domains, which can be dimerized with FK102, FK506, AP21, AP20, FKCsA, rapamycin, etc. Other CID domains include GyrB dimerized by Coumermycin; GID1 (gibberellin insensitive dwarf 1) and gibberellin; SNAP-tag and HaXS; Bcl-xL and ABT-737, etc.

In some embodiments the CID domain is a dimerization domain of FKBP or FRB (FKBP-rapamycin-binding) domain of mTOR, which are activated with rapamycin analogs. The CID may be one or both of an Frb domain comprising amino acids 2025-2114 of human mTor with amino acid substitutions Lys2095 to Pro, Thr2098 to Leu, and Trp2101 to Phe, which is dimerized by AP21967 (AP21); and an F36V mutant of human FKBP domain ($FKBP^{F36V}$), which is activated by AP20187 (AP20).

Thymidine kinase. Thymidine kinases (TK) convert thymidine, or deoxythymidine (dT) to the respective monophosphate. TK occurs in many different procaryotic and eucaryotic species and different TK isoenzymes are found within the same eucaryotic cell. Some virus encoded TK has been shown to differ biochemically, immunologically and in substrate specificity from the corresponding TK isoenzymes in target host cells thus facilitating the development of specific antiviral therapeutics.

In some embodiments a thymidine kinase in a safety switch is of viral origin that phosphorylates nucleoside analogs such as acyclovir, ganciclovir, etc. causing a termination of chain elongation and halting cell proliferation. Examples include, without limitation, the thymidine kinase from herpesviruses, e.g. HSV, VZV, CMV, EBV, etc.

Self-cleaving peptides. Self-cleaving peptides, or 2A peptides, are a class of 18-22 aa-long peptides that can induce cleavage of the recombinant protein in cell. The 2A-peptide-mediated cleavage commences after the translation. The cleavage is trigged by breaking of peptide bond between the Proline (P) and Glycine (G) in C-terminal of 2A peptide.

Four members of 2A peptides family are frequently used: P2A, E2A, F2A and T2A. F2A is derived from foot-and-mouth disease virus 18; E2A is derived from equine rhinitis A virus; P2A is derived from porcine teschovirus-1 2A; T2A is derived from *Thosea asigna* virus 2A. The sequences are:

```
T2A
                                     (SEQ ID NO: 71)
(GSG)EGRGSLLTCGDVEENPGP

P2A
                                     (SEQ ID NO: 72)
(GSG)ATNFSLLKQAGDVEENPGP

E2A
                                     (SEQ ID NO: 73)
(GSG)QCTNYALLKLAGDVESNPGP

F2A
                                     (SEQ ID NO: 74)
(GSG)VKQTLNFDLLKLAGDVESNPGP
```

The nucleic acids disclosed herein may be provided on a viral vector. For instance, the nucleic acids may be inserted into a viral vector using well known recombinant techniques. The subsequent viral vector may then be packaged into a virus, such as adenovirus, lentivirus, retrovirus, attenuated virus, adeno-associated virus (AAV), and the like. Viral delivery for gene therapy applications is well known in the art. There exist a variety of options for viruses suitable for such delivery, which may also involve selecting an appropriate viral serotype for delivery and expression in an appropriate tissue.

A vector of a safety switch may include one or more vector specific elements. By “vector specific elements” is meant elements that are used in making, constructing, propagating, maintaining and/or assaying the vector before, during or after its construction and/or before its use in engineering a cell. Such vector specific elements include but are not limited to, e.g., vector elements necessary for the propagation, cloning and selection of the vector during its use and may include but are not limited to, e.g., an origin of replication, a multiple cloning site, a prokaryotic promoter, a phage promoter, a selectable marker (e.g., an antibiotic resistance gene, an encoded enzymatic protein, an encoded fluorescent or chromogenic protein, etc.), and the like. Any convenient vector specific elements may find use, as appropriate, in the vectors as described herein.

A selectable marker for research purposes may be a fluorescent protein, luminescent protein, etc. The selectable marker for clinical purposes may be a human protein, e.g. CD19, CD20, EGFR, truncated NGFR, and the like.

Specific compositions are provided of genetic sequences encoding safety switches. Examples of constructs are provided in FIG. 2C, FIG. 4B, and FIG. 6B. The genetic construct comprises the coding sequence for the switch protein, which is optionally flanked by self-cleaving peptide sequences. Optionally, downstream of the switch protein and self-cleaving peptide sequence, a selectable marker sequence may be present. High efficiency engineering systems may not require a selectable marker. The genetic construct may comprise homologous sequences for recombination at the target locus. The safety switch genetic sequence may be provided in a viral vector suitable for integration. In some embodiments the viral vector is an AAV vector, e.g. any one of the AAV serotypes AAV1, AAV2, AAV3, AAV4, AAV5, AAV6, AAV7, AAV8, AAV9, AAV10, AAV11, etc. In some embodiments the vector is AAV6.

By "pluripotency" and pluripotent stem cells it is meant that such cells have the ability to differentiate into all types of cells in an organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of experimental manipulation could not give rise to all types of cells in the organism. iPS cells have an hESC-like morphology, growing as flat colonies with large nucleo-cytoplasmic ratios, defined borders and prominent nuclei. In addition, iPS cells express one or more key pluripotency markers known by one of ordinary skill in the art, including but not limited to alkaline phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPS cells are capable of forming teratomas. In addition, they are capable of forming or contributing to ectoderm, mesoderm, or endoderm tissues in a living organism.

A "starting cell population", or "initial cell population" refers to a somatic cell, usually a primary, or non-transformed, somatic cell, which undergoes nuclear reprogramming to pluripotency. The starting cell population may be of any mammalian species, but particularly including human cells. Sources of starting cell populations include individuals desirous of cellular therapy, individuals having a genetic defect of interest for study, and the like. Somatic cells can be contacted with reprogramming factors in a combination and quantity sufficient to reprogram the cell to pluripotency.

Genes may be introduced into pluripotent cells for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

The cells may be differentiated to adopt a specific cell fate and used for reconstituting or supplementing differentiating or differentiated cells in a recipient. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more: pancreatic beta cells, neural stem cells, neurons (e.g., dopaminergic neurons), oligodendrocytes, oligodendrocyte progenitor cells, hepatocytes, hepatic stem cells, chondrocytes, bone cells, connective tissue cells, astrocytes, myocytes, hematopoietic cells, or cardiomyocytes.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

Methods of Engineering Pluripotent Cells with Safety Switches

Methods are provided for engineering a safety switch or multiple safety switches into a cell. A cell, usually a pluripotent cell, is contacted with an RNA guided endonuclease effector protein and guide RNA for insertion into the target locus. In class 2 CRISPR systems, the functions of the effector complex (e.g., the cleavage of target DNA) are carried out by a single protein (which can be referred to as a CRISPR/Cas effector protein). For example, type II CRISPR/Cas proteins (e.g., Cas9), type V CRISPR/Cas proteins (e.g., Cpf1/Cas12a, C2c1/Cas12b, C2C3/Cas12c), and type VI CRISPR/Cas proteins (e.g., C2c2/Cas13a, C2C7/Cas13c, C2c6/Cas13b). Class 2 CRISPR/Cas effector proteins include type II, type V, and type VI CRISPR/Cas proteins.

In some cases, an RNA-guided endonuclease is a fusion protein that is fused to a heterologous polypeptide (also referred to as a "fusion partner"). In some cases, an RNA-guided endonuclease is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.). An RNA-guided endonuclease (e.g., a Cas9 protein) can have multiple (1 or more, 2 or more, 3 or more, etc.) fusion partners in any combination of the above.

A nucleic acid that binds to a class 2 CRISPR/Cas effector protein (e.g., a Cas9 protein; a type V or type VI CRISPR/Cas protein; a Cpf1 protein; etc.) and targets the complex to a specific location within a target nucleic acid is referred to as a guide RNA. A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

A wild type CRISPR/Cas effector protein (e.g., Cas9 protein) normally has nuclease activity that cleaves a target nucleic acid (e.g., a double stranded DNA (dsDNA)) at a target site defined by the region of complementarity between the guide sequence of the guide RNA and the target nucleic acid. In some cases, site-specific targeting to the target nucleic acid occurs at locations determined by both (i) base-pairing complementarity between the guide nucleic acid and the target nucleic acid; and (ii) a short motif referred to as the "protospacer adjacent motif" (PAM) in the target nucleic acid. For example, when a Cas9 protein binds to (in some cases cleaves) a dsDNA target nucleic acid, the PAM sequence that is recognized (bound) by the Cas9 polypeptide is present on the non-complementary strand (the strand that does not hybridize with the targeting segment of the guide nucleic acid) of the target DNA.

For additional information related to programmable gene editing tools (e.g., CRISPR/Cas RNA-guided proteins such as Cas9, CasX, CasY, and Cpf1, Zinc finger proteins such as Zinc finger nucleases, TALE proteins such as TALENs, CRISPR/Cas guide RNAs, PAMs, and the like) refer to, for example, Dreier, et al., (2001) J Biol Chem 276:29466-78; Dreier, et al., (2000) J Mol Biol 303:489-502; Liu, et al., (2002) J Biol Chem 277:3850-6); Dreier, et al., (2005) J Biol Chem 280:35588-97; Jamieson, et al., (2003) Nature Rev Drug Discov 2:361-8; Durai, et al., (2005) Nucleic Acids Res 33:5978-90; Segal, (2002) Methods 26:76-83; Porteus and Carroll, (2005) Nat Biotechnol 23:967-73; Pabo, et al., (2001) Ann Rev Biochem 70:313-40; Wolfe, et al., (2000)

Ann Rev Biophys Biomol Struct 29:183-212; Segal and Barbas, (2001) Curr Opin Biotechnol 12:632-7; Segal, et al., (2003) Biochemistry 42:2137-48; Beerli and Barbas, (2002) Nat Biotechnol 20:135-41; Carroll, et al., (2006) Nature Protocols 1:1329; Ordiz, et al., (2002) Proc Natl Acad Sci USA 99:13290-5; Guan, et al., (2002) Proc Natl Acad Sci USA 99:13296-301; Sanjana et al., Nature Protocols, 7:171-192 (2012); Zetsche et al, Cell. 2015 Oct. 22; 163(3):759-71; Makarova et al, Nat Rev Microbiol. 2015 November; 13(11):722-36; Shmakov et al., Mol Cell. 2015 Nov. 5; 60(3):385-97; Jinek et al., Science. 2012 Aug. 17; 337 (6096):816-21; Chylinski et al., RNA Biol. 2013 May; 10(5):726-37; Ma et al., Biomed Res Int. 2013; 2013: 270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10): 1163-71; Cho et. al., Genetics. 2013 November; 195(3): 1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. al., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; Briner et al., Mol Cell. 2014 Oct. 23; 56(2): 333-9; Burstein et al., Nature. 2016 Dec. 22—Epub ahead of print; Gao et al., Nat Biotechnol. 2016 July 34(7):768-73; Shmakov et al., Nat Rev Microbiol. 2017 March; 15(3):169-182; as well as international patent application publication Nos. WO2002099084; WO00/42219; WO02/42459; WO2003062455; WO03/080809; WO05/014791; WO05/084190; WO08/021207; WO09/042186; WO09/054985; and WO10/065123; U.S. patent application publication Nos. 20030059767, 20030108880, 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; 20140377868; 20150166983; and 20160208243; and U.S. Pat. Nos. 6,140,466; 6,511,808; 6,453,242 8,685,737; 8,906,616; 8,895,308; 8,889,418; 8,889,356; 8,871,445; 8,865,406; 8,795,965; 8,771,945; and 8,697,359; all of which are hereby incorporated by reference in their entirety.

In some embodiments the Cas9 is provided as a ribonucleoprotein complex with sgRNA, which is electroporated into the cell. The cell is then contacted with the vector comprising the safety switch. Depending on the efficiency of the process, the cells can be selected for the presence of the safety switch. Cells can be produced and grown under GMP conditions for use in human therapy, and may be banked for further use.

In one embodiment of the invention, methods are provided for depletion of pluripotent cells from a mixed population of differentiated cells and stem cells, to provide a population of cells substantially free of pluripotent stem cells. The population of cells depleted by the methods described herein are substantially free of pluripotent stem cells. By substantially free of pluripotent cells, it is intended that less than 1 in $10^7$ cells have the properties of a pluripotent cell, as described herein, usually less than 1 in $10^8$, more usually less than 1 in $10^9$, and preferably less than 1 in $10^{10}$.

Generally, therapeutic cells are differentiated from the initial pluripotent population to a desired differentiated cell type. Following differentiation, the cells are contacted with an effective dose of the orthologous activating agent for the selective switch, for a period of from about 12, about 24, about 36, about 48 hours, to cause a greater than $10^6$-fold reduction in the number of pluripotent cells in the population, while leaving viable differentiated cells.

Compositions depleted of pluripotent cells are achieved in this manner. The depleted cell population or an engineered cell population with one or more safety switches may be used immediately. Alternatively, the cell population may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cells.

In one embodiment of the invention, methods are provided for depletion of engineered cells that may be differentiated or may be pluripotent. Following transfer of the engineered cells to a subject, there may be cause to generally deplete the engineered cells, e.g. if the cells show excess proliferation, are the cause of undesirable immune responses, and the like. In such cases, the orthologous activating agent for the general switch is provided to the subject in a dose effective to deplete the engineered cells.

In some embodiments a therapeutic method is provided, the method comprising introducing into a recipient in need thereof of an engineered cell population, wherein the cell population has been modified by introduction of a sequence encoding a safety switch. The cell population may be engineered ex vivo, and is usually autologous or allogeneic with respect to the recipient.

Engineered cells can be provided in pharmaceutical compositions suitable for therapeutic use, e.g. for human treatment. Therapeutic formulations comprising such cells can be frozen, or prepared for administration with physiologically acceptable carriers, excipients or stabilizers (Remington's Pharmaceutical Sciences 16th edition, Osol, A. Ed. (1980)), in the form of aqueous solutions. The cells will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The cells can be administered by any suitable means, usually parenteral. Parenteral infusions include intramuscular, intravenous (bolus or slow infusion), intraarterial, intraperitoneal, intrathecal or subcutaneous administration.

The engineered cells may be infused to the subject in any physiologically acceptable medium, normally intravascularly, although they may also be introduced into any other convenient site, where the cells may find an appropriate site for growth. Usually, at least $1\times10^6$ cells/kg will be administered, at least $1\times10^7$ cells/kg, at least $1\times10^8$ cells/kg, at least $1\times10^9$ cells/kg, at least $1\times10^{10}$ cells/kg, or more.

A course of therapy may be a single dose or in multiple doses over a period of time. In some embodiments, the cells are administered in a single dose. In some embodiments, the cells are administered in two or more split doses administered over a period of 1, 2, 3, 4, 5, 6, 7, 8, 9, 10, 11, 12, 13, 14, 21, 28, 30, 60, 90, 120 or 180 days. The quantity of engineered cells administered in such split dosing protocols may be the same in each administration or may be provided at different levels. Multi-day dosing protocols over time periods may be provided by the skilled artisan (e.g. physician) monitoring the administration of the cells taking into account the response of the subject to the treatment including adverse effects of the treatment and their modulation as discussed above.

The preferred formulation depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Formulations to be used for in vivo administration are typically sterile. Sterilization of the compositions of the present invention may readily accomplished by filtration through sterile filtration membranes.

Also provided are kits for use in the methods. A kit will comprise a vector encoding at least one, and preferably two different safety switches. A kit may further comprise agents for precise genetic recombination, e.g. a cas9 protein and suitable guide RNAs for a locus of interest, including without limitation NANOG, ACTB, etc. Kits may further comprise orthologous activating agents, e.g. acyclovir or ganciclovir; AP20, AP21, etc.

In some embodiments, the components are provided in a dosage form (e.g., a therapeutically effective dosage form), in liquid or solid form in any convenient packaging (e.g., stick pack, dose pack, etc.). Reagents for the selection or in vitro derivation of cells may also be provided, e.g. growth factors, differentiation agents, tissue culture reagents; and the like.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Genome Edited Orthogonal Safeguards to Improve the Safety of Human Pluripotent Stem Cell-Based Therapies Human pluripotent stem cell (hPSC)-derived cell therapies, despite their therapeutic promise, continue to have serious safety risks. Teratomas (which arise from undifferentiated hPSCs) and the uncontrolled growth of transplanted hPSC-derived cells have both been observed in preclinical models. Mitigating these risks is important to increase the safety of such therapies. We use genome editing to engineer a general platform to improve the safety of future hPSC-derived cell transplantation therapies. Specifically, we developed hPSC lines bearing two drug-inducible safeguards: administration of one small molecule depletes undifferentiated hPSCs>$10^5$-fold (thus preventing teratoma formation in vivo), whereas administration of a second small molecule reverses the overgrowth of transplanted hPSC-derived cells in vivo. These orthogonal safety switches address two major safety concerns with pluripotent cell-derived therapies.

To mitigate both of these safety risks for hPSC-based cell therapies, we developed orthogonal systems to selectively kill undifferentiated hPSCs and to efficiently eliminate the entire cell product if necessary (FIG. 1). These genetically-encoded, safety systems enable us to ablate desired hPSC-derived cell-types upon small molecule administration both in vitro and in vivo.

Results

Figure 2:
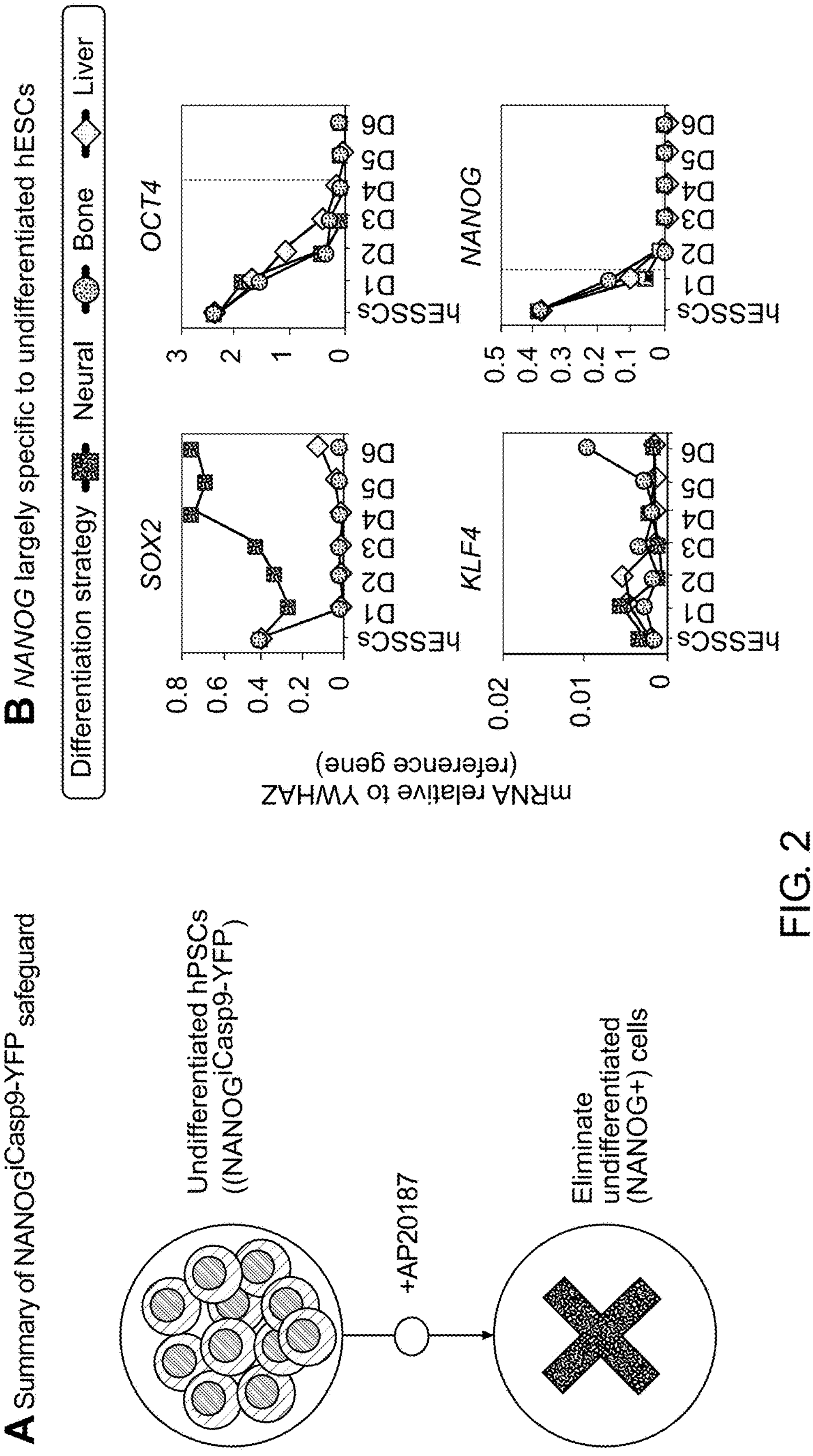
FIG. 2: Rationale and design of the NANOG$^{iCasp9\text{-}YFP}$ safety switch. A) Intended application of the NANOG$^{iCasp9\text{-}YFP}$ safeguard. B) Quantitative PCR (qPCR) of pluripotency transcription factor expression during differentiation into endodermal, mesodermal and ectodermal lineages. Dotted line indicates when gene expression declined below 10% of YWHAZ in all three differentiation systems. Expression of lineage markers is depicted normalized to the reference gene YWHAZ (i.e., YWHAZ=1.0). C) Cas9 RNP/AAV6-based strategy for NANOG$^{iCasp9\text{-}YFP}$ targeting. D) YFP expression levels in NANOG$^{iCasp9\text{-}YFP}$ hESCs as shown by epifluorescence (left) and flow cytometry (right), relative to wild-type hESCs. E) Flow cytometric analysis of YFP during differentiation of NANOG$^{iCasp9\text{-}YFP}$ hESCs into endodermal, mesodermal or ectodermal lineages. Dotted line delineates negative vs. positive cells set based on YFP levels in undifferentiated NANOG$^{iCasp9\text{-}YFP}$ hESCs.
Figure 2:
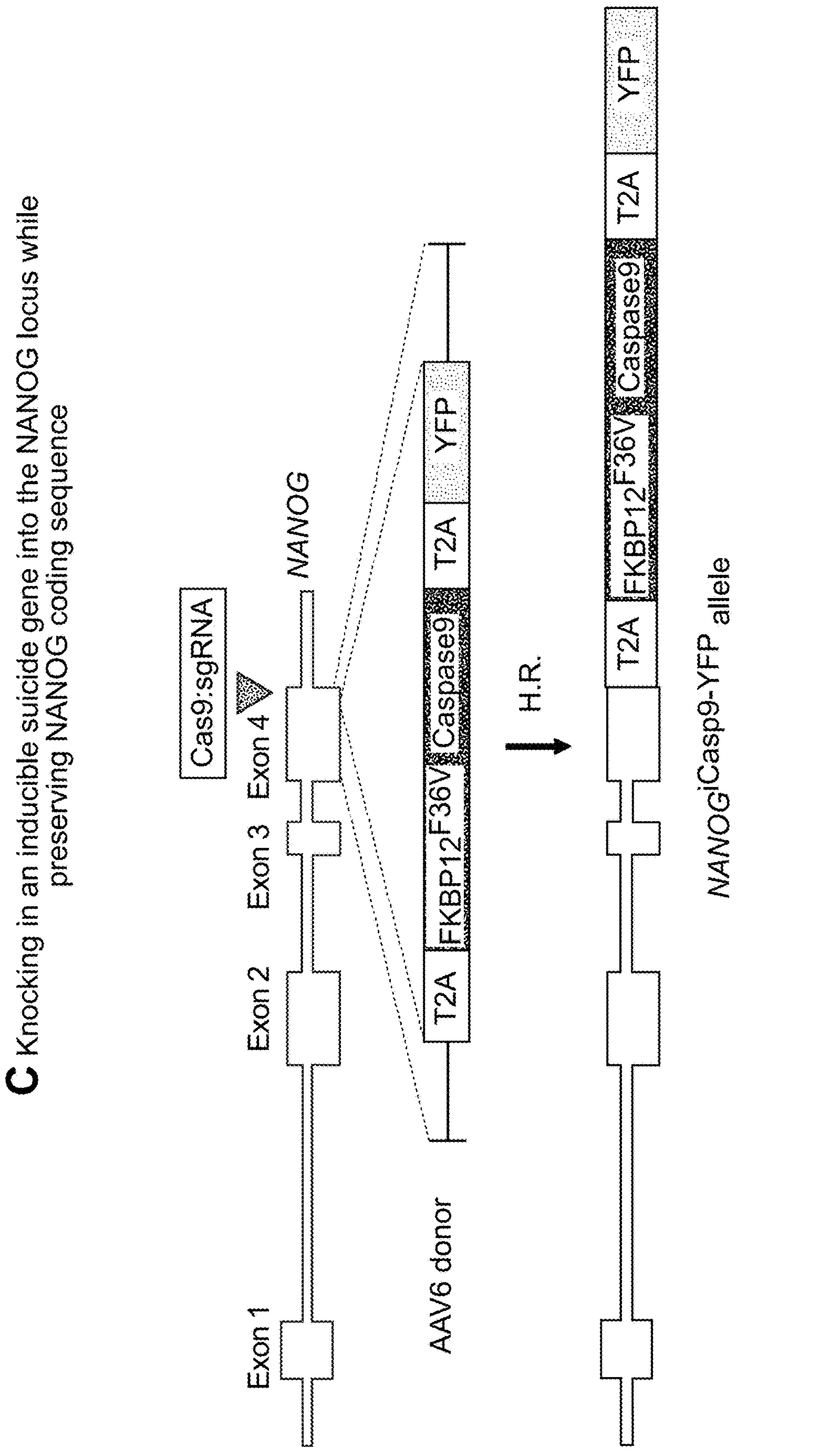
Figure 2:
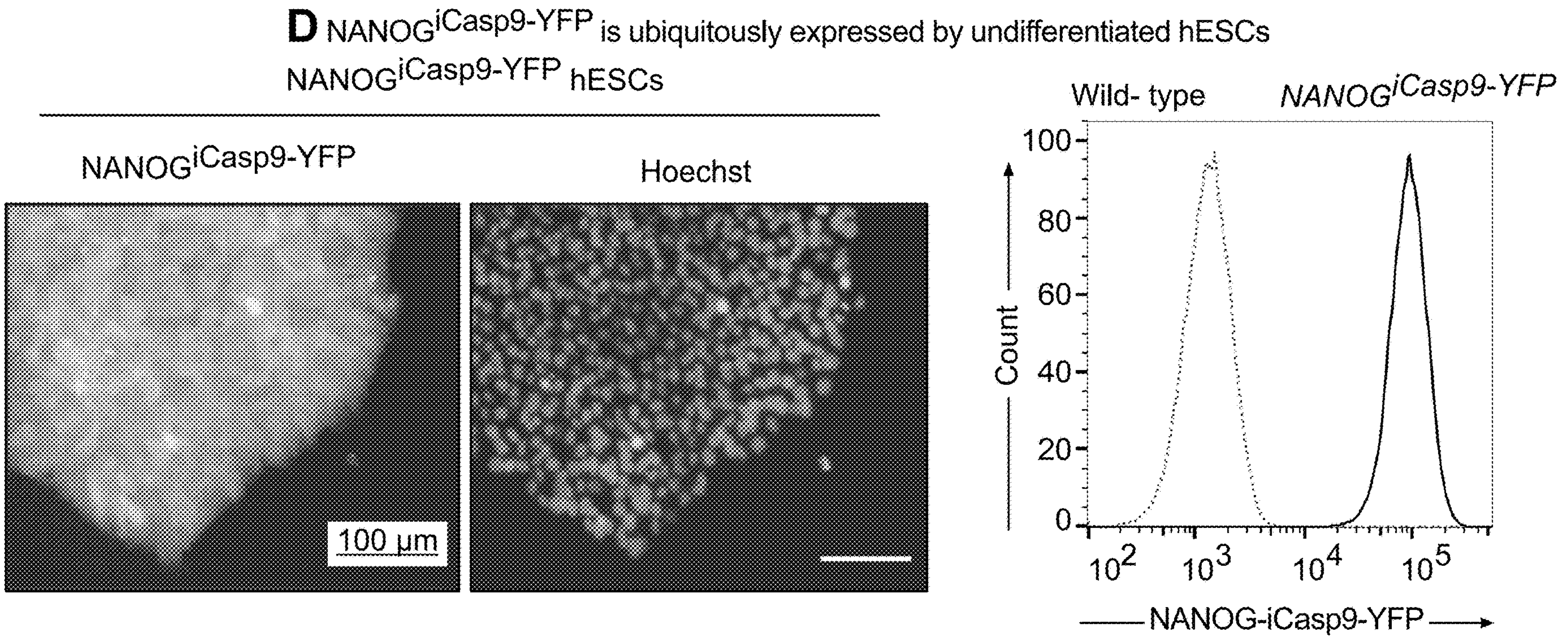
Figure 2:
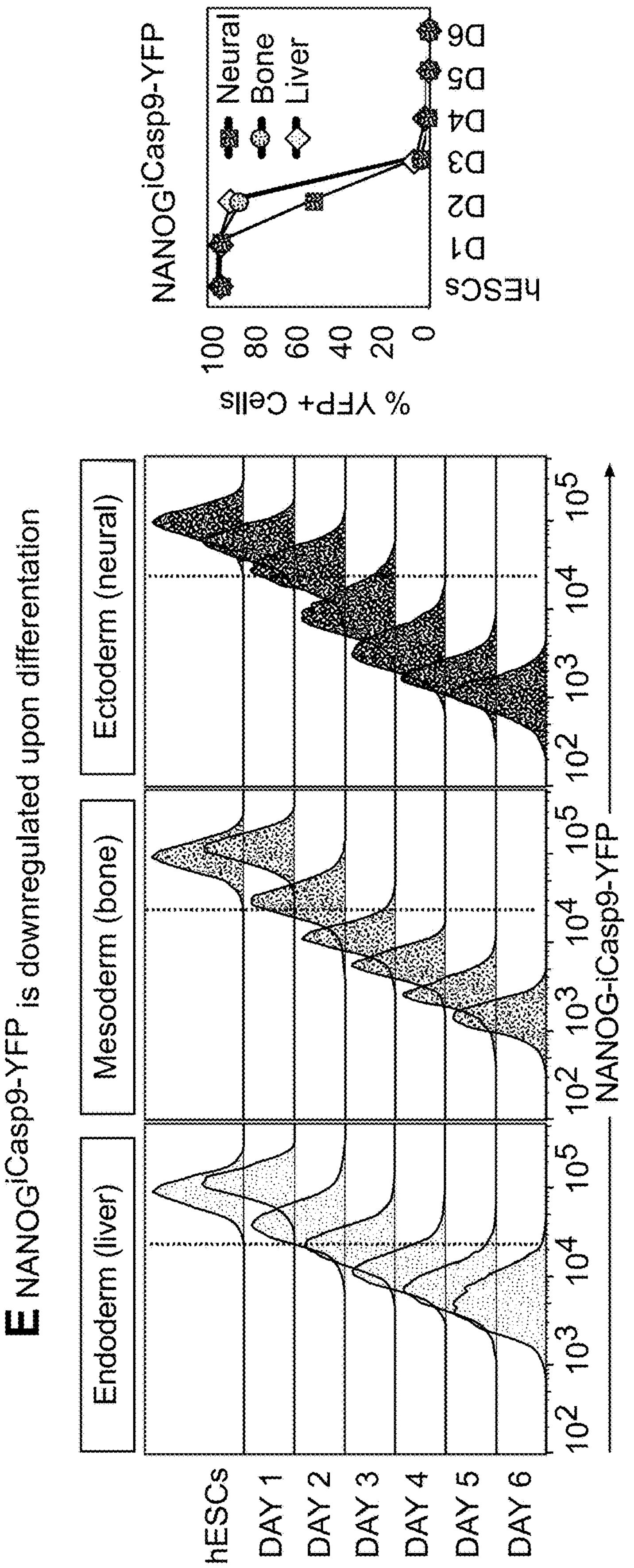
Figure 7:
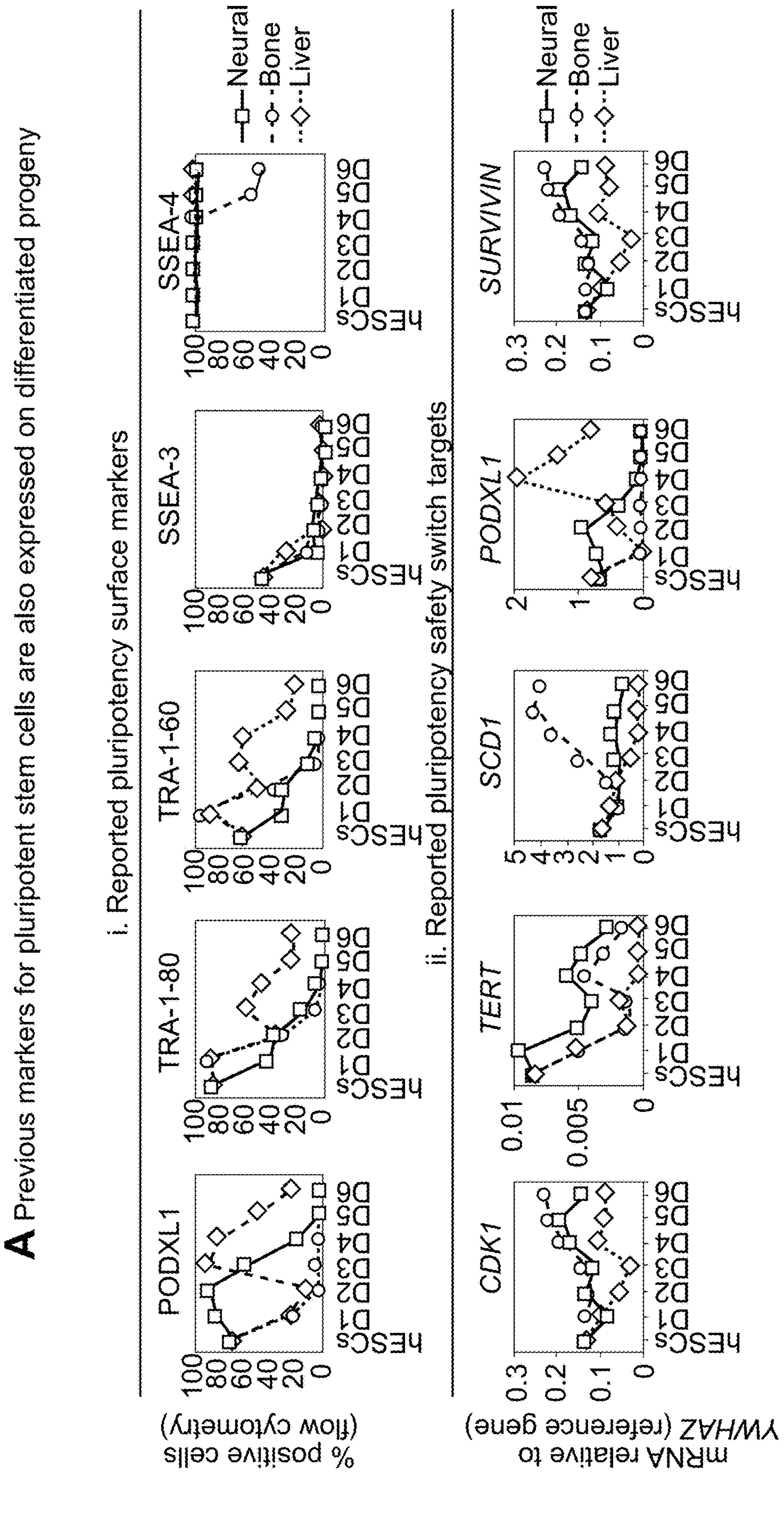
FIG. 7: Marker expression during hPSC differentiation and evaluation of past safety switches (related to FIG. 2). A) i) Flow cytometry analysis of widely-used pluripotency surface markers SSEA-3, SSEA-4, TRA-1-60, TRA-1-81 and PODXL1[20,21] before and during differentiation into endodermal, mesodermal and ectodermal lineages for 1-6 days. Positive gates were set based on unstained negative controls. ii) Gene expression analysis of previously reported safety system genes CDK1, TERT, SCD1, PODXL1 and SURVIVIN before and during differentiation into endodermal, mesodermal and ectodermal lineages. Expression of lineage markers is depicted normalized to the reference gene YWHAZ (i.e., YWHAZ=1.0). B) Widely-used pluripotency surface markers such as SSEA-3, SSEA-4, TRA-1-60, TRA-1-81 and PODXL1[20,21] were not exclusive to pluripotent cells. Flow cytometry analysis of undifferentiated hESCs and upon 1-6 days of differentiation into endodermal, mesodermal or ectodermal lineages revealed that these surface markers were expressed in both undifferentiated and differentiated cell-types. Unstained hESCs (top row; grey shading) were used as a negative control to set positive gates (dotted vertical lines). C) Endodermal, mesodermal and ectodermal differentiation protocols used in this study were validated by assessing expression of lineage-specific markers during differentiation into each of these respective cell-types. qPCR was performed on wild-type H9 hESCs (grey line) or NANOG$^{iCasp9-YFP}$;ACTB$^{TK-mPlum}$ hPSCs (black line) in the undifferentiated state or upon 1-6 days of differentiation into endodermal, mesodermal or ectodermal lineages. This analysis also revealed that genetic targeting of the NANOG and ACTB loci did not significantly perturb differentiation into these 3 cell-types. Expression of lineage markers is depicted normalized to the reference gene YWHAZ(i.e., YWHAZ=1.0), with y-axis expression values depicted in $\log_{10}$. D) H9 undifferentiated hPSCs and hPSC-derived neural, liver, and sclerotome cells (generated after 6 days of differentiation) were treated for 24 hours with YM155 (either 10 nM or 2 μM), a small molecule SURVIVIN inhibitor, and cell viability was assessed using alamar blue.
Figure 7:
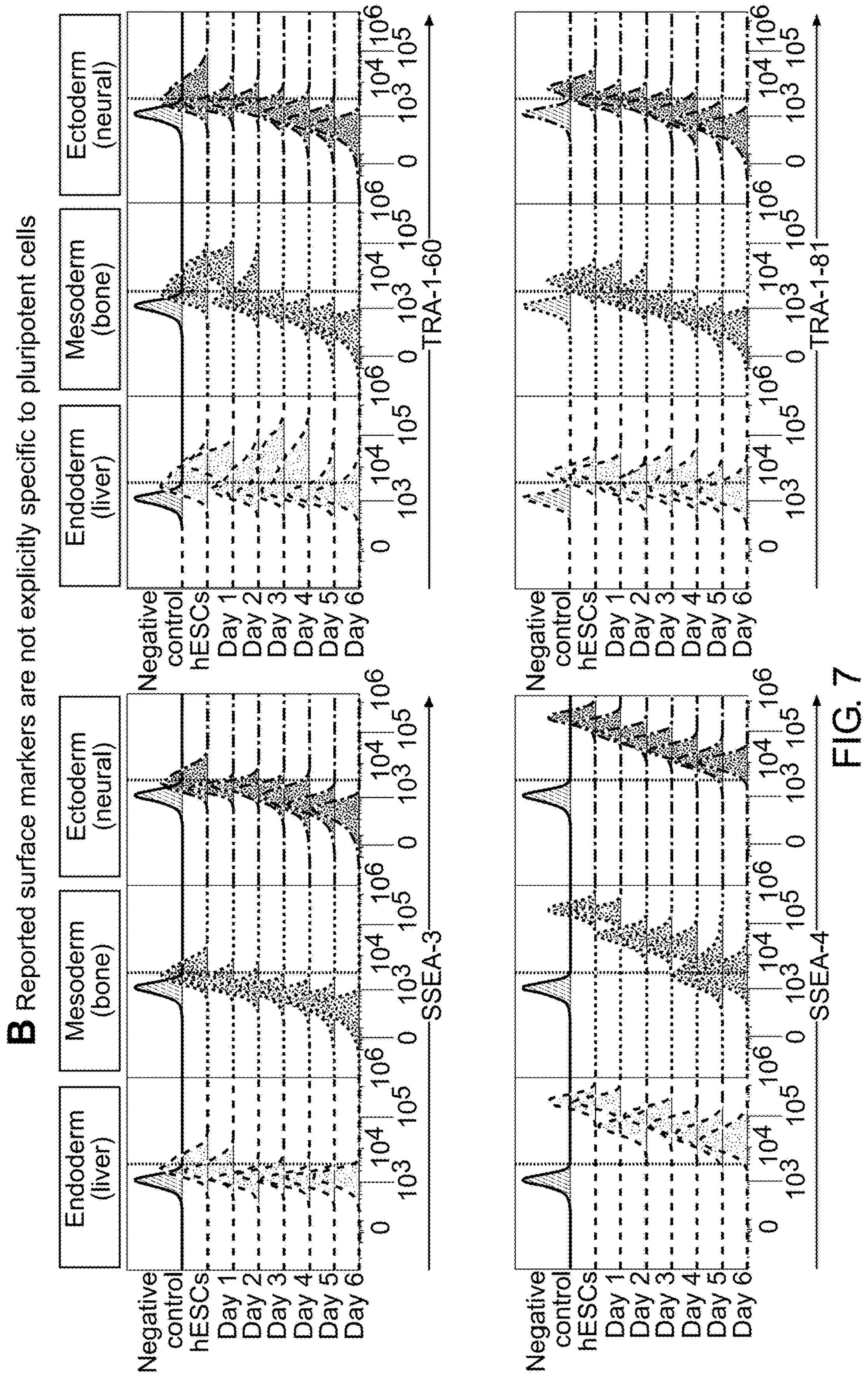
Figure 7:
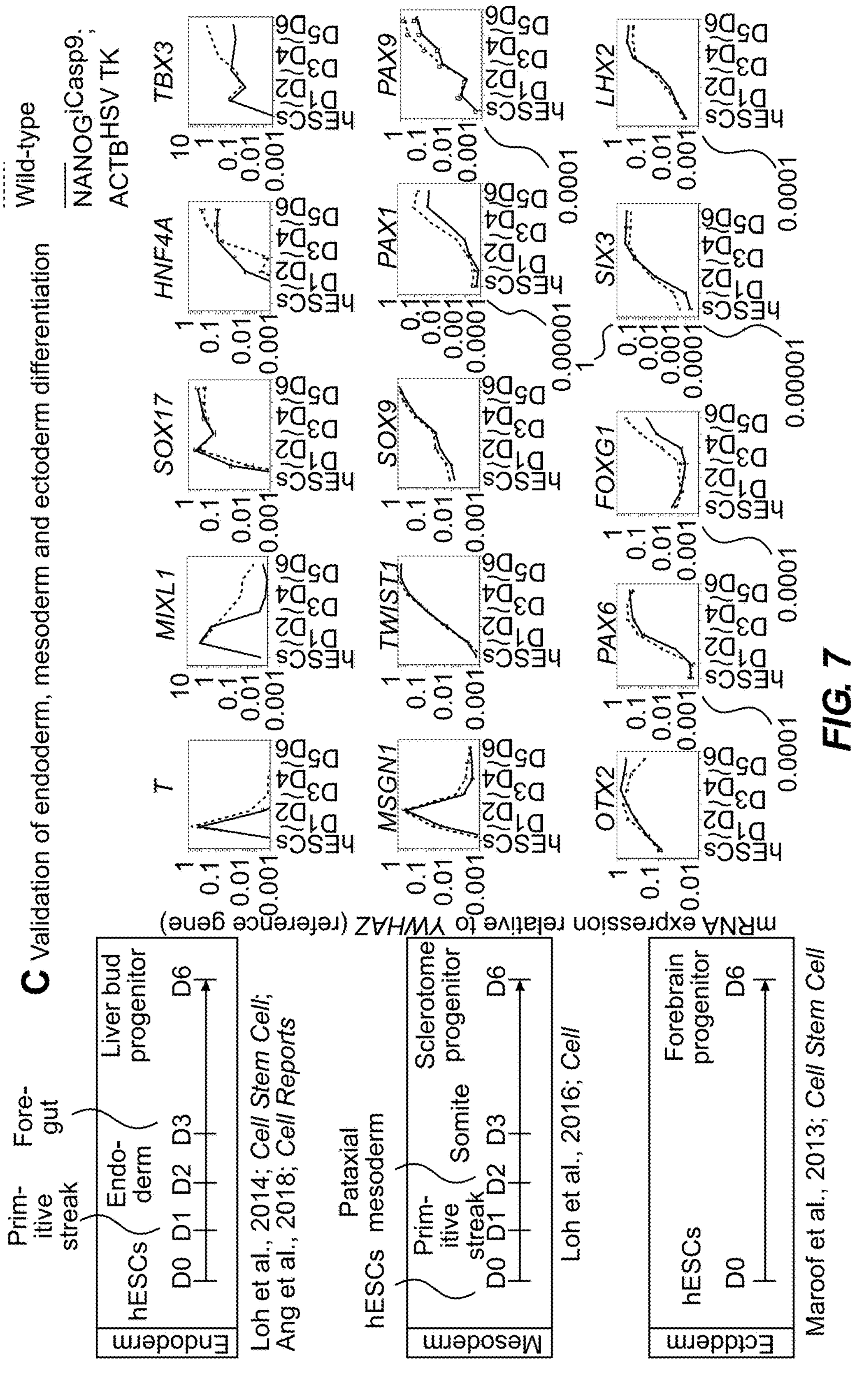

NANOG$^{iCaspase9}$ system to specifically eliminate undifferentiated hPSCs. We addressed the safety concern that trace numbers of undifferentiated hPSCs can form teratomas in vivo (FIGS. 1 and 2*a*). Others have described surface markers that identify undifferentiated hPSCs (e.g., SSEA-3, SSEA-4, TRA-1-60, TRA-1-81 and PODXL1) as well as genetic kill-switches (based on expression of the CDK1, TERT, SCD1, and SURVIVIN/BIRC5 genes) to kill such cells. However, the efficacy of all such systems depend on whether these marker genes are specific to pluripotent cells. We found that all of these previously-reported markers were expressed by undifferentiated hPSCs as well as by cells that had been differentiated into endoderm (liver progenitors), mesoderm (bone progenitors), and ectoderm (forebrain progenitors) (FIG. 7*a-c*). Hence, previous marker-based strategies to deplete pluripotent cells are not specific and would also deplete the therapeutic product consisting of differentiated cells. Indeed the previously-described SURVIVIN inhibitor YM155 killed both undifferentiated and differentiated hPSCs (FIG. 7*d*), consistent with broad expression of SURVIVIN across undifferentiated and differentiated hPSCs (FIG. 7*a*). This emphasizes the importance of selectively depleting undifferentiated hPSCs to create a safe differentiated cell product that could then be safely transplanted with a significantly decreased risk of teratoma formation.

We assayed the expression of multiple pluripotency transcription factors and found that NANOG was the most specific to the pluripotent state (FIG. 2*b*). It was expressed by undifferentiated hPSCs but was sharply downregulated within 24 hours of ectoderm differentiation and within 48 hours of endoderm or mesoderm differentiation (FIG. 2*b*). We therefore developed a specific and simple system to track whether cells were in a pluripotent state (NANOG$^+$) and to link this to controllable elimination of such cells via apoptosis.

Figure 8:
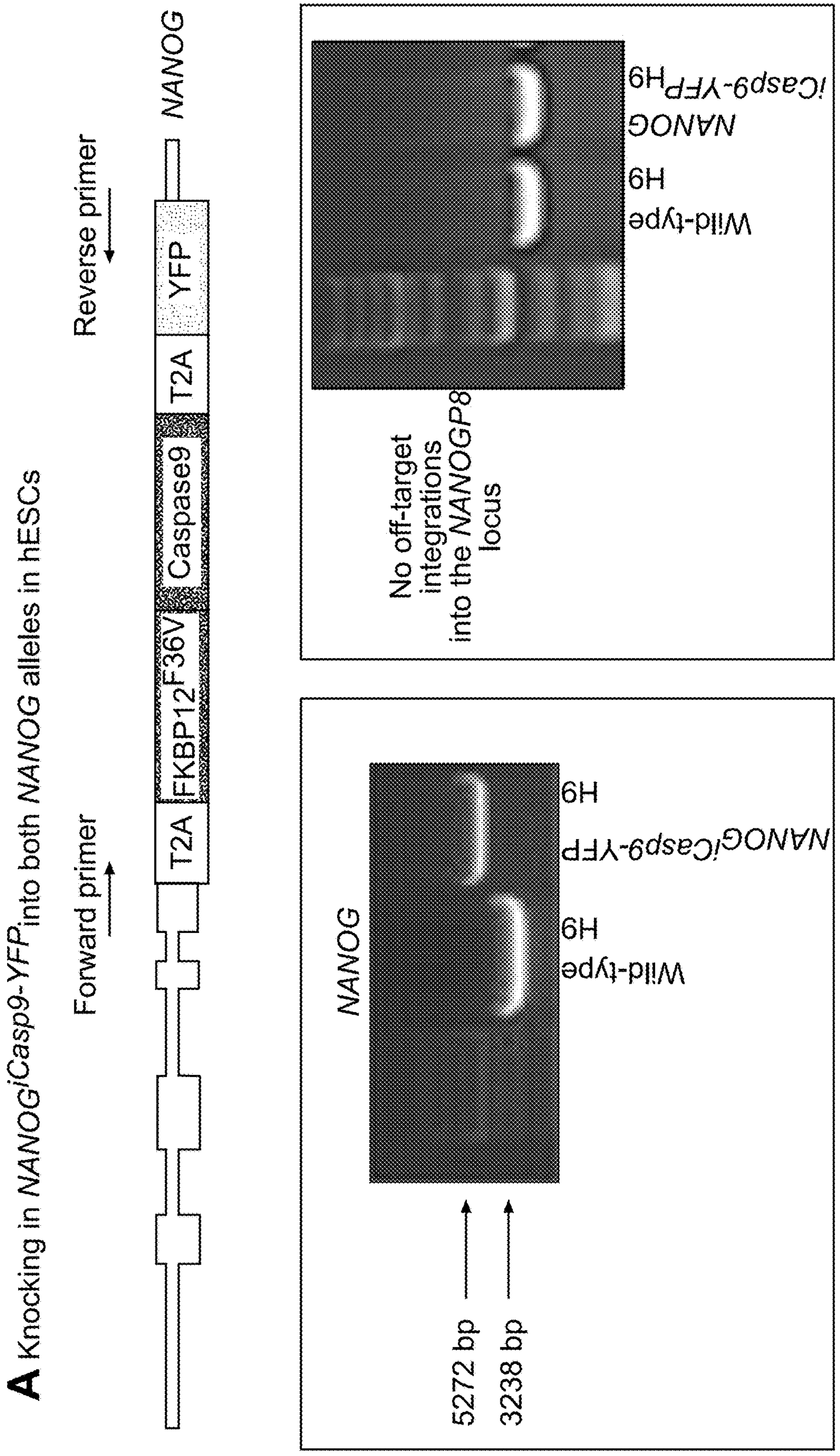
FIG. 8: Construction of the NANOG$^{iCasp9-YFP}$ safety switch (related to FIG. 2). A) Schema of targeted NANOG$^{iCasp9-YFP}$ allele (see FIG. 2*c*), with forward and reverse primers used for genotyping indicated (top). Genomic PCR revealed biallelic targeting of the NANOG locus (left), with no off-target integrations into the related NANOGP8 locus (right inset). B) NANOG$^{iCasp9-YFP}$; ACTB$^{TK-mPlum}$NANOG$^{iCasp9-YFP}$ hPSCs were still pluripotent. They uniformly expressed SOX2 and NANOG at both the protein level (immunostaining; left) and mRNA level (qPCR; right). For immunostaining, DAPI was used for nuclear counterstaining. For qPCR, wild-type hPSCs were used as a positive control, and expression of marker genes is depicted normalized to the reference gene YWHAZ(i.e., YWHAZ=1.0). C) In NANOG$^{iCasp9-YFP}$ hPSCs, SOX2 and NANOG proteins were still expressed at the normal levels found in wild-type hESCs, as shown by intracellular flow cytometry. Isotype controls (grey) were used to set positive gates. D) NANOG$^{iCasp9-YFP}$;ACTB$^{TK-mPlum}$ hPSCs were karyotypically normal (9 passages after initial NANOG$^{iCasp9-YFP}$ targeting). E) qPCR of NANOG$^{iCasp9-YFP}$ hPSCs differentiating into endodermal, mesodermal or ectodermal cell-types (differentiation protocols described in FIG. S1*c*) shows that expression of iCaspase9 (FKBP-Casp9) mRNA and endogenous NANOG mRNA is similar in both hESCs and differentiated cell-types, consistent with how they are transcriptionally linked in the NANOG$^{iCasp9-YFP}$ allele. Expression of marker genes is depicted normalized to the reference gene YWHAZ (i.e., YWHAZ=1.0). F) Despite short-term (passage 9) or long-term (passage 36) culture, the NANOG$^{iCasp9-YFP}$ allele was constitutively expressed in undifferentiated NANOG$^{iCasp9-YFP}$ hPSCs, as shown by flow cytometry. (Passages refer to the time when the NANOG$^{iCasp9-YFP}$ allele was first introduced into hPSCs.)
Figure 8:
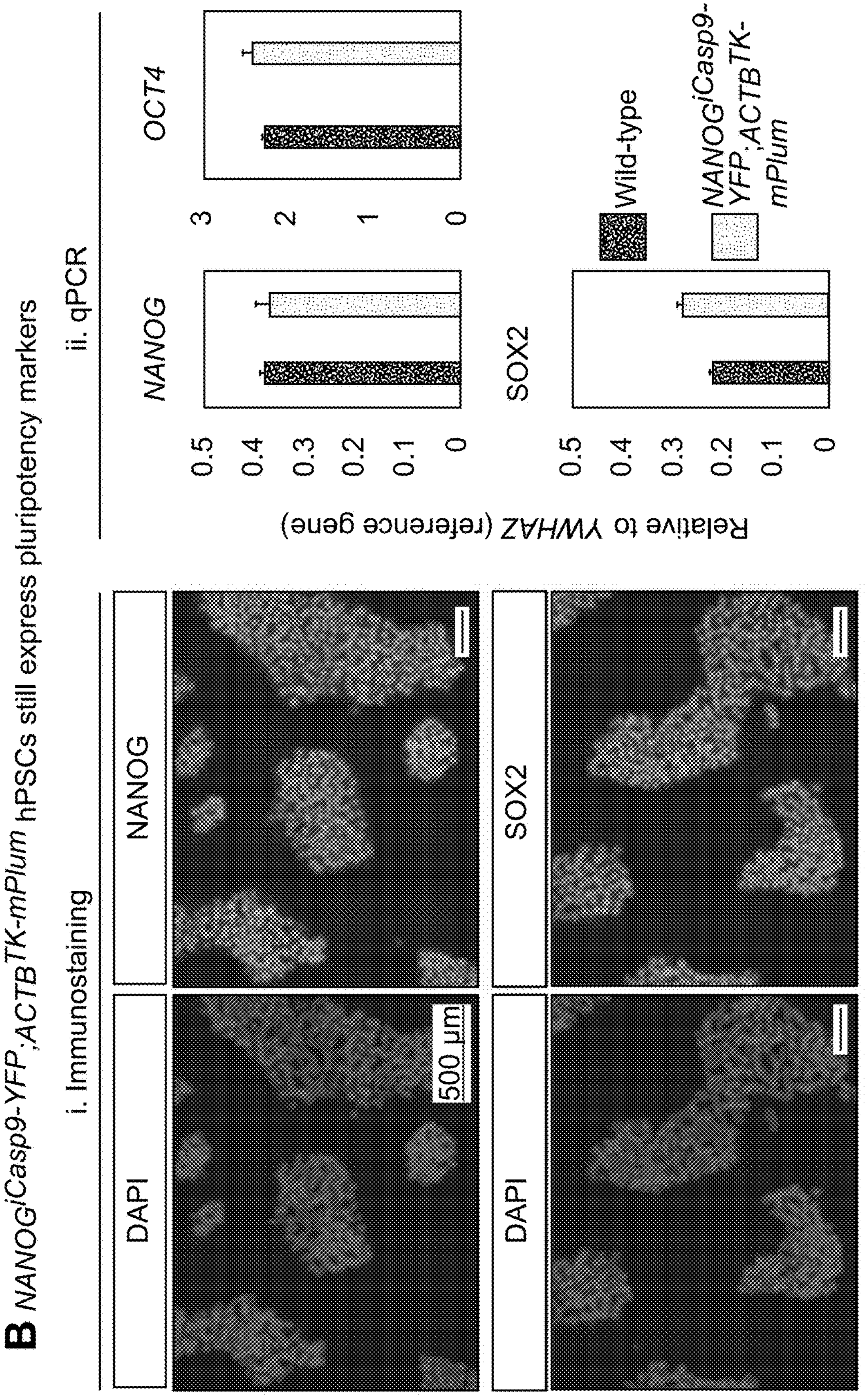
Figure 8:
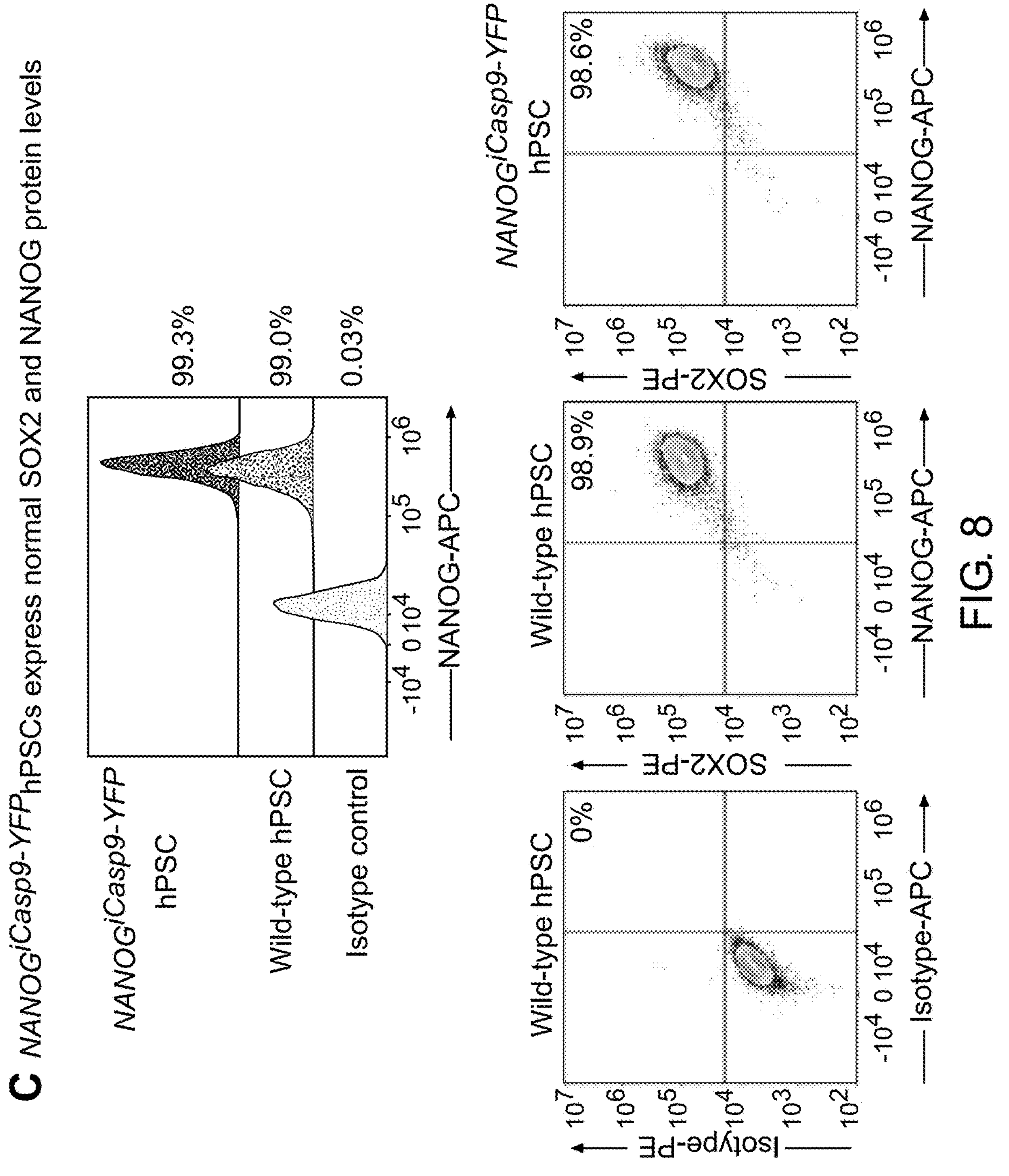
Figure 8:
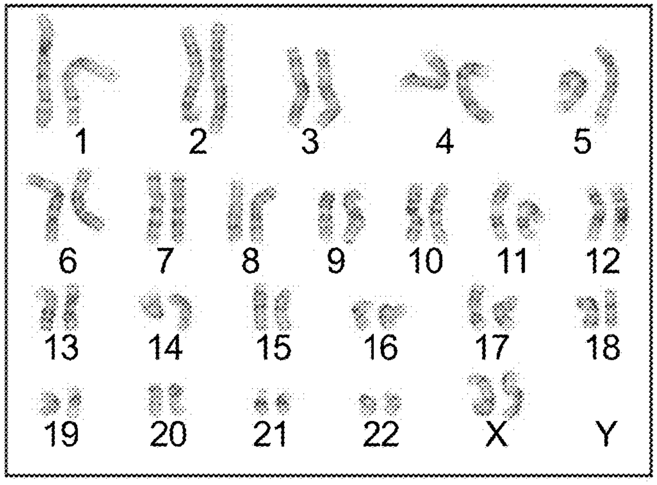
Figure 8:
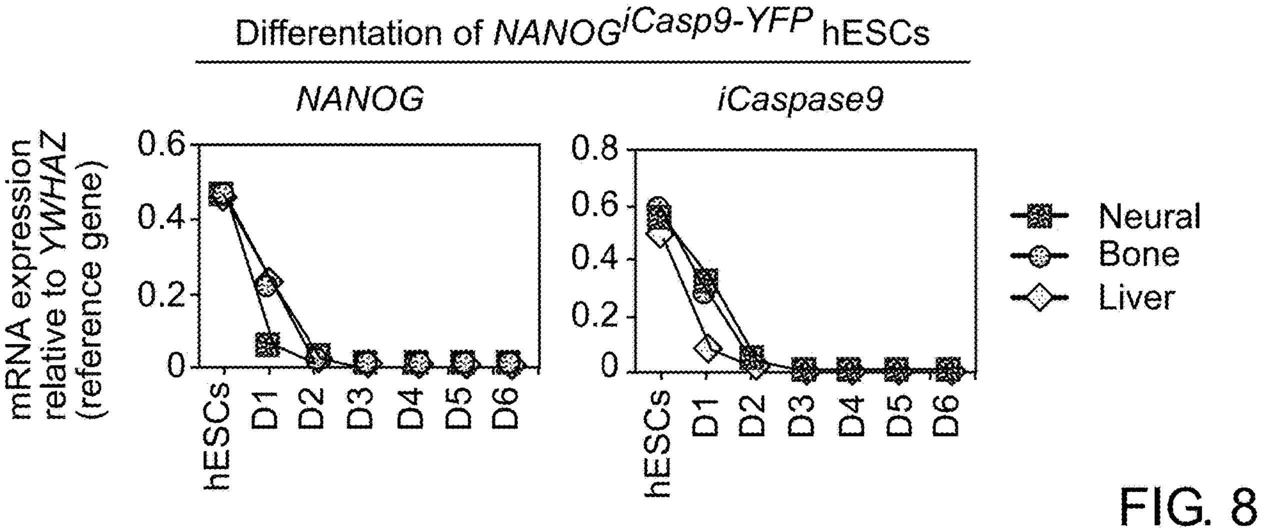
Figure 8:
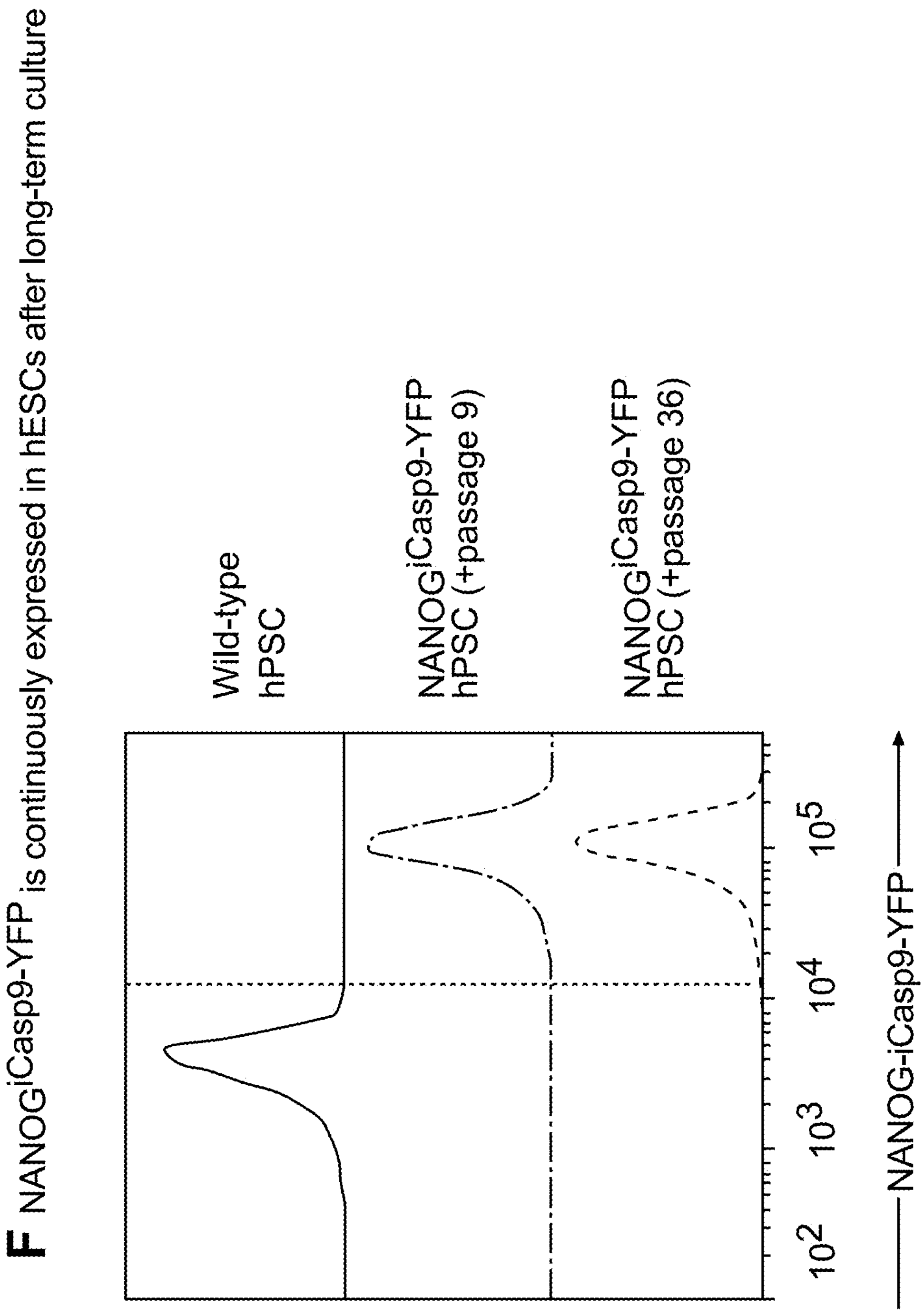

We exploited Cas9 RNP (ribonucleoprotein)/AAV6-based genome editing to knock-in an inducible Caspase9 (iCaspase9) cassette and a fluorescent reporter (YFP) into the NANOG locus (FIG. 2*c*, FIG. 8*a*), while leaving the NANOG coding sequence intact, as NANOG is critical to maintain undifferentiated hPSCs. iCaspase9 encodes a Caspase9-FKBP$^{F36V}$ fusion protein that, after dimerization with the small molecule AP20187 (hereafter called "AP20"), induces cell-intrinsic, rapid and irreversible apoptosis. We inserted this iCaspase9-YFP gene cassette into both NANOG alleles to prevent the emergence of "escape" cells (e.g., if a pluripotent cell stochastically used only one allele of NANOG to support its growth). Genomic sequencing confirmed successful biallelic targeting of the NANOG locus, without off-target integration into the NANOGP8 pseudogene (FIG. 8*a*). NANOG$^{iCasp9\text{-}YFP}$ hPSCs maintained normal pluripotency marker expression (FIG. 8*b*), karyotype (FIG. S2*c*) and the ability to differentiate into endoderm, mesoderm and ectoderm cells (FIG. 7*c*). Finally, the NANOG$^{iCasp9\text{-}YFP}$ allele faithfully paralleled endogenous NANOG expression: YFP and iCaspase9 mRNA were uniformly expressed by undifferentiated NANOG$^{iCasp9\text{-}YFP}$hPSCs, but both were extinguished upon endoderm, mesoderm or ectoderm differentiation (FIG. 2*d,e*; FIG. 8*d*). After successfully engineering the cells, we tested whether the NANOG$^{iCasp9\text{-}YFP}$ system could specifically ablate undifferentiated hPSCs without eliminating differentiated cells (the potential therapeutic cell product).

Figure 3:
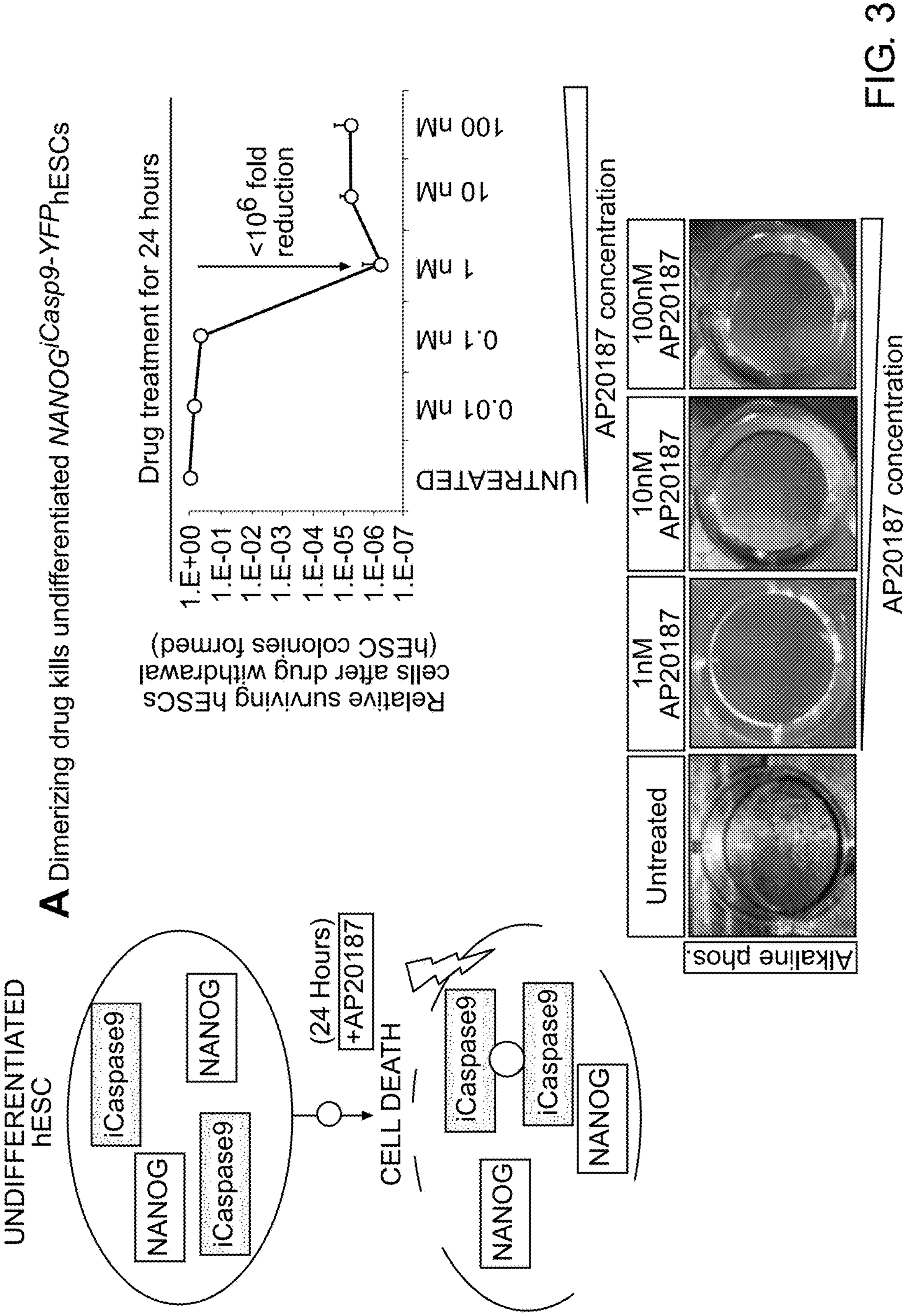
FIG. 3: Implementation of the NANOG$^{iCasp9\text{-}YFP}$ safety switch. A) Schema depicting how drug AP20187 induces dimerization of Caspase9 in undifferentiated NANOG$^{iCasp9\text{-}YFP}$ hESCs, subsequently triggering cell death (top left). NANOG$^{iCasp9\text{-}YFP}$ hESCs were treated for 24 hours with increasing concentrations of AP20187. AP20187 was withdrawn, and cultures were further grown in mTeSR1 to allow any surviving hESCs to grow; any surviving colonies were counted 1 week later (top right). Alkaline phosphatase staining of whole wells of a 12-well plate after 24-hour treatment with AP20187 (bottom). B) $5\times10^5$ NANOG$^{iCasp9-YFP}$ hESCs engineered to express Aka-Luciferase[42] were treated with control media or 1 nM AP20187 for 24 hours, and then subcutaneously transplanted into the right and left dorsal flanks of NOD-SCID Il2rg$^{-/-}$ mice ($5\times10^5$ cells per flank). Bioluminescent imaging of mice occurred weekly for 5 weeks with no transplant control (NTC) animals included for relative luminescence normalization. Total flux (photons/sec) was measured for each animal and averaged. C) NANOG$^{iCasp9-YFP}$ hESCs were differentiated for 6 days into derivatives of the ectoderm (forebrain), mesoderm (sclerotome) and endoderm (liver bud); for the last 24 hours, they were treated with 1 nM AP20187. The percentage of surviving cells was calculated relative to untreated controls. D) NANOG$^{iCasp9-YFP}$ hESCs were mixed 1:9 with NANOG$^{iCasp9-YFP}$ hESC-derived day-5 sclerotome cells and were cultured for 24 hours in sclerotome media (supplemented with 100 ng/mL FGF2 to help hESCs maintain pluripotency; Supplementary Methods), in the presence or absence of AP20187. Flow cytometric analysis was done to determine the percentage of YFP+ hESCs left in the mixed population (i). Surviving YFP+ hESCs were FACS sorted and cultured in mTeSR1 for 1 week to determine whether they were still capable of forming colonies (ii).
Figure 3:
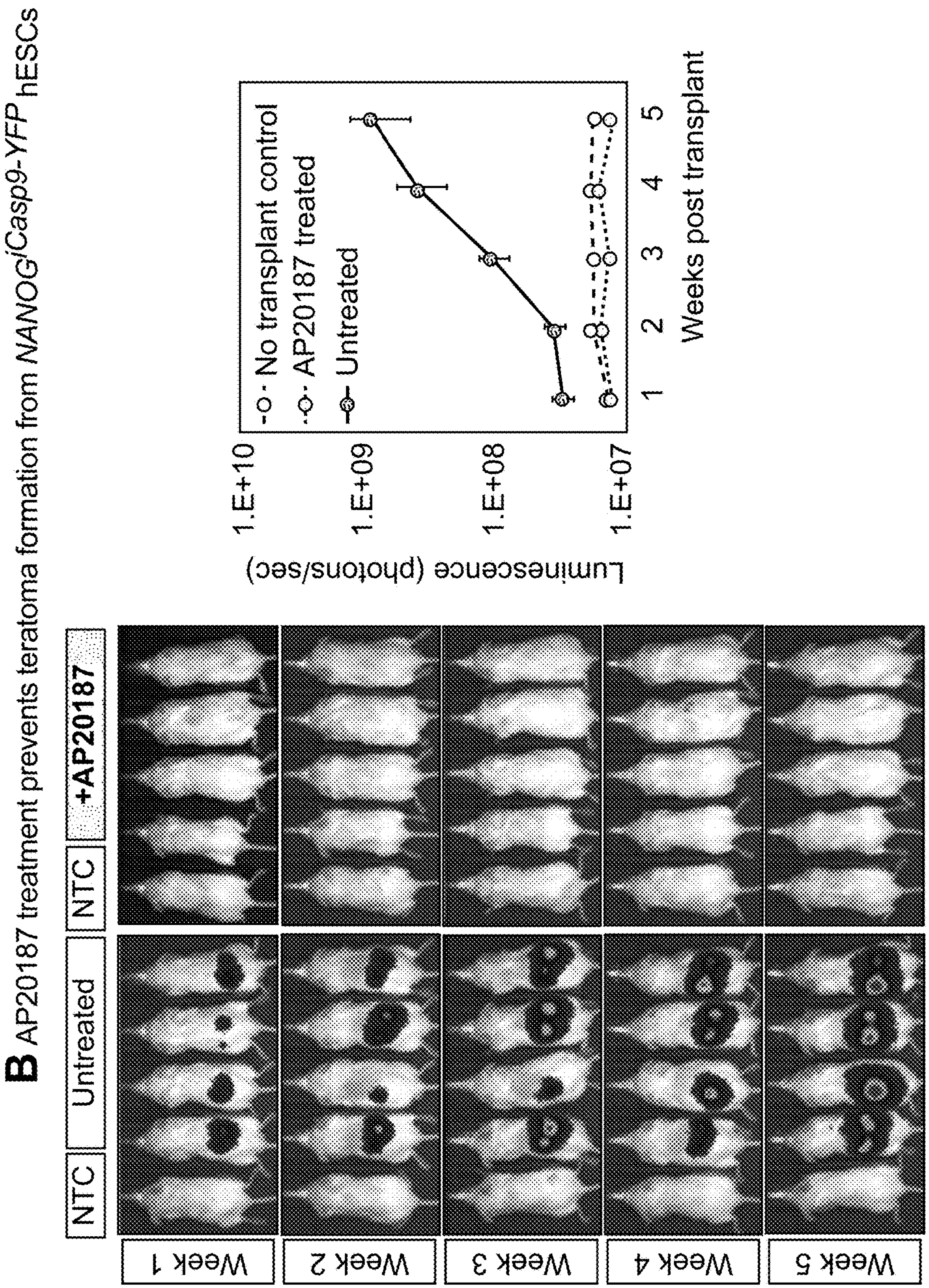
Figure 3:
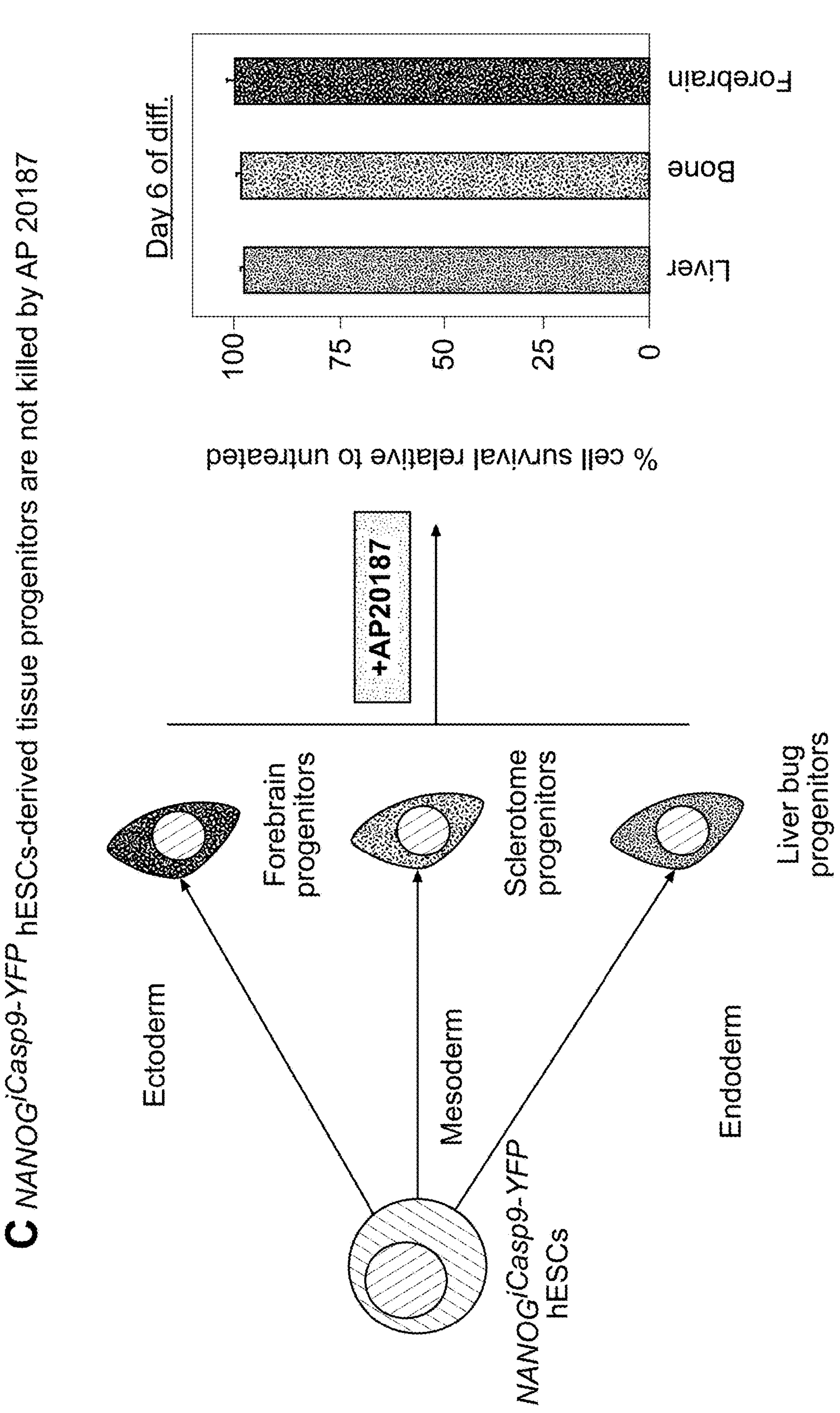
Figure 3:
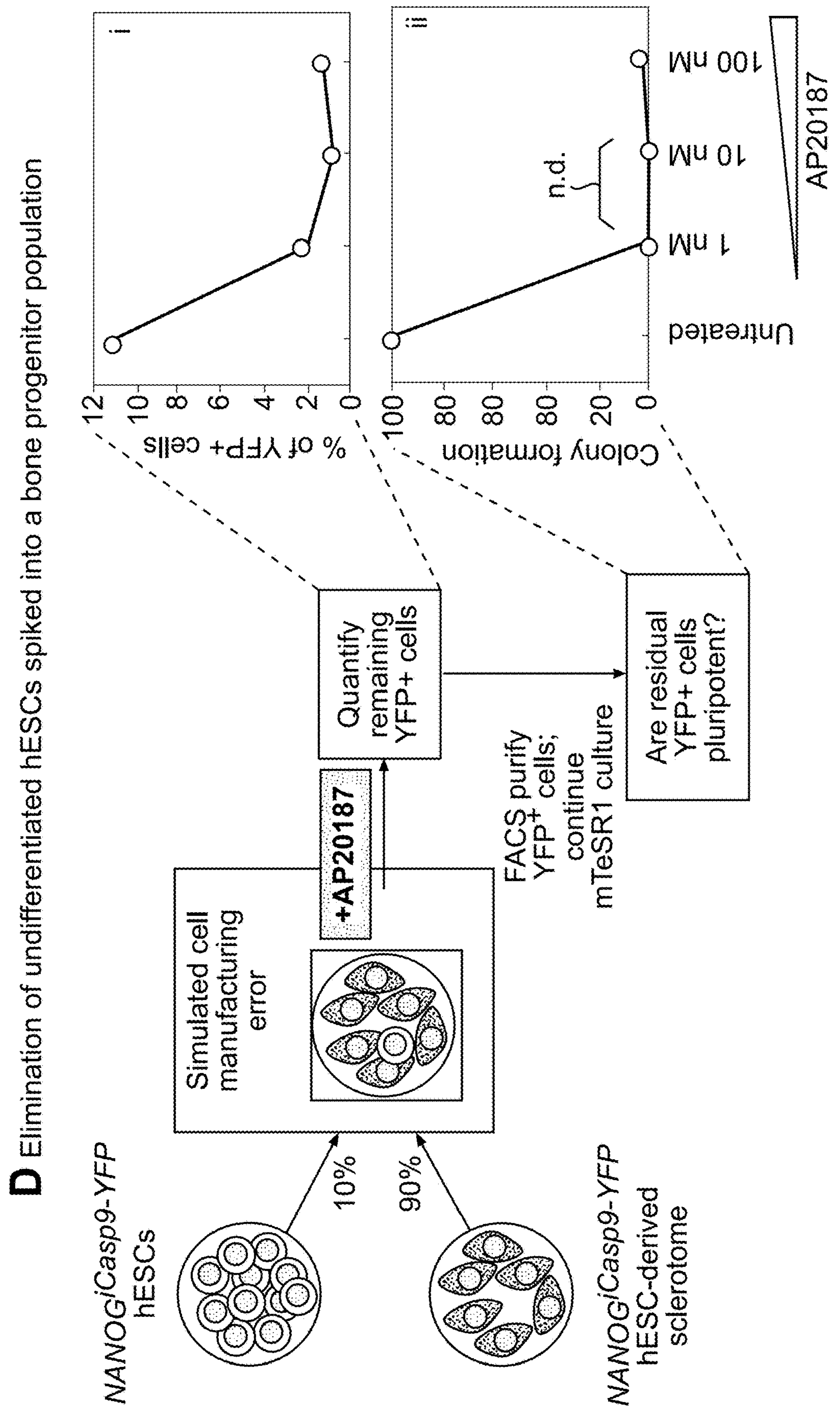

AP20 treatment activated iCaspase9 in undifferentiated NANOG$^{iCasp9\text{-}YFP}$ hPSCs and eliminated them, while sparing their differentiated progeny (FIG. 3). This system was effective (depleting undifferentiated hPSCs-$1\times10^6$-fold), sensitive (activated by 1 nM AP20), rapid (active within 12 hours) and specific (sparing >95% of differentiated bone, liver or forebrain progenitors). 24-hour treatment with 1 nM of AP20 led to a $1.75\times10^6$-fold depletion of undifferentiated hPSCs (as assayed across 7 independent experiments; FIG. 3*a*). This NANOG-iCaspase9 system enables greater than the 5-log reduction of hPSCs anticipated to be needed to ensure safety of a cell product with a billion differentiated cells. It also demonstrates quantitative killing of hPSCs exceeding prior reported systems, which generally deplete undifferentiated hPSCs by 1-log or less. AP20 was remarkably potent ($IC_{50}$=0.065 nM (FIG. 8*e,f*)) and rapid (even 12 hours of treatment sufficed to eliminate hESCs (FIG. 8*g*)).

Given that very small numbers of hPSCs (10,000) are sufficient to form teratomas in vivo, we tested the lower bounds of this system to test whether any rare hPSCs survived drug treatment and whether they could form teratomas. We pre-treated $5\times10^5$ hPSCs with control media or 1 nM AP20 for 24 hours prior to subcutaneous transplantation into NOD-SCID Il2rg$^{-/-}$ (NSG) mice to form teratomas (FIG. 3*b*). We used bioluminescent imaging (using the AkaLuciferase system) to determine if micro-teratomas might form, rather than visual inspection of subcutaneous nodules, because bioluminescent imaging is more sensitive and quantitative. Intravital imaging revealed that 0/14 of mice transplanted with AP20-treated hPSCs formed teratomas, whereas 14/14 of mice transplanted with control-treated hPSCs formed teratomas (FIG. 3*b*). Taken together, the ability to prevent the formation of even microscopic teratomas is an important step towards developing safer pluripotent cell-derived therapies.

Importantly, 24-hour treatment with AP20 specifically eliminated undifferentiated hPSCs while sparing differentiated hPSC-derived tissue progenitors: >95% of NANOG$^{iCasp9-YFP}$ hPSC-derived day-6 liver progenitors, bone progenitors and forebrain progenitors all remained viable (FIG. 3*c*, FIG. 8*h*), and expression of differentiation markers was not substantially effected (FIG. 8*i*). This is consistent with the loss of NANOG in each of these hPSC-derived tissue progenitor populations (FIG. 2*b*), whereas the same AP20 treatment regimen eliminated undifferentiated (NANOG$^{+}$) hPSCs (FIG. 8*h*). The NANOG$^{iCasp9-YFP}$ system also specifically eliminated undifferentiated hPSCs within heterogeneous cell populations. To simulate a cell-manufacturing failure, we generated day-5 hPSC-derived bone (sclerotome) progenitors and deliberately introduced 10% undifferentiated hPSCs (FIG. 3*d*). Treatment with AP20 for the last 24 hours of differentiation led to a >10-fold decrease in NANOG-YFP$^{+}$ cells (monitored by virtue of the YFP encoded in the NANOG$^{iCasp9-YFP}$ allele) (FIG. 3*di*). The surviving NANOG-YFP$^{+}$ cells were compromised and were no longer pluripotent, as upon FACS purification and continued culture in hPSC media, they did not form colonies within the limit of detection of our assay (FIG. 3*dii*). Similar results were observed when mixing hPSCs and sclerotome cells at different ratios (FIG. 8*j*). In conclusion, AP20 treatment of the NANOG$^{iCasp9-YFP}$ hPSCs provides an effective, sensitive, rapid and selective means to eliminate undifferentiated hPSCs without eliminating differentiated progeny.

Figure 4:
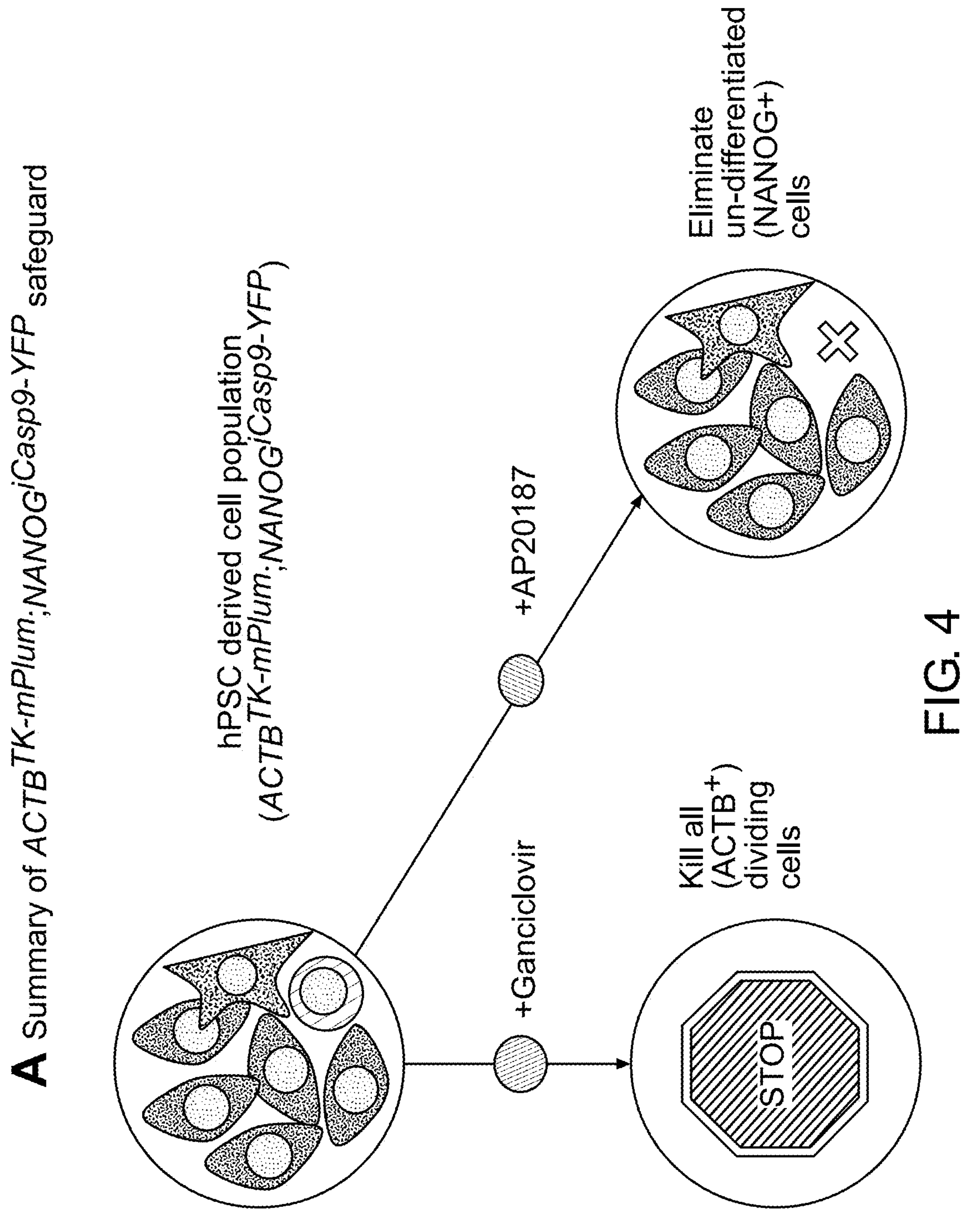
FIG. 4: Rationale and design of the ACTB$^{TK-mPlum}$ safety switch A) Intended application of the dual NANOG$^{iCasp9-YFP}$;ACTB$^{TK-mPlum}$ safeguard. B) Cas9 RNP/AAV6-based knock-in strategy for ACTB$^{TK-mPlum}$ targeting[37], which was performed in the NANOG$^{iCasp9-YFP}$ hESC line. C) mPlum was highly expressed in undifferentiated NANOG$^{iCasp9-YFP}$;ACTB$^{TK-mPlum}$ hESCs, as shown by epifluorescence (left) and flow cytometry (right). Wild-type hESCs were used as a negative control for flow cytometry gating. D) NANOG$^{iCasp9-YFP}$;ACTB$^{TK-mPlum}$ hESCs were differentiated into day 6 liver, sclerotome and neural progenitors with mPlum levels remaining high throughout each type of differentiation as shown by epifluorescence (top, for day 6 progenitors) and flow cytometry (bottom, each 24 hours of differentiation). Dotted line delineates negative versus positive cells, with the gate set on negative control (wild-type) hESCs.
Figure 4:
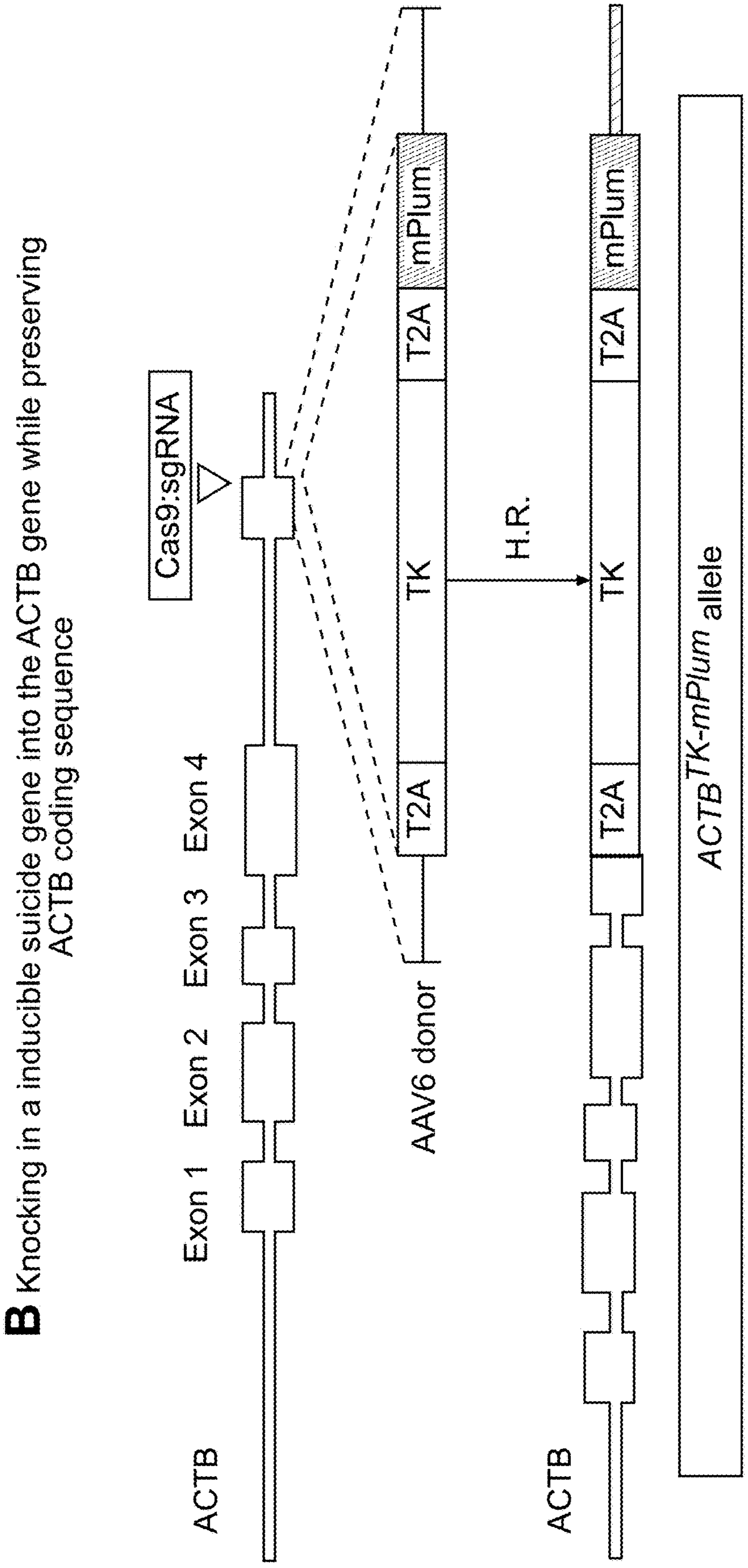
Figure 4:
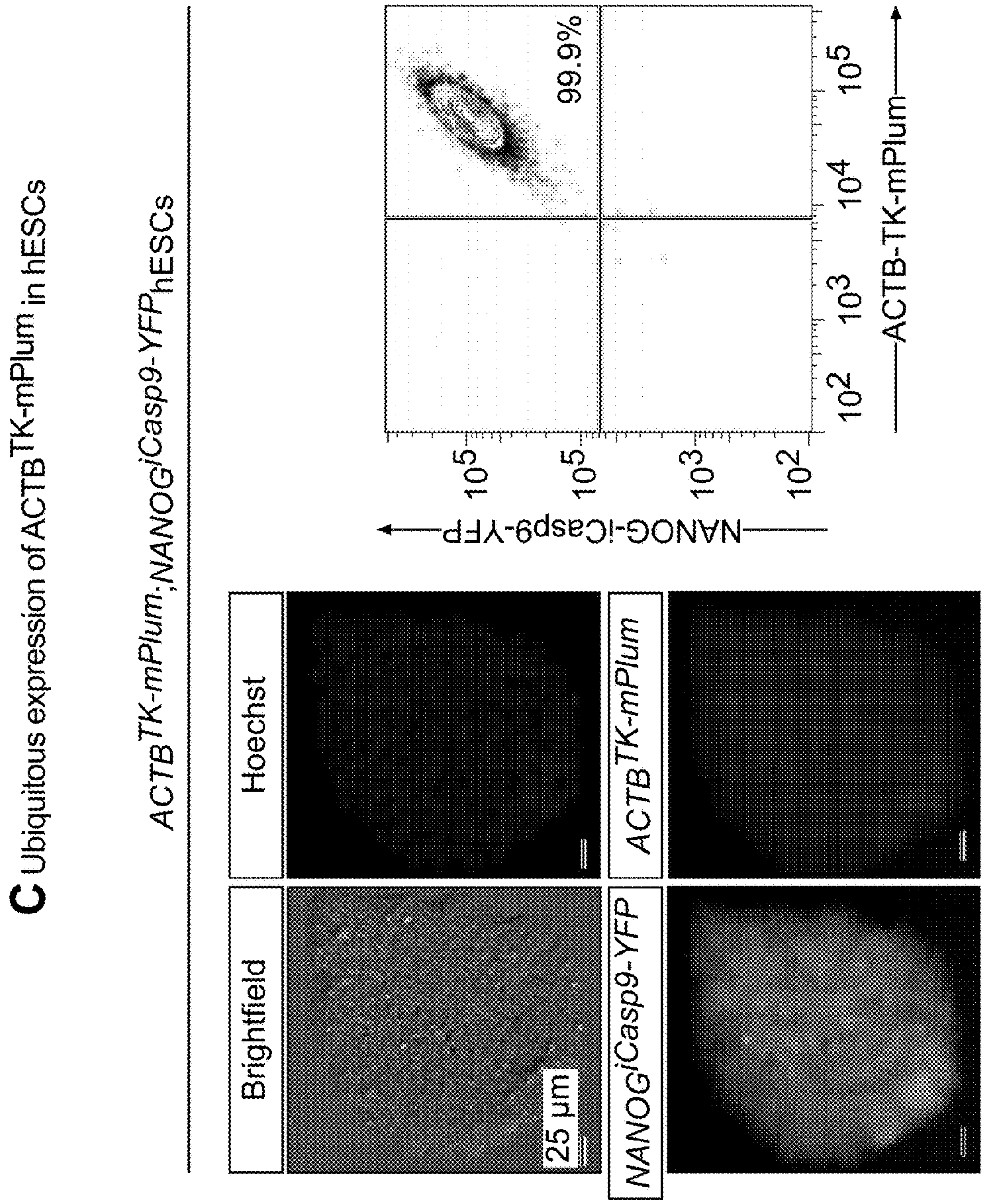
Figure 4:
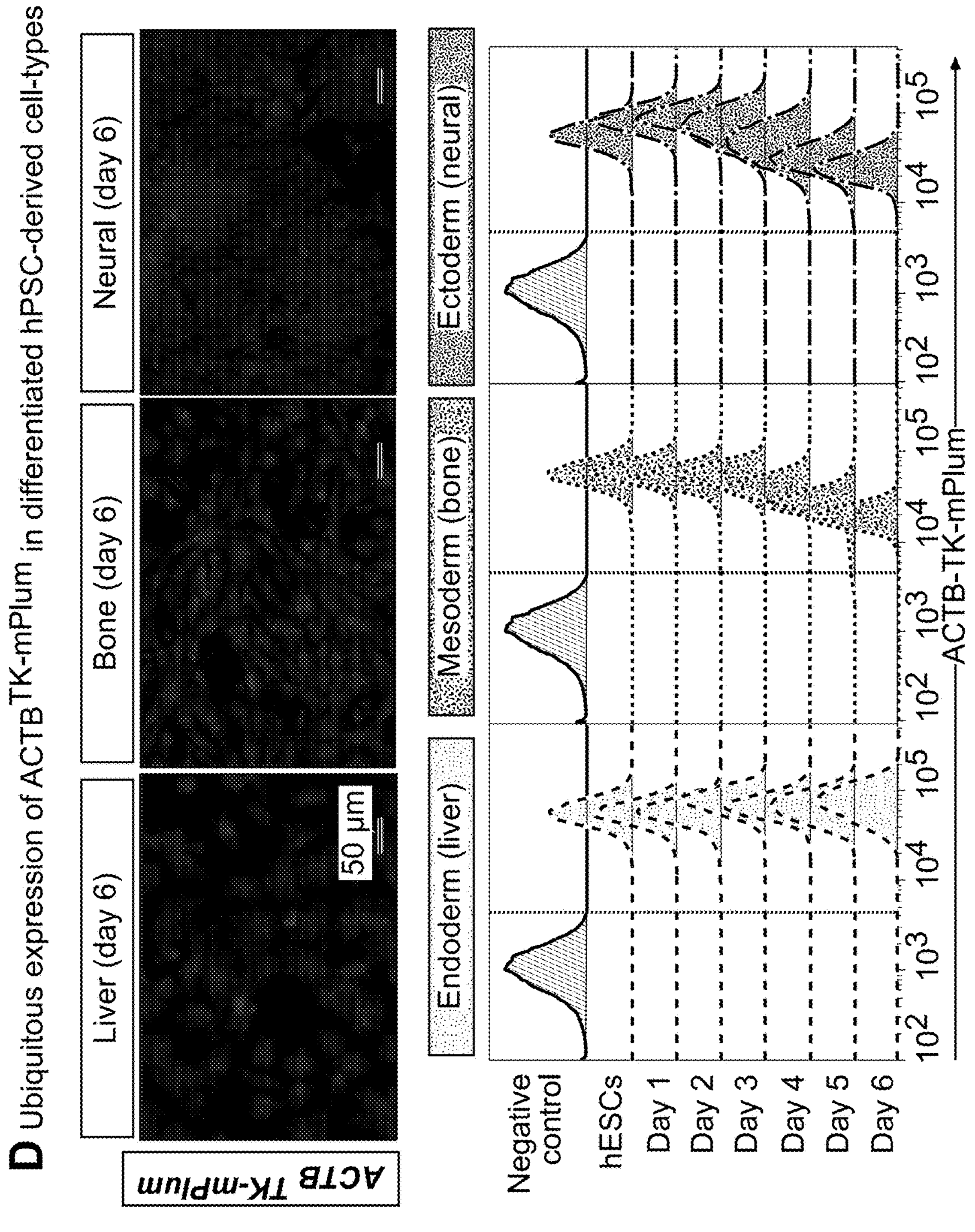
Figure 9:
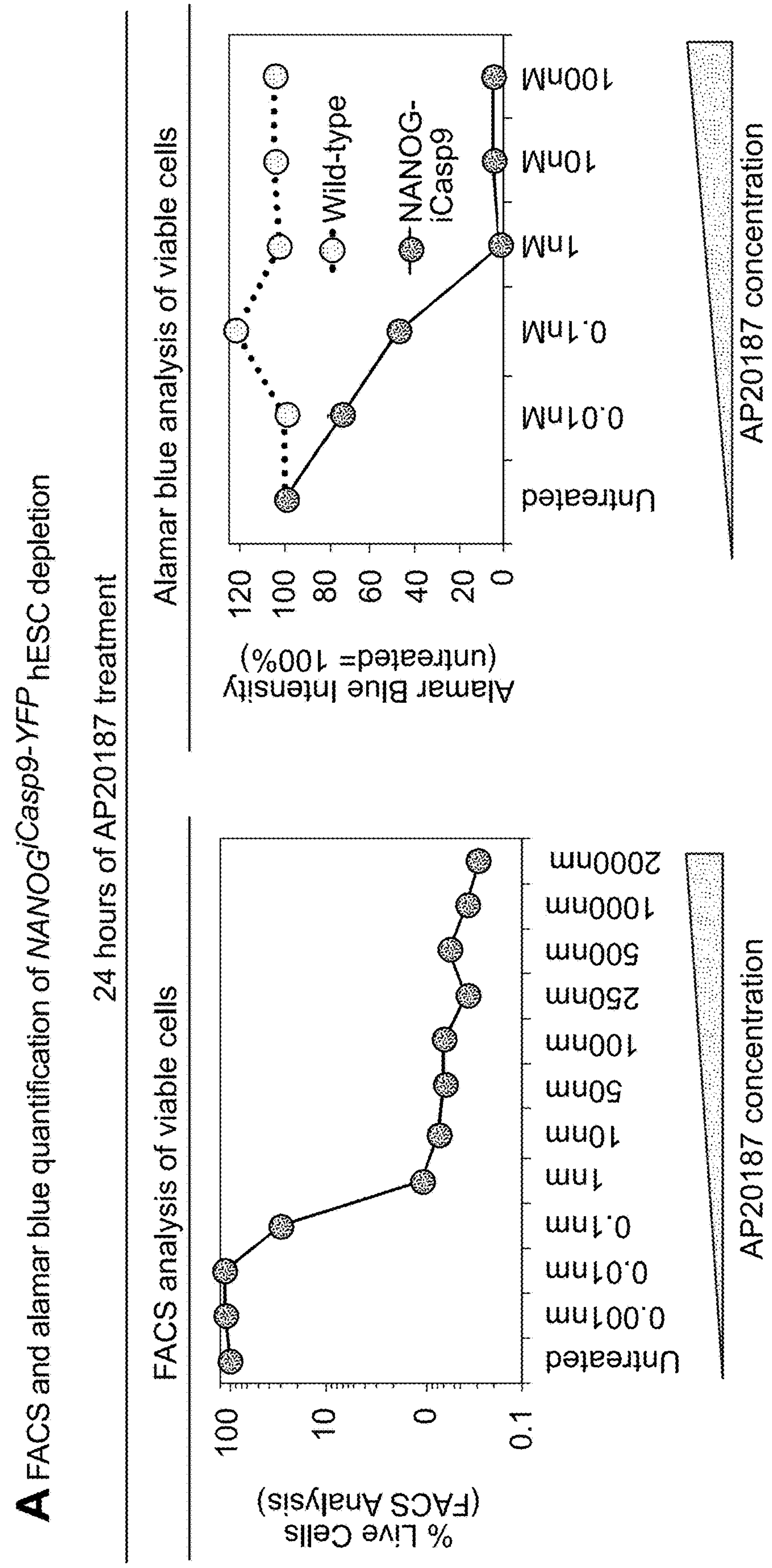
FIG. 9: Efficacy of the NANOG$^{iCasp9-YFP}$ safety switch (related to FIG. 3). A) Undifferentiated NANOG$^{iCasp9-YFP}$ hPSCs were treated with AP20187 at the indicated concentrations for 24 hours, and then the percentage of viable remaining cells was subsequently analyzed using FACS analysis (left) and alamar blue staining (right). For the FACS analysis, the percentage of cells shown represents viable cells (i.e., DAPI-negative cells obtained after DAPI staining) that were then gated for YFP+ (i.e., NANOG$^{+}$) cells. For the alamar blue analysis, wild-type hPSCs were used as a negative control. B) qPCR indicated that treatment with increasing doses of AP20187 downregulated NANOG mRNA expression in undifferentiated hPSCs. AP20187 doses equal to or greater than 100 nM may prevent efficient killing of NANOG$^{iCasp9-YFP}$ hPSCs by considerably down-regulating NANOG. Gene expression is depicted normalized to the reference gene YWHAZ (i.e., YWHAZ=1.0). C) Undifferentiated NANOG$^{iCasp9-YFP}$ hPSCs were treated with the indicated doses of AP20187 for various lengths of time (6, 12, 24, 48, 72 hours) and then alamar blue assay was performed immediately thereafter to quantify the extent of cell death. This revealed that AP20187-induced cell death occurs within 12 hours of treating NANOG$^{iCasp9-YFP}$ hPSCs with 1 nM of AP20187. D) Immunofluorescent imaging of NANOG$^{iCasp9-YFP}$ hESCs in the undifferentiated state and after differentiation into day 6 sclerotome as marked by TWIST1 expression, both without and with treatment of cells with 1 nM AP20187 for 24 hours. E) Transcriptional analysis of differentiated cell-types before and after AP20187 (1 nM) treatment for 24 hours showed that AP20187 treatment did not substantially impact marker gene expression. The following marker genes were assessed in each respective cell-type: sclerotome (bone) progenitors (TWIST1, SOX9, PAX1, PAX9), liver progenitors (SOX17, HNF4A, AFP, TBX3), and forebrain (neural) progenitors (PAX6, FOXG1, OTX2, SIX3). F) Further validation of NANOG$^{iCasp9-YFP}$ using a simulated mixed cell culture assay. NANOG$^{iCasp9-YFP}$ undifferentiated hPSCs and hPSC-derived derived sclerotome cells were mixed at a 3:7 ratio, respectively. Mixed cells were treated with AP20187, and 24 hours post-treatment, FACS analysis was done to assess remaining NANOG$^{iCasp9-YFP}$ hPSCs in culture.
Figure 9:
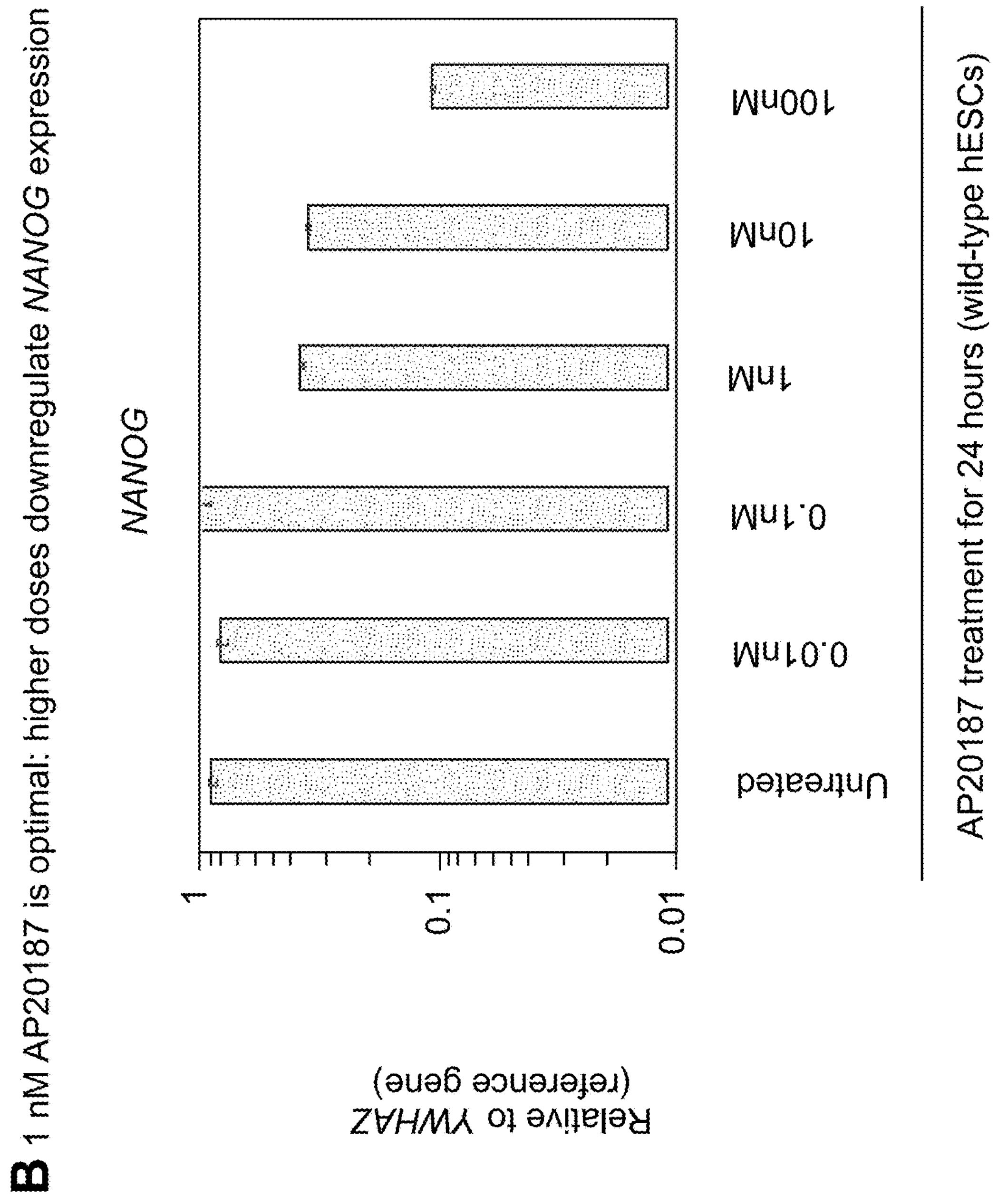
Figure 9:
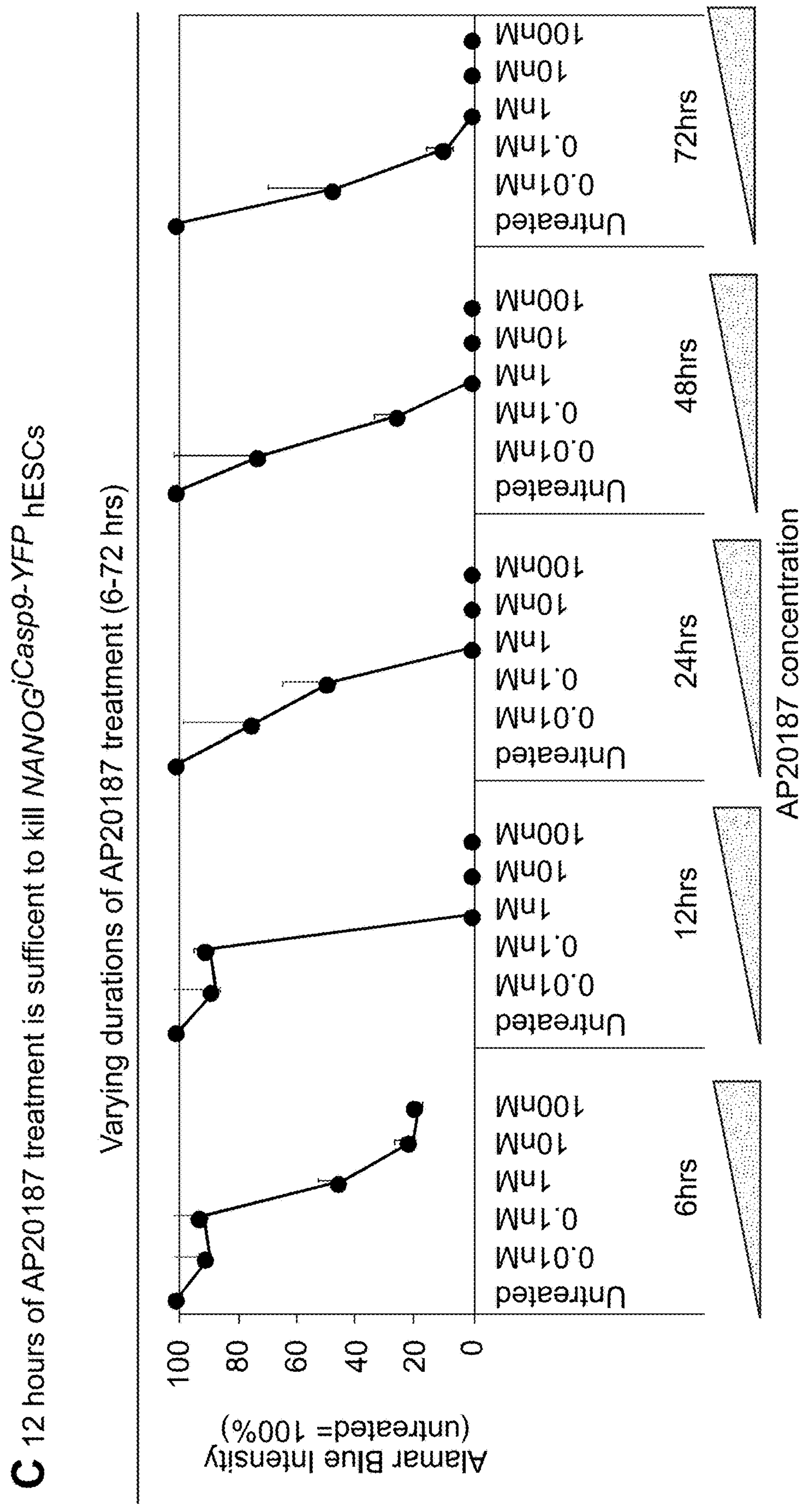
Figure 9:
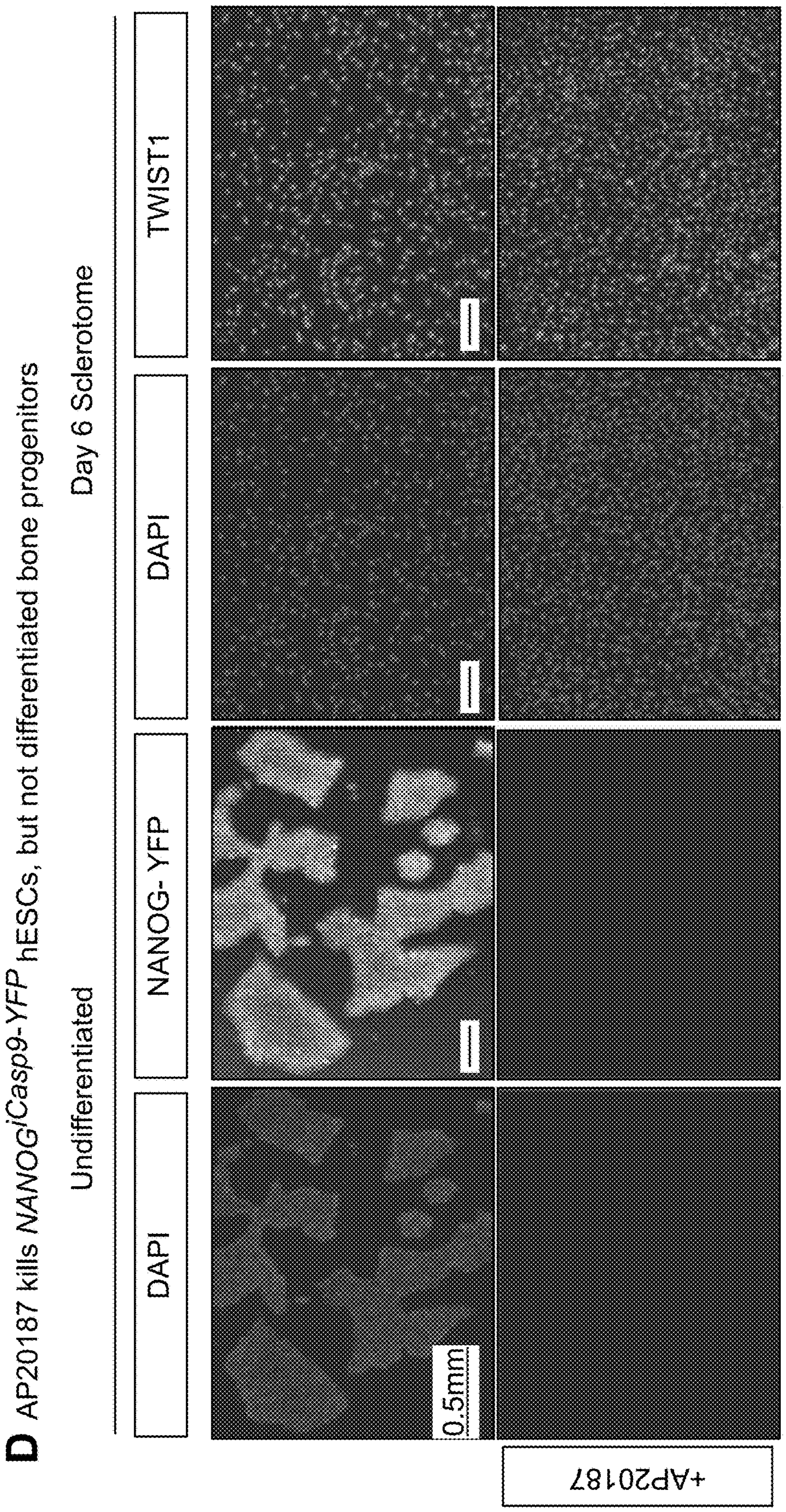
Figure 9:
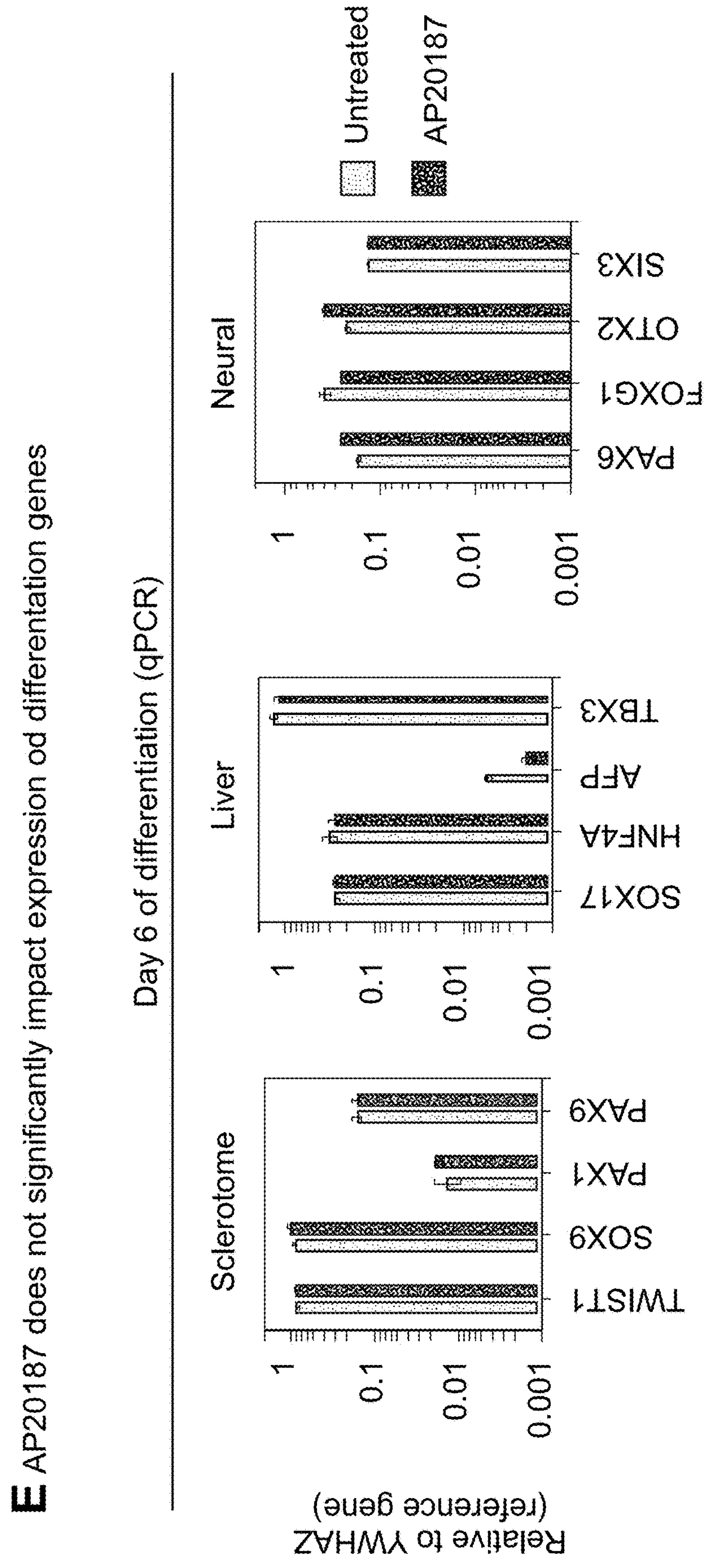
Figure 9:
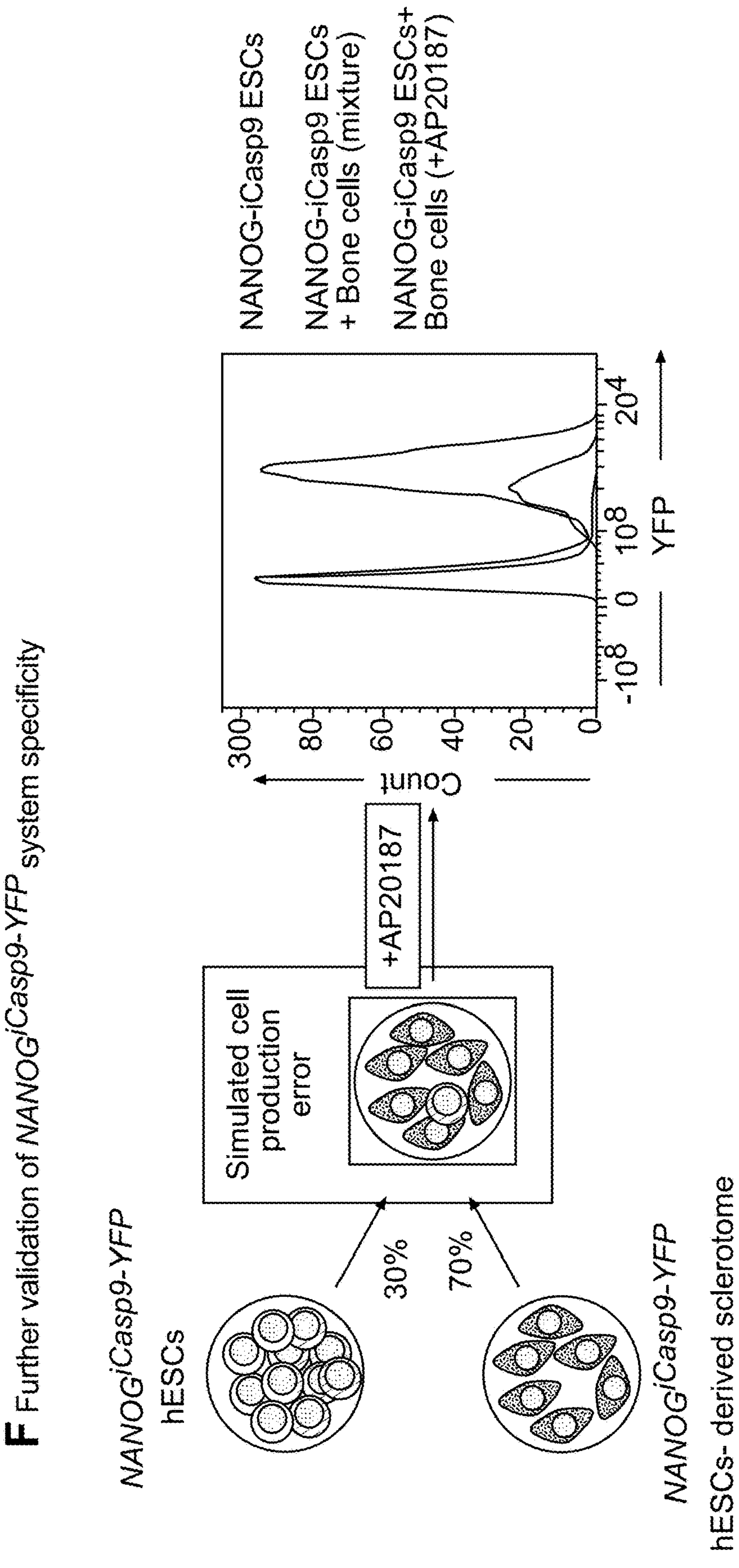
Figure 10:
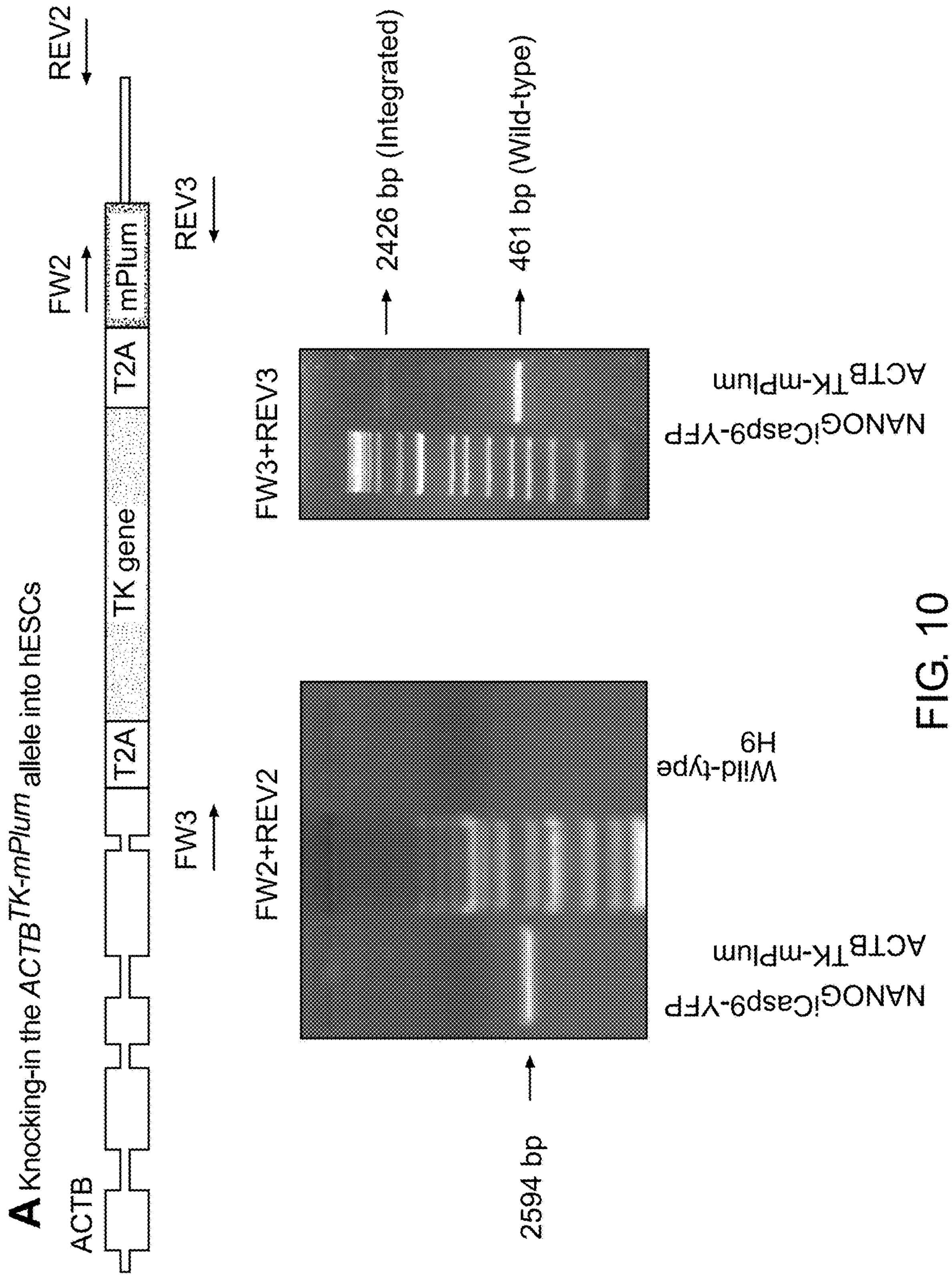
FIG. 10: Supporting data for ACTB$^{TK-mPlum}$ safety switch (related to FIGS. 4-5). A) Schema of targeted ACTB$^{TK-mPlum}$ allele, with forward and reverse primers used for genotyping indicated. Genomic in-out PCR showing 2594 bp band for the C-terminal-end integrated sequence revealed targeting of the ACTB locus and PCR confirming mono-allelic integration of ACTB$^{TK}$". B) qPCR to assess the expression of GADPH, RPLP0, ACTB mRNAs during neural, bone and liver differentiation revealed that they are all ubiquitously expressed, with ACTB showing the highest expression levels. Expression of lineage markers is depicted normalized to the reference gene YWHAZ (i.e., YWHAZ=1.0). C) $10^6$ ACTB$^{TK-mPlum}$;NANOG$^{iCasp9-YFP}$ hESCs engineered to express AkaLuciferase were treated with control media or 1 nM AP20187 for 24 hours, and then subcutaneously transplanted into the left and right dorsal flanks of NOD-SCID Il2rg$^{-/-}$ mice ($10^6$ cells per flank. After 3 weeks post-transplant, teratomas formed in vivo and ganciclovir was administered daily at 50 mg/kg for 4 further weeks. Bioluminescent imaging of mice occurred weekly for 7 weeks. Total flux (photons/sec) was measured for each animal.
Figure 10:
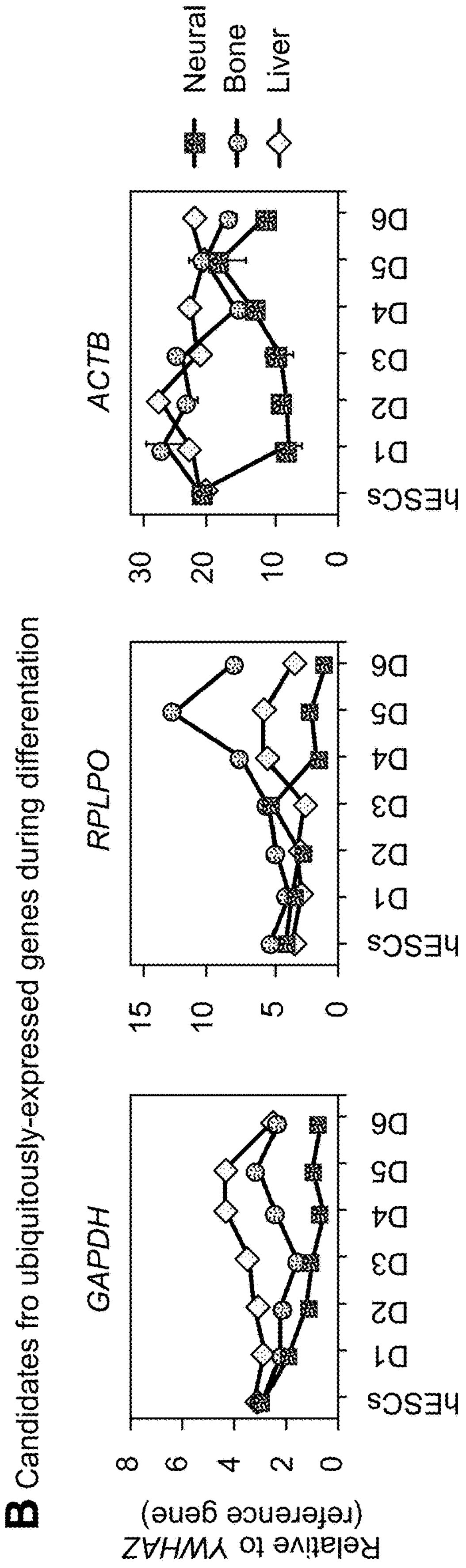
Figure 10:
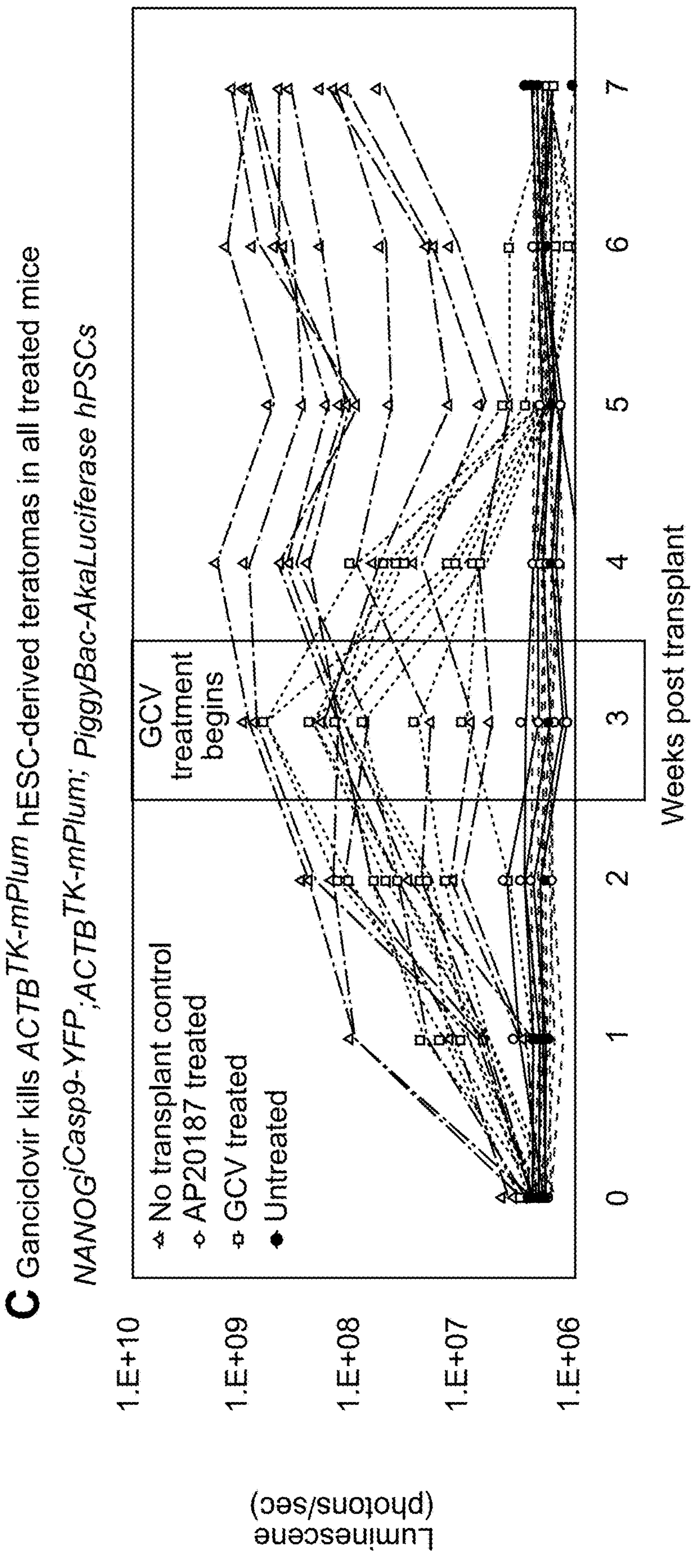
Figure 10:
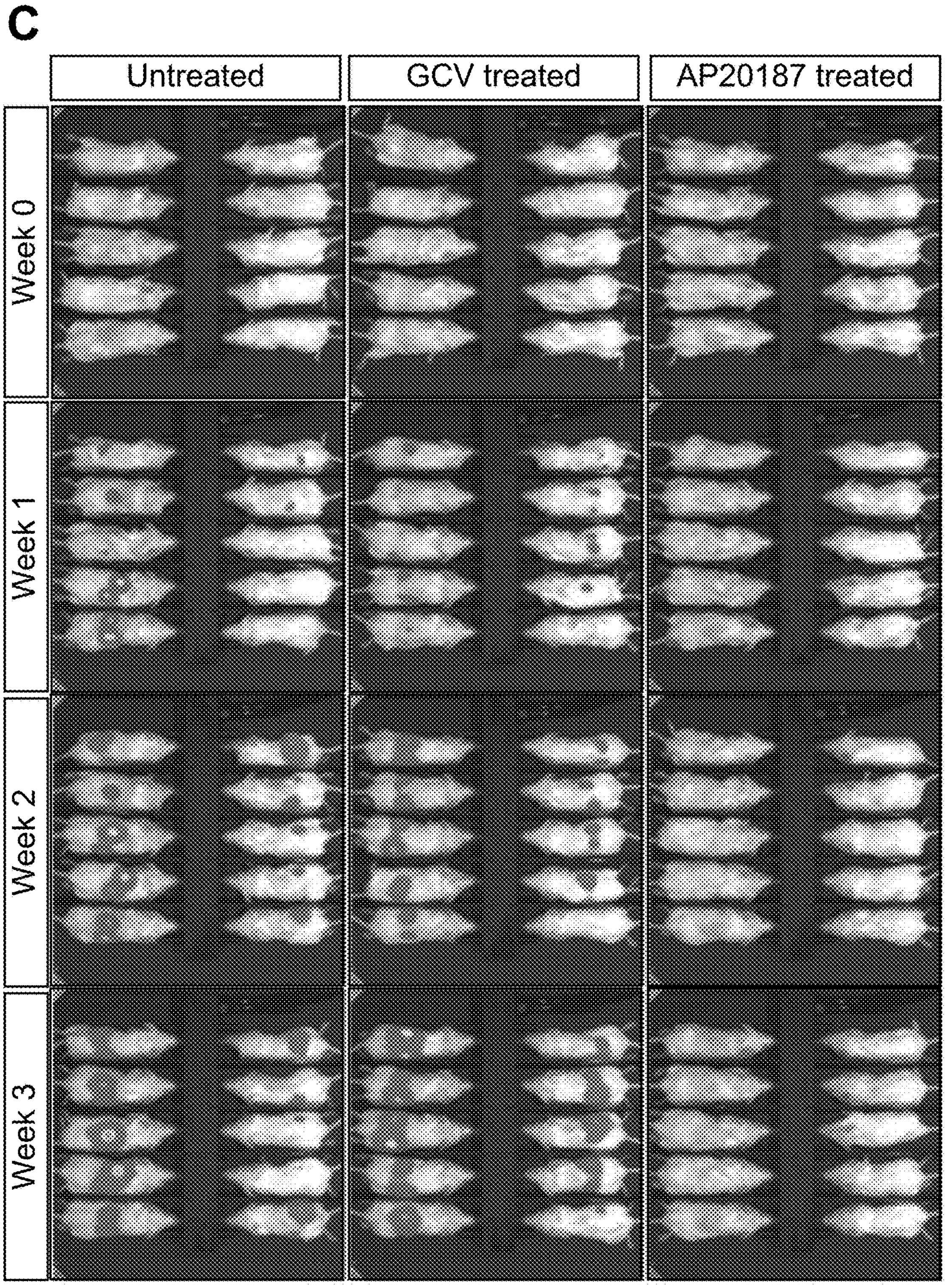
Figure 10:
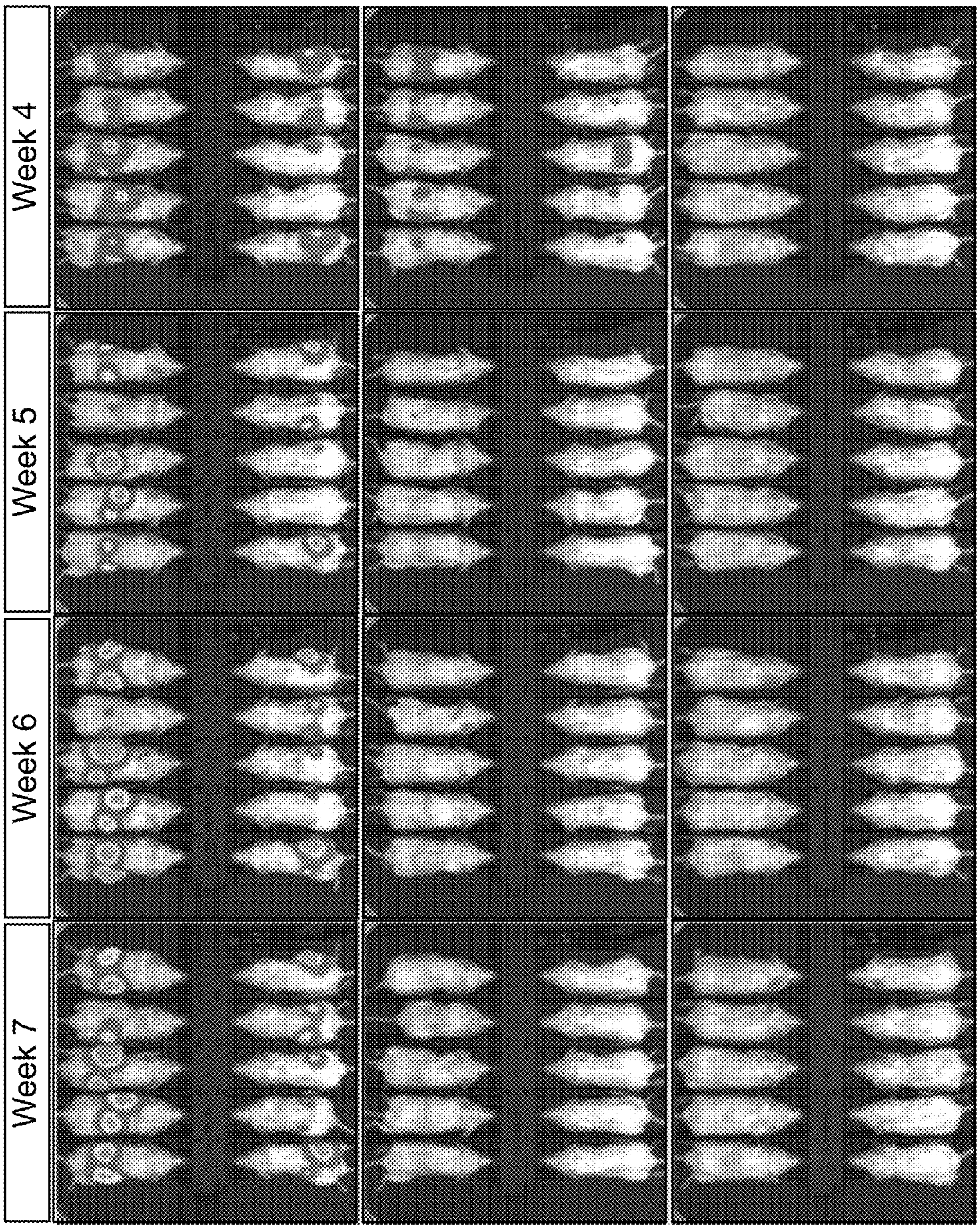
Figure 11:
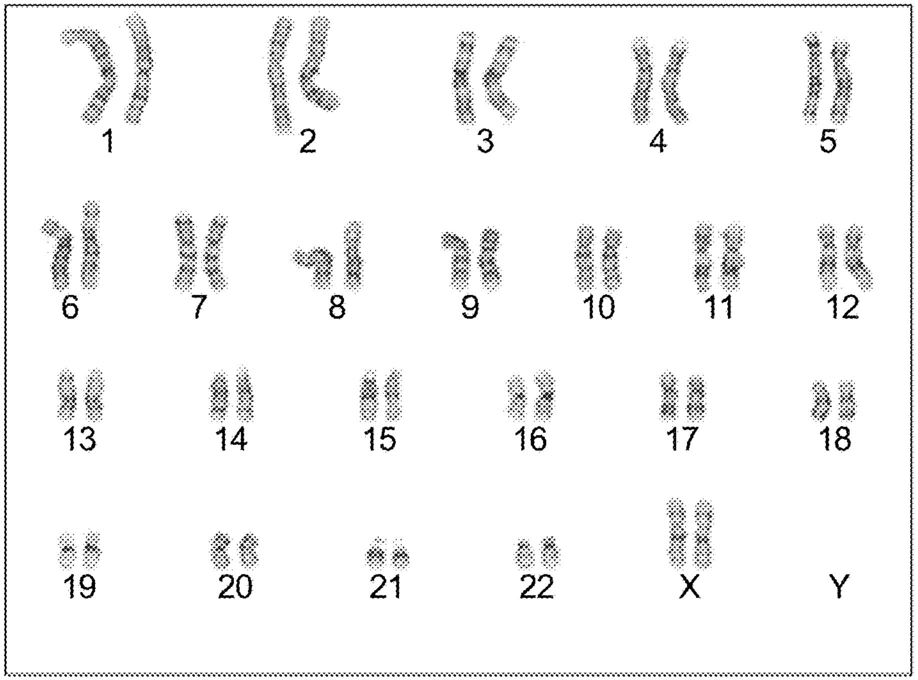
FIG. 11: Supporting data for ACTB$^{OiCasp9-mPlum}$ safety switch (related to FIG. 6). A) Knock-in efficiencies at the NANOG and ACTB loci in hPSCs. Targeting efficiencies were quantified by performing flow cytometry of bulk hPSC populations edited through the Cas9 RNP/AAV6 system[37] (prior to single-cell cloning to generate clonal cell lines), and assessing the percentage of cells expressing the respective fluorescent reporters (YFP, in the case of the NANOG$^{iCasp9-YFP}$ allele or else mPlum, in the case of the ACTB$^{OiCasp9-mPlum}$ allele). Notably, while the Cas9 RNP/AAV6 system has been reported to generate knock-in alleles with 20-60% efficiency in hPSCs at multiple genes that not essential for cellular viability, here the targeting efficiencies at the NANOG and ACTB loci were lower. This is likely because Cas9 inflicts double-strand DNA breaks, which are known to transcriptionally silence nearby genes as part of the DNA damage response. Temporary silencing of NANOG and ACTB likely led to cell death or differentiation, thus hindering the recovery of successfully-targeted hPSCs. B) NANOG$^{iCasp9-YFP}$;ACTB$^{OiCasp9-mPlum}$ hESCs were karyotypically normal (36 passages after initial NANOG$^{iCasp9-YFP}$ targeting). C) To confirm that AP21967 (which activates OiCaspase9) does not kill iCaspase9-expressing cells, ACTB$^{TK-mPlum}$;NANOG$^{iCasp9-YFP}$ hESCs were treated with AP21967 for 24 hours at the indicated doses and then the number of surviving cells was quantified by cell counting. D) To confirm that AP21967 (which activates OiCaspase9) does not kill iCaspase9-expressing cells, a mixture of 40% NANOG$^{iCasp9-YFP}$ hESCs+60% doubly-transgenic ACTB$^{OiCasp9-mPlum}$;NANOG$^{iCasp9-YFP}$ hESCs was either left untreated or treated with AP21967 (1 nM) for 24 hours, and the proportion of surviving cells was quantified by flow cytometry. E) $10^6$ ACTB$^{OiCasp9\text{-}mPlum}$;NANOG$^{iCasp9\text{-}YFP}$ hESCs engineered to express CAG-AkaLuciferase were treated with control media or 1 nM AP20187 for 24 hours, and then subcutaneously transplanted into the left and right dorsal flanks of NOD-SCID Il2rg$^{-/-}$ mice ($10^6$ cells per flank). 4 weeks post-transplant, teratomas formed in vivo and AP21967 was intraperitoneally administered once at 10 mg/kg. Bioluminescent imaging of mice was conducted weekly for 8 weeks (with the exception of week 4, when imaging was performed again 3 days post-AP21967 administration). Total flux (photons/sec) was measured for each individual animal. F) Bioluminescent imaging of individual animals shown in FIG. 10*e*.
Figure 11:
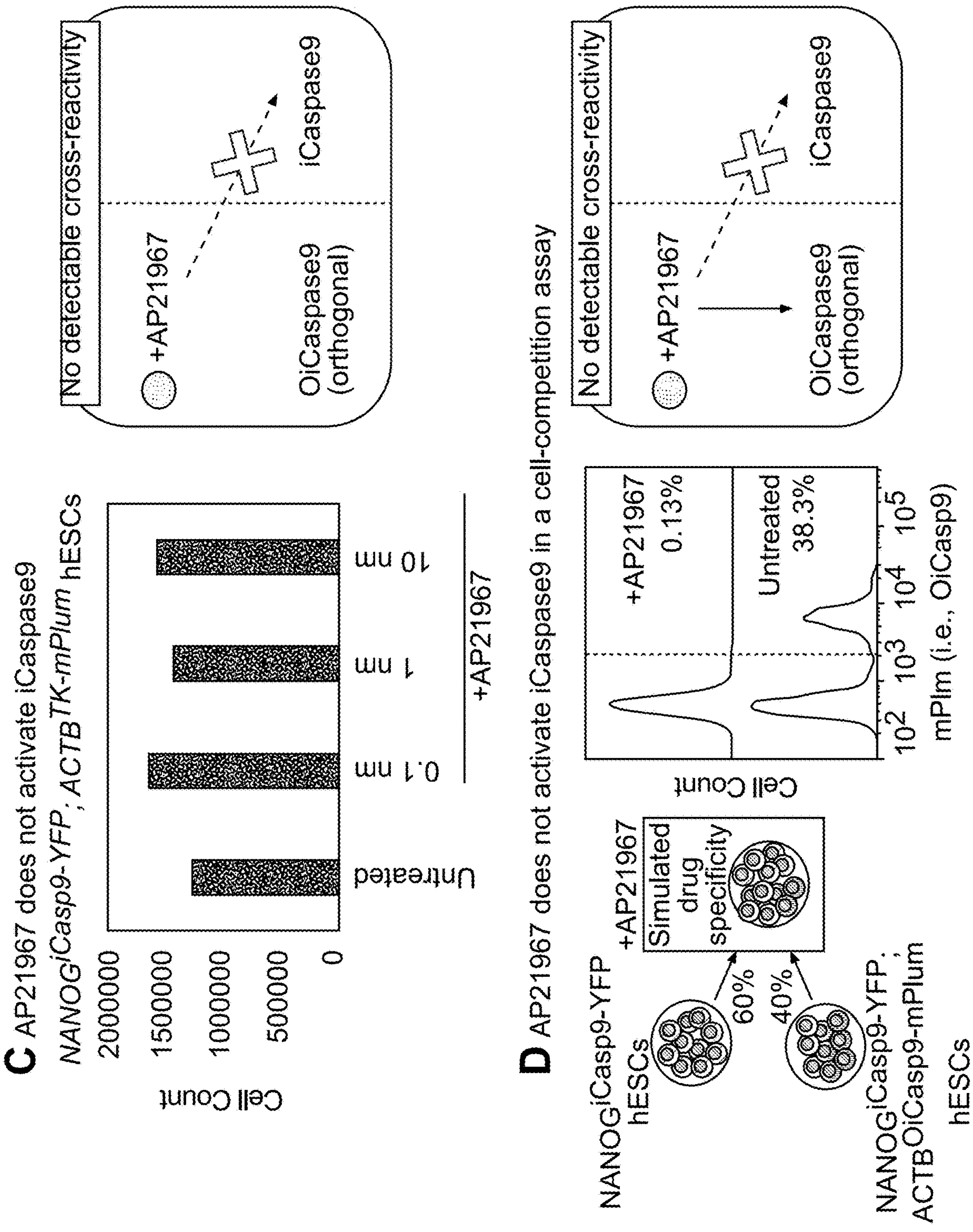
Figure 11:
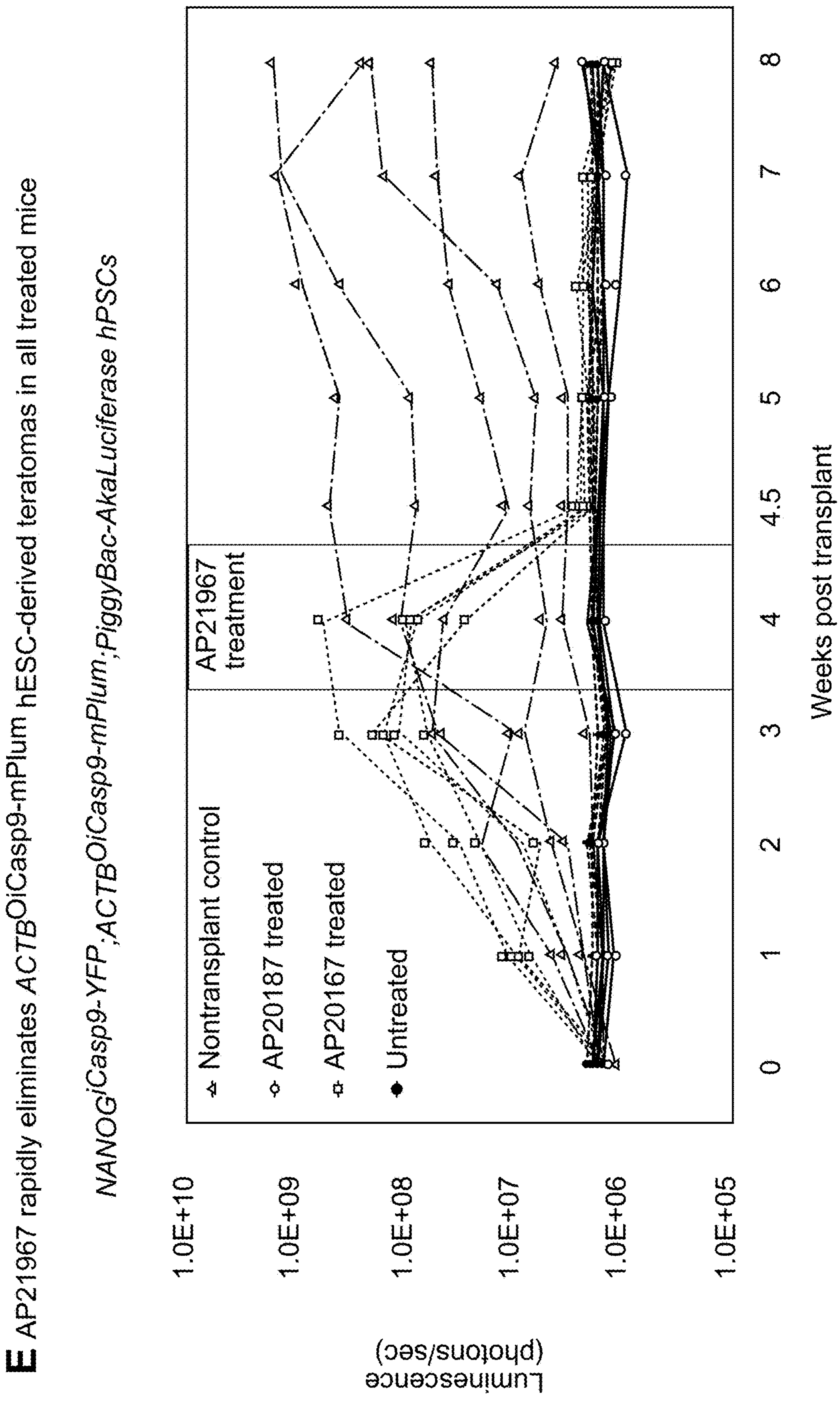
Figure 11:
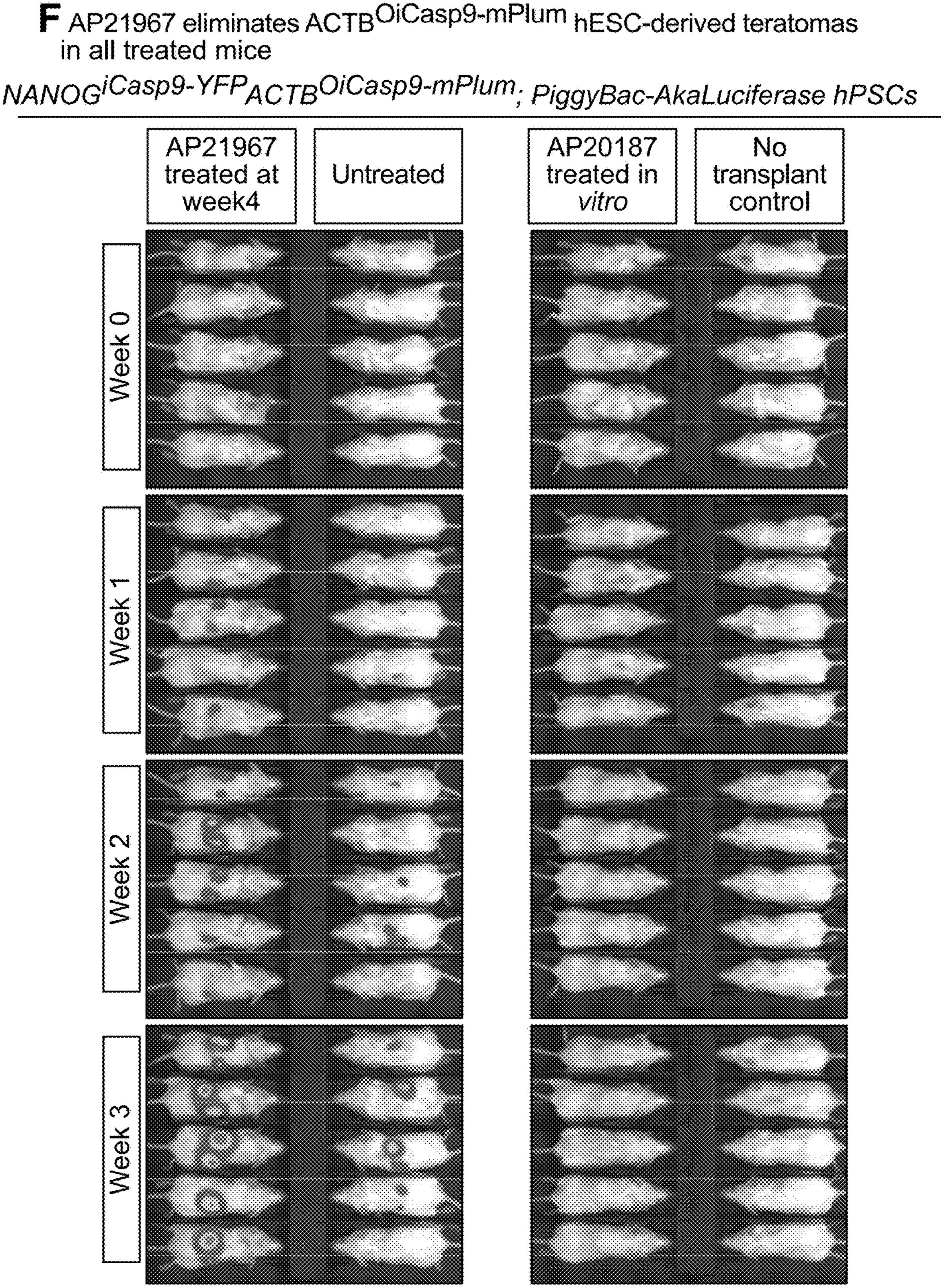
Figure 11:
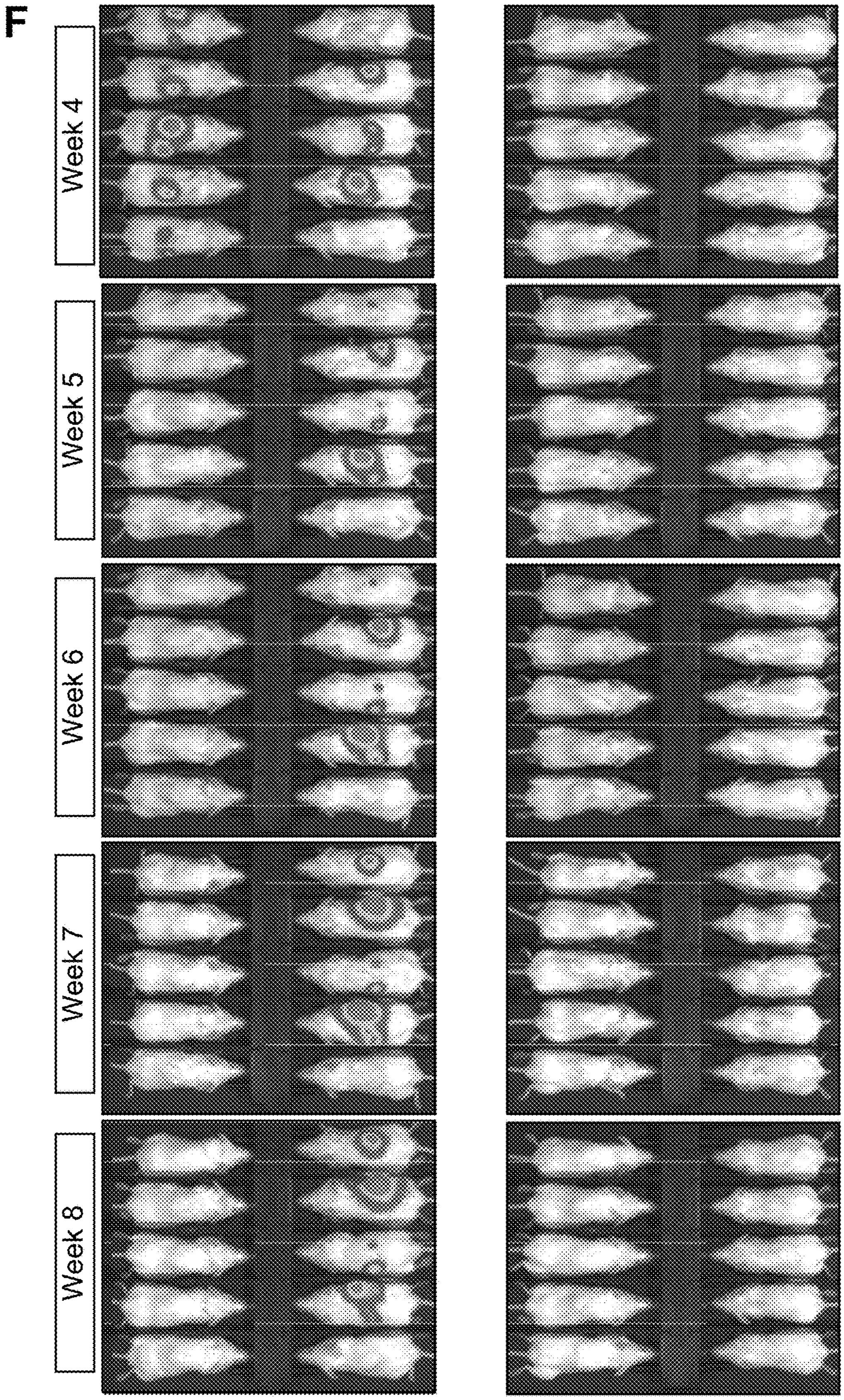

ACTB$^{HSV-TK}$ system to halt the in vivo growth of hPSC-derived populations. While the NANOG$^{iCasp9-YFP}$ system reduces teratoma risk, this is not the only concern for hPSC-derived cell therapies as differentiated PSC-derived cell-types can uncontrollably proliferate in vivo, as observed for neural overgrowths. The NANOG$^{iCasp9-YFP}$ system would not be an effective safeguard for this type of toxicity. We thus developed an orthogonal drug-inducible safeguard to curb the growth of, or eliminate, all transplanted cells in vivo if overgrowing, unwanted, or damaging tissues/cells are detected post-transplantation (FIG. 4*a*). This system could also be used to eliminate transplanted hPSC-derived cells once their therapeutic effect was achieved, thus allowing a living drug to have a controllable endpoint. To this end, in the NANOG$^{iCasp9-YFP}$ hPSC line, we knocked-in a second drug-inducible kill-switch (TK$^{HSV}$) and a fluorescent reporter (mPlum) into both alleles of a constitutively-expressed gene (ACTB [BETA-ACTIN]) (FIG. 4*b*; FIG. 9*a,b*). Ganciclovir is phosphorylated by TK$^{HSV}$ to a nucleotide analogue that competes with ddGTP which, after incorporation into DNA during replication, results in chain termination, consequently blocking cell proliferation. In our system, TK$^{HSV}$ is specifically gene-targeted into, and thus expressed under the control of, the ubiquitously-expressed ACTB locus (FIG. 4*b*; FIG. 8*a,b*). Ganciclovir treatment should therefore halt the growth of all hPSC-derived cell-types, irrespective of their lineage or differentiation status. The proliferation, pluripotency marker expression, and differentiation potential of hPSCs following biallelic ACTB knock-ins was not overtly perturbed (FIG. 4*c*; FIG. 7*c*; FIG. 9*a*), suggesting that the function of ACTB (a generally essential gene) was preserved.

We showed that the ACTB$^{HSV-TK-mPlum}$ cassette was highly expressed in undifferentiated hPSCs as well as hPSC-derived endoderm, mesoderm and ectoderm tissue progenitors (FIG. 4*c,d*), paralleling ACTB mRNA expression (FIG. 9*b*). Because TK$^{HSV}$ is expressed under the control of the endogenous ACTB locus, our system should evade silencing, unlike previous transgenes driven by exogenous viral promoters. Indeed, given that ACTB is generally an essential gene, if both alleles were silenced, the cell would likely die.

Figure 5:
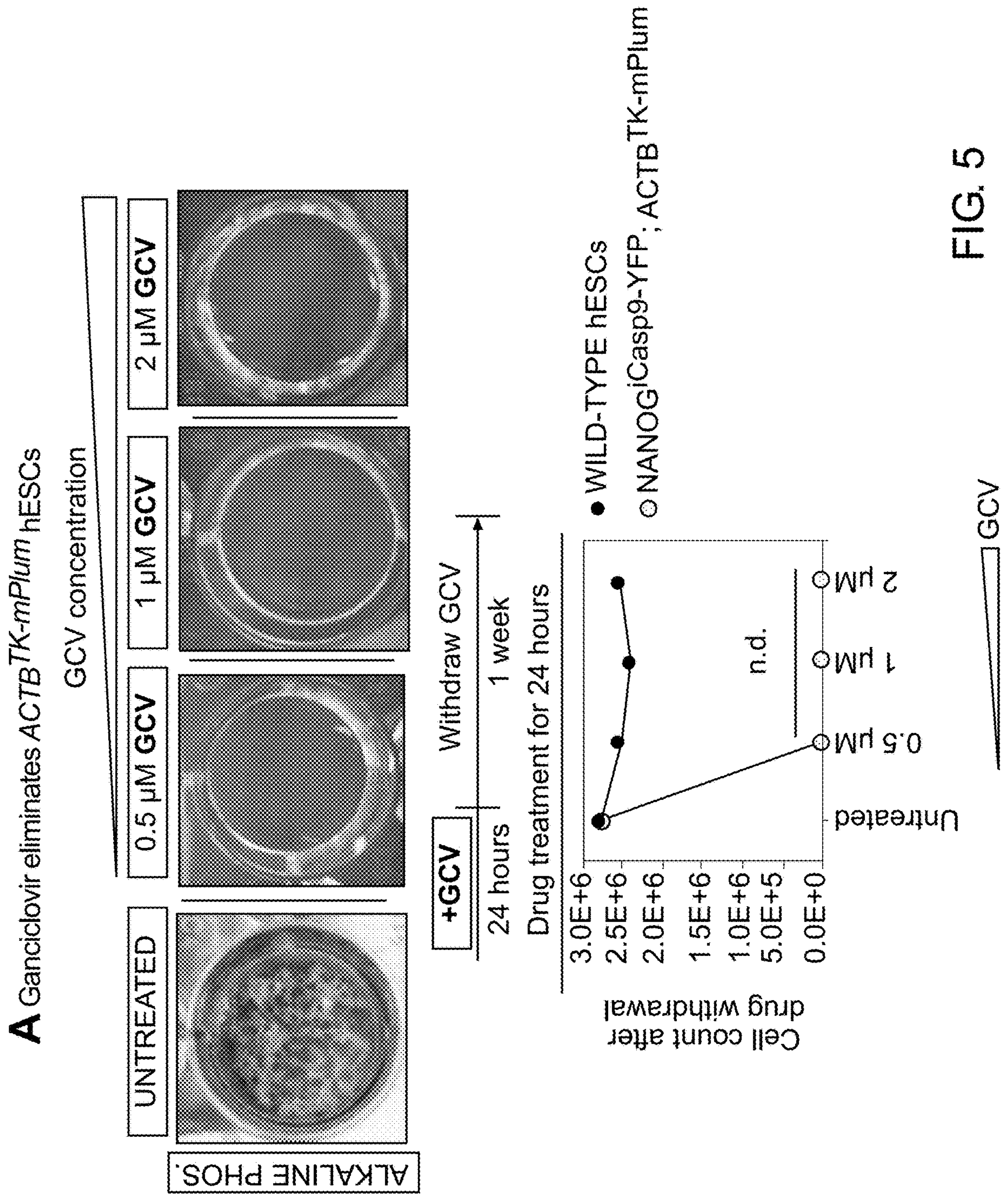
FIG. 5: Implementation of the ACTB$^{TK-mPlum}$ safety switch. A) NANOG$^{iCasp9-YFP}$;ACTB$^{TK-mPlum}$ hESCs were treated with ganciclovir (or left untreated) for 24 hours, and subsequently ganciclovir was withdrawn and hESCs were cultured for 1 week in mTeSR1 to detect any surviving cells and to allow them to regrow. Alkaline phosphatase staining of whole wells of a 12-well plate for each condition (top) and cell counts for wild type and NANOG$^{iCasp9-YFP}$; ACTB$^{TK-mPlum}$ hESCs after each treatment (bottom) demonstrated the elimination of hESCs. N.D.=not detected. B) NANOG$^{iCasp9-YFP}$;ACTB$^{TK-mPlum}$ hESCs were differentiated into day 6 liver, sclerotome and neural progenitors and treated with ganciclovir at the indicated doses for the last 24 hours of differentiation. Cell survival was analyzed by counting at day 6 of differentiation. C) $10^6$ NANOG$^{iCasp9-YFP}$; ACTB$^{TK-mPlum}$ hESCs engineered to express CAG-AkaLuciferase were treated with control media or 1 nM AP20187 for 24 hours, and then subcutaneously transplanted into the right and left dorsal flanks of NOD-SCID Il2rg$^{-/-}$ mice ($10^6$ cells per flank). After 3 weeks post-transplant, teratomas formed in vivo and ganciclovir was administered daily at 50 mg/kg until week 7 post-transplant. Bioluminescent imaging of mice was conducted weekly for 7 weeks. Total flux (photons/sec) was measured for each animal and were averaged.
Figure 5:
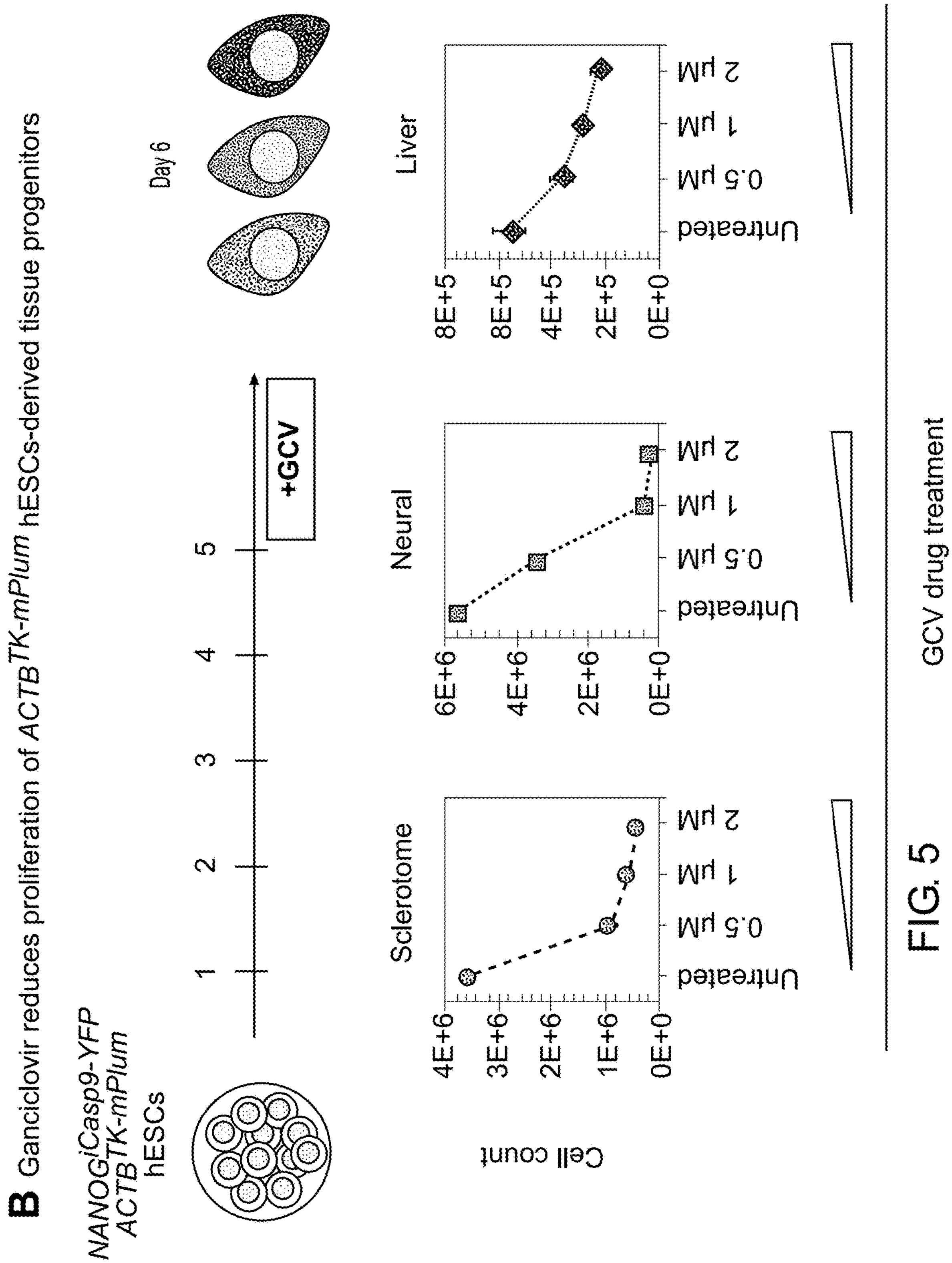
Figure 5:
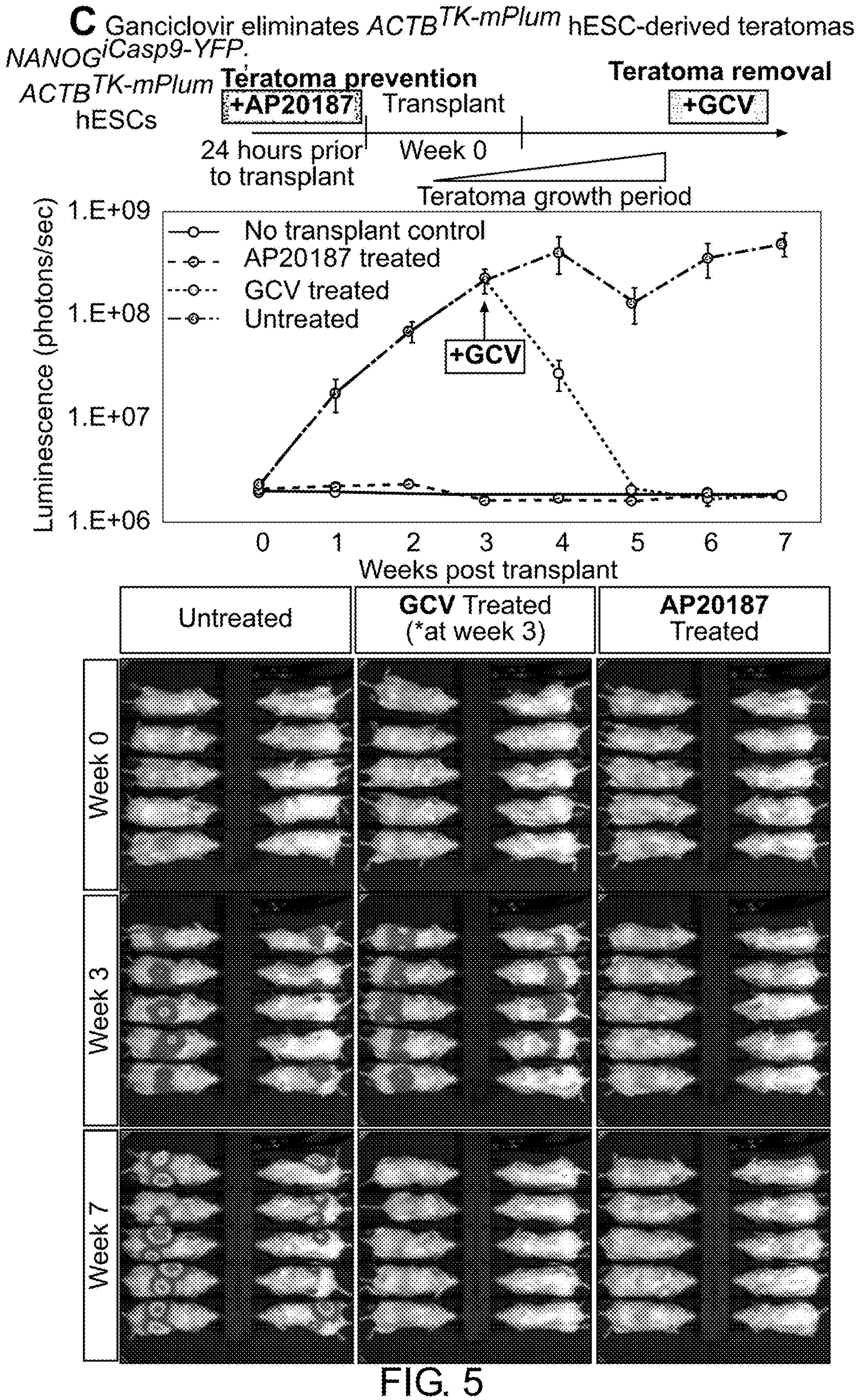

We found that ganciclovir treatment broadly blocked the in vitro proliferation of ACTB$^{HSV-TK-mPlum}$;NANOG$^{iCasp9-YFP}$ hPSCs (FIG. 5*a*) as well as their derivative liver, bone and forebrain progenitors (FIG. 5*b*). These results demonstrate that the ACTB$^{HSV-TK-mPlum}$ system can be used to inhibit the proliferation of undifferentiated hPSCs as well as those that have been differentiated into all three major germ layers (ectoderm, mesoderm, and endoderm).

We tested the ACTB$^{HSV-TK-mPlum}$ safeguard in an in vivo model in which growth of hPSC-derived tissues had to be eliminated (FIG. 5*c*). In this model system, we subcutaneously transplanted undifferentiated ACTB$^{HSV-TK-mPlum}$; NANOG$^{iCasp9-YFP}$ hPSCs, which formed teratomas within 3 weeks in NSG mice (FIG. 5*c*; FIG. 9*c*). Starting at 3 weeks post-transplantation, we treated transplanted mice with ganciclovir. This ablated any detectable teratomas as measured by bioluminescent imaging: by week 7 post-transplantation (i.e., 4 weeks after initiating ganciclovir administration), 10/10 of control mice harbored detectable teratomas, whereas no ganciclovir-treated mice had detectable teratomas (FIG. 5*c*; FIG. 9*c*).

Finally, we determined that the NANOG$^{iCasp9-YFP}$ and ACTB$^{HSV-TK-mPlum}$ systems were orthogonal, as they are activated by distinct, non-cross-reactive small molecules. To demonstrate this, we pre-treated the dual NANOG$^{iCasp9-YFP}$; ACTB$^{HSV-TK-mPlum}$ hPSCs with 1 nM AP20 before transplantation, which prevented them from forming teratomas in vivo (FIG. 5*c*). This thus demonstrates that the NANOG$^{iCasp9-YFP}$ system was still active in this genetically-engineered, dual safeguard pluripotent cell line.

In sum, this series of experiments demonstrate the power of the ACTB-TK$^{HSV}$-mPlum safety switch: in vivo treatment of ganciclovir can be used to eliminate any potential undesired hPSC-derived cell populations.

Figure 6:
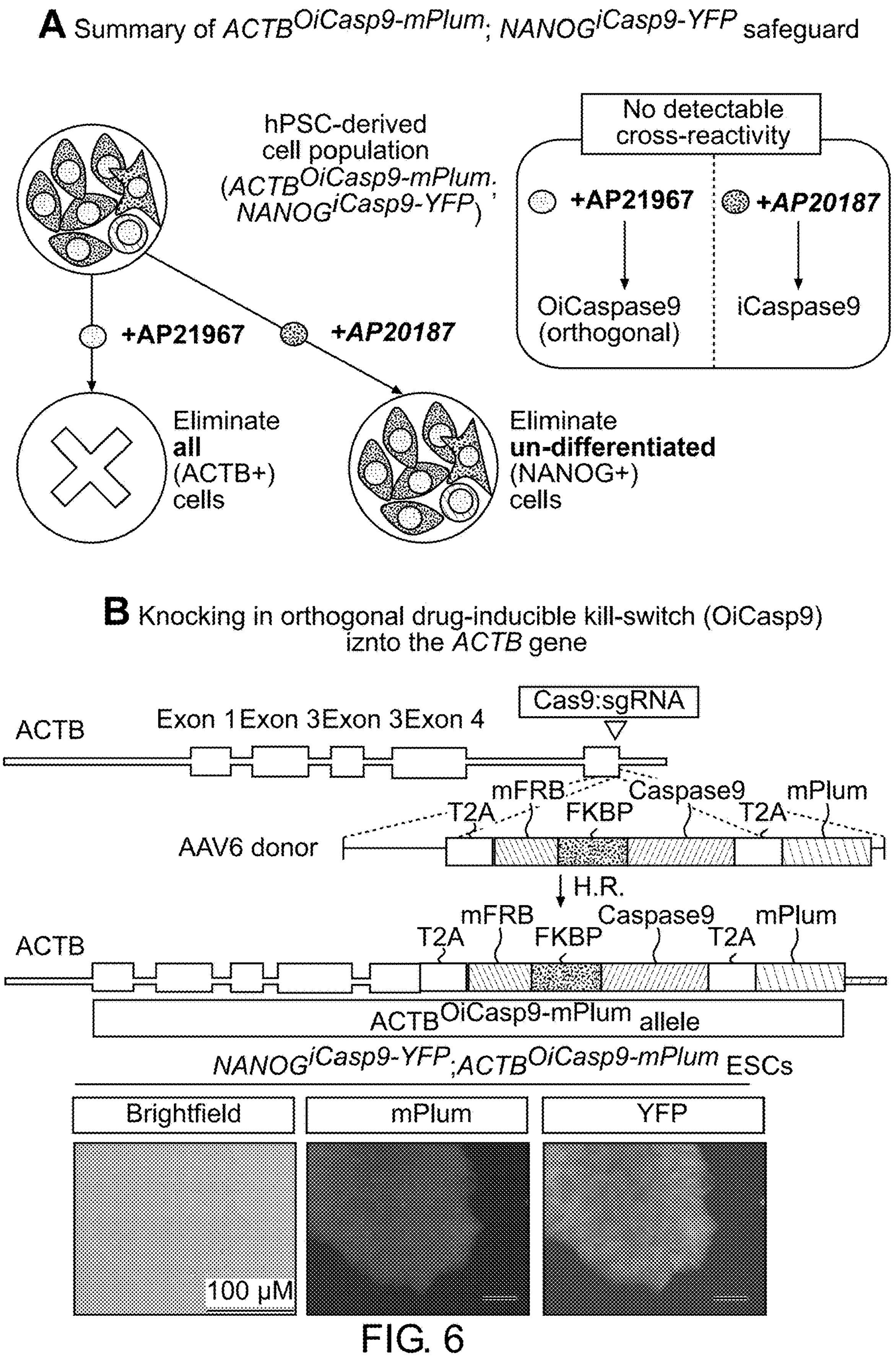
FIG. 6: Rationale, design and implementation of the ACTB$^{OiCasP9-mPlum}$ safety switch. A) Intended application of the dual ACTB$^{OiCasp9-mPlum}$;NANOG$^{iCasp9-YFP}$ safeguard. B) Cas9 RNP/AAV6-based knock-in strategy for ACTB$^{iCasp9-mPlum}$ targeting, which was performed in the NANOG$^{iCasp9-YFP}$ hESC line. C) $5\times10^5$ ACTB$^{OiCasp9-mPlum}$; NANOG$^{iCasp9-YFP}$ hESCs were treated with control media or 1-1000 nM AP21967 for 24 hours. Cell viability was analyzed using alamar blue. D) ACTB$^{OiCasp9-mPlum}$;NANOG$^{iCasp9-YFP}$ and ACTB$^{TK-mPlum}$; NANOG$^{iCasp9-YFP}$ hESCs (negative control), in addition to their respective differentiated derivatives, were treated for 24 hours with 1 nM of AP21967. E) $5\times10^5$ ACTB$^{OiCasp9-mPlum}$; NANOG$^{iCasp9-YFP}$ hESCs, and their respective differentiated derivatives, were treated with control media, 1 nM of AP21967 or and 1 nM of AP20187 for 24 hours. Surviving cells were analyzed by alamar blue. F) $10^6$ ACTB$^{OiCasp9-mPlum}$;NANOG$^{iCasp9-YFP}$ hESCs engineered to express CAG-AkaLuciferase were treated with control media or 1 nM AP20187 for 24 hours, and then subcutaneously transplanted into the right and left dorsal flanks of NOD-SCID Il2rg$^{-/-}$ mice ($10^6$ cells per flank). 4 weeks post-transplant, teratomas formed and AP21967 was intraperitoneally administered once at 10 mg/kg. Bioluminescent imaging of mice was conducted weekly for 8 weeks (with the exception of week 4, when imaging was performed again 3 days post-AP21967 administration). Total flux (photons/sec) was measured for each animal and was averaged.
Figure 6:
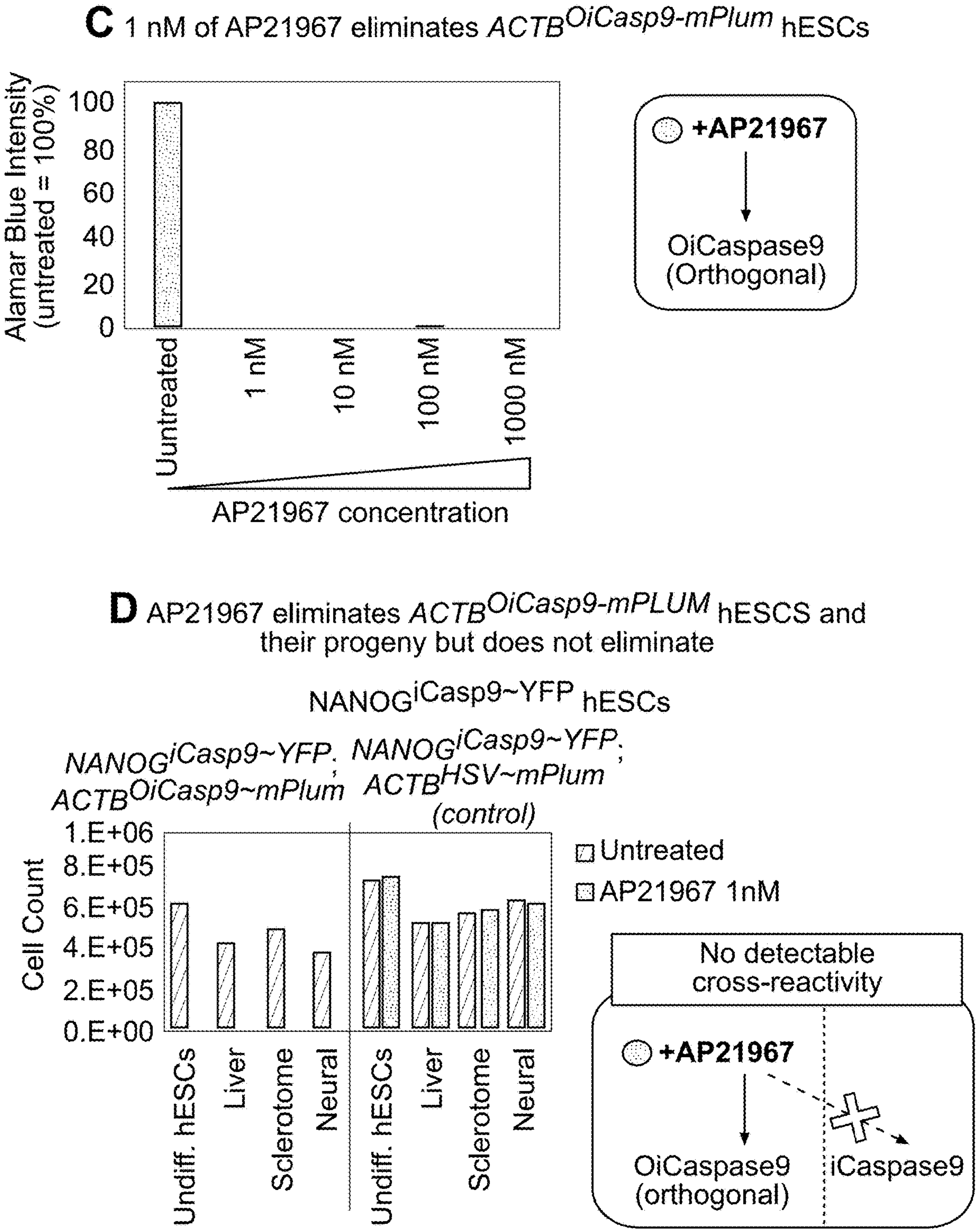
Figure 6:
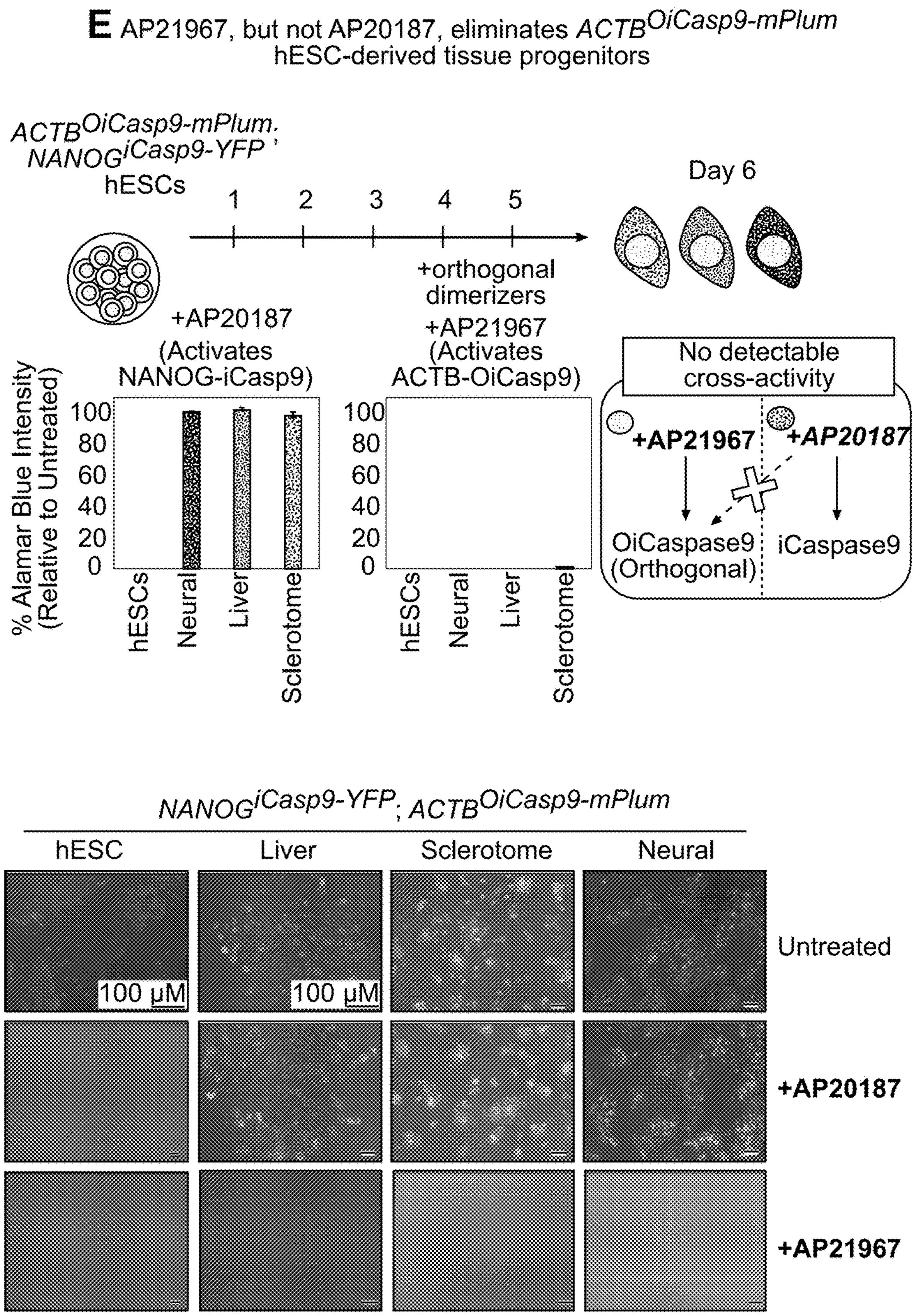
Figure 6:
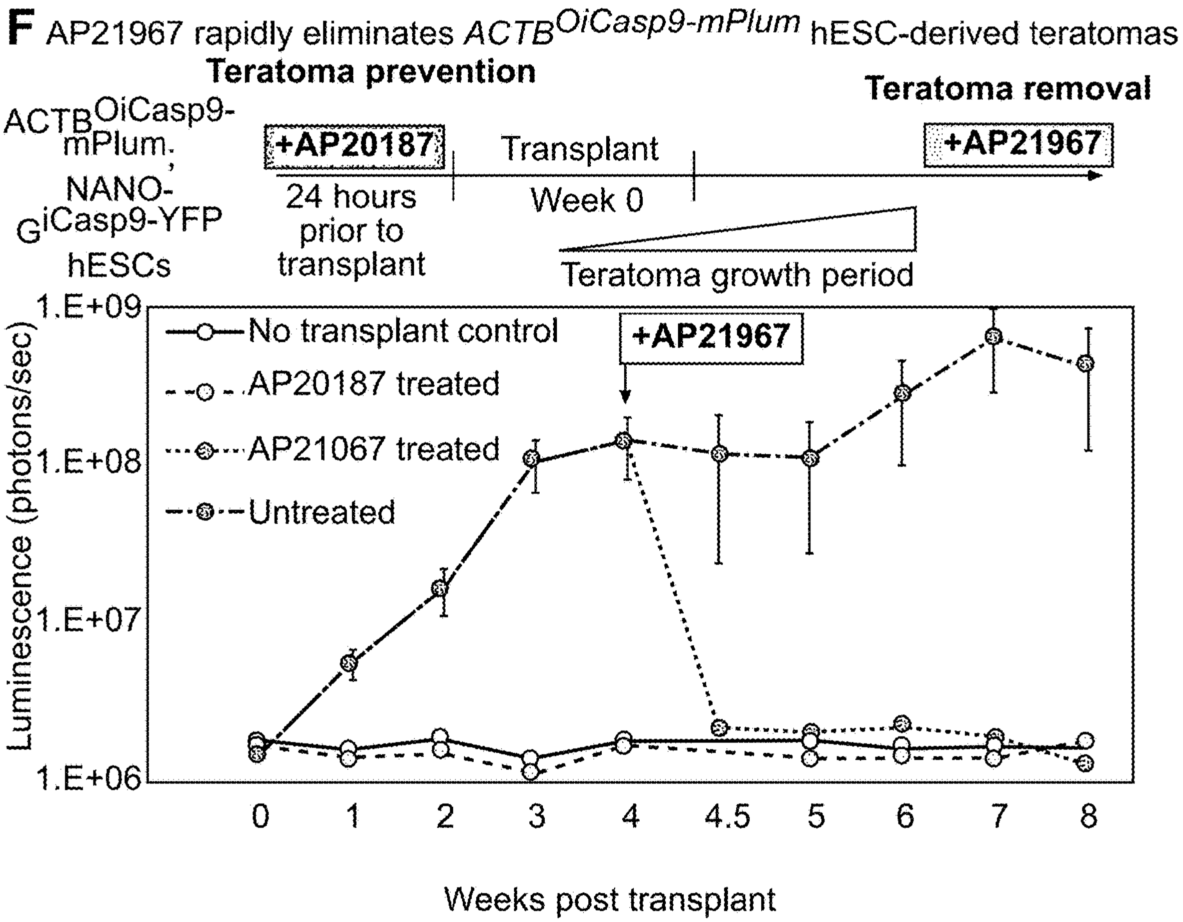
Figure 6:
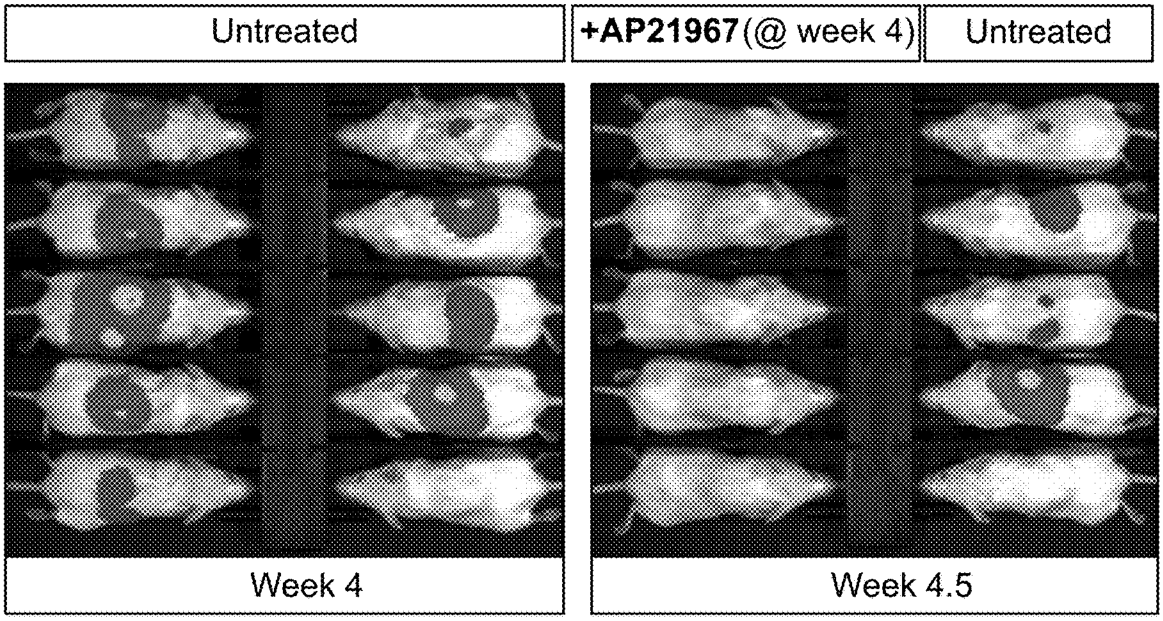

Engineering an orthogonal iCaspase9, thus creating an ACTB$^{OiCaspase9}$ system to directly kill all hPSC-derived cell-types. While TK$^{HSV}$ blocks cell proliferation and ablates teratomas in vivo (FIG. 2*f*; FIG. 9*c*), we developed a new tool to more directly kill all hPSC-derived cell-types in the event of an adverse event (as opposed to simply blocking their proliferation). We sought to create an orthogonal killing system that would be compatible with our NANOG$^{iCasp9-YFP}$ system (FIG. 1), which specifically eliminates undifferentiated hPSCs. While iCaspase9 dimerization is induced by AP20 (resulting in apoptosis), we engineered a new iCaspase9 that can activated by a second orthogonal small molecule that is not AP20 (FIG. 1; FIG. 6*a*).

This orthogonal iCaspase9 (henceforth, OiCaspase9) comprises Caspase9 fused to both a mutant FRB domain and a FKBP domain; these two domains are dimerized by a different small molecule (AP21967, hereafter called AP21) (FIG. 6*a*). To implement and test this new OiCaspase9 system, we knocked it into the ACTB gene in NANOG$^{iCasp9-YFP}$ hPSCs (FIG. 6*b*), thus generating ACTB$^{OiCasp9-mPlum}$;NANOG$^{iCasp9-YFP}$ hPSCs. In this dual-transgenic hPSC line, we could kill both undifferentiated hPSCs and differentiated liver, bone and neural progenitors (through treatment with AP21, which activates the ACTB$^{OiCasp9}$ kill-switch [FIG. 6*c-e*]), or alternatively, we could selectively kill undifferentiated hPSCs (through treatment with AP20, which activated the NANOG$^{iCasp9}$ kill-switch [FIG. 6*e*]). Importantly, we found that iCaspase9 and OiCaspase9 did not cross-react (FIG. 6e). Therefore, iCaspase9 and OiCaspase9 constitute orthogonal kill-switches, providing a toolkit for investigators to inducibly kill distinct cell subsets in different contingencies: for instance, 1) selectively eliminating undifferentiating hPSCs to reduce teratoma risk using AP20 or 2) killing all hPSC-derived cell-types using AP21, in the adverse event that transplanted cells proliferate uncontrollably or form unwanted tissues.

Improving the safety of hPSC-derived cell therapies is an important priority in order to make such therapies available to a broad range of patients for a range of indications, including those diseases (e.g., non-oncologic diseases) with current therapies that work but are not ideal, in which minimizing risk of a hPSC-derived therapy is essential. A less recognized but still important potential application of such safeguards is for "hypoimmunogenic" hPSC-based cell products that may not be adequately controlled by patients' immune systems in the event that transplanted cells become cancerous or infected. Here we report a general platform to improve the potential safety of hPSC-derived cell therapies, with the aim of mitigating two of the safety risks that beleaguer this otherwise-promising family of cell therapies.

The significance of the dual orthogonal systems is that it provides a method to deplete teratoma-forming cells from a therapeutic hPSC-derived cell product by greater than $10^6$ fold prior to infusion using the AP20 drug. This degree of purification would create a safety buffer for cell products of >1 billion cells or more to be infused without the toxicity of teratoma formation. Moreover, the second orthogonal safety switch (either $ACTB^{HSV\text{-}TK}$ or $ACTB^{OiCasp9}$) provides two different ways (GCV or AP21) to rapidly eliminate the cell product if needed. One might choose to eliminate the cell product because it either had led to adverse events or because it had served its therapeutic purpose and was no longer needed. The drugs used to activate the safety switches we describe are safely used in patients, providing for clinical translatability of these safety assurance systems.

While the dual orthogonal genome-edited hPSC lines we generated, either $ACTB^{HSV\text{-}TK\text{-}mPlum}$;$NANOG^{iCasp9\text{-}YFP}$ or $ACTB^{OiCasp9\text{-}mPlum}$;$NANOG^{iCasp9\text{-}YFP}$, are not suitable for clinical use because they contain foreign fluorescent protein markers and were not manufactured using Good Manufacturing Practice (GMP)-compliant practices, the systems are readily engineered into other hPSC lines with clinically relevant markers (such as truncated versions of NGFR, EGFR, CD19, or CD20) because the Cas9 RNP/AAV6 system we used to genetically engineer these lines is highly efficient and specific across a range of hPSC lines. Moreover, the RNP/AAV6 genome editing system is so efficient in hPSCs that selectable markers are not required to identify clones with bi-allelic integrations of both of these safeguard systems. While the use of dual safeguards address two important safety concerns for hPSC-derived cell therapies, cells can be engineered by genome editing using only of the systems as well, as they are independent of each other and utilize different genetic loci for their activity.

Finally, our safety systems are precisely knocked into endogenous loci within hPSCs (by contrast to past efforts to randomly insert them using lentiviral transgenes), thus reducing the risk of insertional mutagenesis or ectopic silencing of these safety systems. Avoiding transgene silencing should enhance the efficacy of the safeguard system, and avoiding insertional mutagenesis should provide additional safety to the genetically-engineered cell product.

Methods

Human pluripotent stem cell (hPSC) culture. hPSC culture and passaging was performed in line with WiCell's Feeder-Independent Protocols on Matrigel (Corning) or Geltrex (Gibco) coated plastic cell culture plates in mTeSR1 media (Stem Cell Technologies), with care to avoid any spontaneous differentiation. hPSCs were serially passaged as small clumps using an EDTA solution (Versene, Gibco) and remained karyotypically normal after genome engineering.

Preparing hPSCs for directed differentiation. hPSCs were grown to near confluency at which point they were dissociated into single cells or small clumps using Accutase (Gibco). Cells were seeded onto Matrigel or Geltrex coated 12-well plates at a density of approximately 25,000 cells/$cm^2$ in mTeSR1 supplemented with the ROCK inhibitor thiazovivin (1 μM, Tocris). The next day after seeding, cells were washed once with DMEM/F12 and subsequently, differentiation media was added. Differentiation media (media composition below) was changed every 24 hours. Whenever the new differentiation media composition was different from that of the previous day, the cells were briefly washed with DMEM/F12 (to remove any trace of the previous differentiation signals) before adding the new differentiation media.

Liver bud progenitor differentiation from hPSCs. hPSC differentiation into liver bud progenitors was performed as described previously (Ang et al., 2018) with the following media compositions on each day of differentiation:

- Day 1: CDM2 base media (Loh et al., 2014, Loh et al., 2016) supplemented with 100 ng/mL Activin A+3 μM CHIR99021+20 ng/mL FGF2+50 nM PI-103.
- Day 2: CDM2 base media supplemented with 100 ng/mL Activin A+250 nM LDN-193189+50 nM PI-103.
- Day 3: CDM3 base media (Ang et al., 2018) supplemented with 20 ng/mL FGF2+30 ng/mL BMP4+75 nM TTNPB+1 μM A-83-01.
- Day 4-6: CDM3 base media supplemented with 10 ng/mL Activin A+30 ng/mL BMP4+1 μM Forskolin.

Sclerotome progenitor differentiation from hPSCs. hPSC differentiation into sclerotome progenitors was performed as described previously (Loh et al., 2016) with the following media compositions on each day of differentiation:

- Day 1: CDM2 base media supplemented with 30 ng/mL Activin A+4 μM CHIR99021+20 ng/mL FGF2+100 nM PIK90.
- Day 2: CDM2 base media supplemented with 1 μM A83-01+250 nM LDN-193189+3 μM CHI R99021+20 ng/mL FGF2.
- Day 3: CDM2 base media supplemented with 1 μM A83-01+250 nM LDN-193189+1 μM XAV939+500 nM PD0325901.
- Day 4-6: CDM2 base media supplemented with 1 μM C59+5 nM SAG 21K.

Forebrain progenitor differentiation from hPSCs. hPSC differentiation into forebrain progenitors was performed as described previously (Maroof et al., 2013) with the following media composition for all 6 days of differentiation:

- Days 1-6: DMEM/F12 supplemented with 1% N2 (Gibco)+1% B27 without RA (Gibco)+1% GlutaMAX (Gibco)+500 nM LDN-193189+3 μM SB-431542+1 μM XAV939.

RNA extraction, reverse transcription and quantitative PCR. Undifferentiated or differentiated hPSCs were lysed in 350 μM of RLT Plus Buffer and RNA was extracted using the RNeasy Plus Mini Kit (Qiagen) according to the manufacturer's protocol. 300 ng of total RNA was reverse transcribed into cDNA for qPCR using the High-Capacity cDNA Reverse Transcription Kit (Applied Biosystems) according to the manufacturer's protocol. qPCR was performed in 384-well format as previously described (Loh et al., 2016) on a QuantStudio 5 qPCR machine (Thermo Fisher). Expression of all genes was first normalized to the levels of the reference gene YWHAZ, and then plotted relative to the levels of YWHAZ (i.e., 1.0=equivalent to YWHAZ). The following forward and reverse primer sequences were used to detect the expression of the respective genes:

TABLE 1

| Gene Name | Forward | Reverse |
|---|---|---|
| YWHAZ | (SEQ ID NO: 3) GAGCTGGTTCAGAAGGCCAAAC | (SEQ ID NO: 4) CCTTGCTCAGTTACAGACTTCATGCA |
| SOX2 | (SEQ ID NO: 5) TGGACAGTTACGCGCACAT | (SEQ ID NO: 6) CGAGTAGGACATGCTGTAGGT |
| OCT4 | (SEQ ID NO: 7) AGTGAGAGGCAACCTGGAGA | (SEQ ID NO: 8) ACACTCGGACCACATCCTTC |
| NANOG | (SEQ ID NO: 9) CATGAGTGTGGATCCAGCTTG | (SEQ ID NO: 10) CCTGAATAAGCAGATCCATGG |
| KLF4 | (SEQ ID NO: 11) AGCCTAAATGATGGTGCTTGGT | (SEQ ID NO: 12) CCTTGTCAAAGTATGCAGCAGT |
| CDK1 | (SEQ ID NO: 13) AAACTACAGGTCAAGTGGTAGCC | (SEQ ID NO: 14) TCCTGCATAAGCACATCCTGA |
| TERT | (SEQ ID NO: 15) AAA TGC GGC CCC TGT TTC T | (SEQ ID NO: 16) CAG TGC GTC TTG AGG AGC A |
| SCD1 | (SEQ ID NO: 17) TCTAGCTCCTATACCACCACCA | (SEQ ID NO: 18) TCGTCTCCAACTTATCTCCTCC |
| PODXL1 | (SEQ ID NO: 19) TCCCAGAATGCAACCCAGAC | (SEQ ID NO: 20) GGTGAGTCACTGGATACACCAA |
| SURVIVIN/ BIRC5 | (SEQ ID NO: 21) AGGACCACCGCATCTCTACAT | (SEQ ID NO: 22) AAGTCTGGCTCGTTCTCAGTG |
| BRACHYURY | (SEQ ID NO: 23) TGCTTCCCTGAGACCCAGTT | (SEQ ID NO: 24) GATCACTTCTTTCCTTTGCATCAA G |
| MIXL1 | (SEQ ID NO: 25) GGTACCCCGACATCCACTTG | (SEQ ID NO: 26) TAATCTCCGGCCTAGCCAAA |
| SOX17 | (SEQ ID NO: 27) CGCACGGAATTTGAACAGTA | (SEQ ID NO: 28) GGATCAGGGACCTGTCACAC |
| HNF4A | (SEQ ID NO: 29) TCA TGC AGG TGT GTG AGT CCA T | (SEQ ID NO: 30) AGT CAT TGC CTA GGA GCA GCA C |
| TBX3 | (SEQ ID NO: 31) TTA CCA AGT CGG GAA GGC GAA T | (SEQ ID NO: 32) CAT CCT CTT TGG CAT TTC GGG G |
| MSGN1 | (SEQ ID NO: 33) CGGAATTACCTGCCACCTGT | (SEQ ID NO: 34) GGTCTGTGAGTTCCCCGATG |
| TWIST1 | (SEQ ID NO: 35) CTGCAGCACCGGCACCGTTT | (SEQ ID NO: 36) CCCAACGGCTGGACGCACAC |
| SOX9 | (SEQ ID NO: 37) CGTCAACGGCTCCAGCAAGAAC AA | (SEQ ID NO: 38) GCCGCTTCTCGCTCTCGTTCAGA AGT |
| PAX1 | (SEQ ID NO: 39) CGCTATGGAGCAGACGTATGGC GA | (SEQ ID NO: 40) AATGCGCAAGCGGATGGCGTTG |
| PAX9 | (SEQ ID NO: 41) TGGTTATGTTGCTGGACATGGG TG | (SEQ ID NO: 42) GGAAGCCGTGACAGAATGACTAC CT |
| OTX2 | (SEQ ID NO: 43) GGAAGCACTGTTTGCCAAGACC | (SEQ ID NO: 44) CTGTTGTTGGCGGCACTTAGCT |
| PAX6 | (SEQ ID NO: 45) GCAGATGCAAAAGTCCAGGTG | (SEQ ID NO: 46) CAGGTTGCGAAGAACTCTGTTT |

TABLE 1-continued

| Gene Name | Forward | Reverse |
|---|---|---|
| FOXG1 | (SEQ ID NO: 47) CCG CAC CCG TCA ATG ACT T | (SEQ ID NO: 48 CCG TCG TAA AAC TTG GCA AAG |
| SIX3 | (SEQ ID NO: 49) CTGCCCACCCTCAACTTCTC | (SEQ ID NO: 50) GCAGGATCGACTCGTGTTTGT |
| LHX2 | (SEQ ID NO: 51) TCGGGACTTGGTTTATCACCT | (SEQ ID NO: 52) GCAAGCGGCAGTAGACCAG |
| iCASPASE9 | (SEQ ID NO: 53) CCAGATGAGTGTGGGTCAGA | (SEQ ID NO: 54) TGCTCAGGATGTAAGCCAAA |
| GAPDH | (SEQ ID NO: 55) GGAGCGAGATCCCTCCAAAAT | (SEQ ID NO: 56) GGCTGTTGTCATACTTCTCATGG |
| RPLPO | (SEQ ID NO: 57) AGCCCAGAACACTGGTCTC | (SEQ ID NO: 58) ACTCAGGATTTCAATGGTGCC |
| ACTB | (SEQ ID NO: 59) AGAGCTACGAGCTGCCTGAC | (SEQ ID NO: 60) AGCACTGTGTTGGCGTACAG |

Fluorescence activated cell sorting (FACS). Undifferentiated and differentiated hPSCs were dissociated by incubation in TrypLE Express (Gibco) for 5 minutes at 37° C. Subsequently, dissociated cells in TrypLE Express were diluted 1:10 in DMEM/F12 and centrifuged (pelleted) at 500 g for 5 minutes. Each cell pellet was resuspended in FACS buffer (PBS+1 mM EDTA [Invitrogen]+2% v/v FBS [Atlanta Bio]+1% Penicillin/Streptomycin [Gibco]) supplemented with the following antibodies, and antibody staining occurred for 30 minutes on ice protected from light, with antibodies used at the below concentrations:

TABLE 2

| Antibody | Fluorophore | Clone | Dilution | Catalog # |
|---|---|---|---|---|
| SSEA-3 | Alexa Flour 647 | MC-631 | 1:25 | BioLegend 330307 |
| SSEA-4 | Alexa Flour 647 | MC-813-70 | 1:25 | BioLegend 330407 |
| TRA-1-81 | APC | TRA-1-81 | 1:25 | Stem Cell Technologies 60065AZ.1 |
| TRA-1-60 | Alexa Flour 647 | TRA-1-60R | 1:25 | BioLegend 330605 |
| PODXL1 | APC | 222328 | 1:25 | R&D Systems FAB1658A |

After staining, cells were washed twice with FACS buffer and resuspended in 200 μL FACS buffer with DAPI (1:10,000, Biolegend) for live/dead discrimination. Samples were run on a Beckman Coulter CytoFlex analyzer (Stanford Stem Cell Institute FACS Core). For data analysis, cells were gated based on forward and side scatter with height and width used for doublet discrimination. Subsequently, live cells that were negative for DAPI were gated for all marker analyses and calculations of population frequency.

In vivo teratoma formation. 10 million NANOG$^{iCasp9\text{-}YFP}$ hPSCs were seeded in a Geltrex-coated 15-cm dish, in mTeSR1 supplemented with 1 μM thiazovivin (and, when applicable, 1 nM AP20187). 24 hours later, cells were then dissociated by treatment with TrypLE Express for 5 minutes at 37° C. Dissociated cells in TrypLE Express were diluted 1:10 in DMEM/F12, pelleted and resuspended in 1 mL of a 1:1 mixture of mTeSR1 and Matrigel per original 15-cm dish (approximately 10,000 cells/μL for untreated groups). Tubes were kept on ice until transplant. Immunodeficient NOD-SCID Il2rg$^{-/-}$ mice were used for all experiments. Mice were anesthetized during transplantation using isoflurane. 100 μL of cell suspension (~1 million cells) was injected subcutaneously into each of the right and left dorsal flanks of the mouse. Teratoma growth was monitored throughout the duration of the experiment via visual inspection and bioluminescent imaging.

Bioluminescent imaging. 20 minutes prior to imaging, mice were injected intraperitoneally with 100 μL of 15 mM AkaLumine HCl (Tokeoni, Aobious) dissolved in $H_2O$. Mice were anesthetized using isoflurane and placed in the imaging chamber of either an IVIS Spectrum or SII Lago-X bioluminescent imaging machine. Imaging parameters were kept constant throughout the duration of each experiment with no images reaching saturation (Binning=4, FStop=1.2, Exposure time=10 seconds). Subsequent image analysis was done in Aura with regions of interest (ROIs) drawn for each mouse to calculate Total Flux (photons/sec) in order to quantify teratoma growth over time.

Regulatory and institutional review. All animal experiments were conducted according to experimental protocols approved by the Stanford Administrative Panel on Laboratory Animal Care (APLAC). All human pluripotent stem cell experiments were conducted in accord with experimental protocols approved by the Stanford Stem Cell Research Oversight (SCRO) committee.

Quantification of cell death in vitro. To quantify cell death after AP20187 treatment of undifferentiated or differentiated hPSCs, we used multiple independent assays:

Clonal assay for surviving hPSC colonies—hPSCs were dissociated into single cells with Accutase (Thermo Fisher) and $1\times10^6$ cells were plated per well of a 6-well plate that was pre-coated with Matrigel. To enhance single-cell survival, hPSCs were plated in mTeSR1 supplemented with ROCK inhibitor 10 μM Y-27632 for 1 hour (in the presence or absence of AP20187 at the indicated concentrations). ROCK inhibitor was then withdrawn for the remaining 23 hours of culture; that is, hPSCs were cultured in mTeSR1 (in the presence or absence of AP20187). Subsequently, AP20187 was withdrawn altogether and hPSCs were cultured with mTeSR1 for 1 week, to allow any surviving hPSCs to regrow and to form clonal colonies, which were then scored (i.e., 1 surviving colony after AP20187 treatment of $1\times10^6$ hPSCs indicated survival of 1 out of $10^6$ cells).

Cell count assay—hESCs were dissociated with EDTA and $5\times10^5$ cells were plated per well of a 6-well plate that was pre-coated with Matrigel. Cells were seeded in mTeSR1+ROCK inhibitor 10 μM Y-27632 (in the presence or absence of AP20187 at the indicated concentrations) for 24 hours. Subsequently, cells were dissociated and the number of viable cells were counted using the Bio-Rad TC20™ Automated Cell Counter (trypan blue exclusion).

Alamar Blue proliferation assay—hESCs were cultured in mTeSR1 (in the presence or absence of AP20187 at the indicated concentrations). After 24 hours of AP20187 treatment, mTeSR1 media with Alamar Blue (concentration based on manufacturer's protocol) was changed for both untreated and treated samples. A control well containing media+Alamar Blue was used to assess blank wells and to therefore to measure and subtract fluorescence noise.

Flow cytometric quantification of viable cells—NANOG$^{iCasp9\text{-}YFP}$ hESCs were dissociated into single cells with Accutase and $1\times10^6$ cells were plated per well in a 6-well plate pre-coated with Matrigel. To enhance single-cell survival, hPSCs were plated in mTeSR1 supplemented with ROCK inhibitor 10 μM Y-27632 for 1 hour (in the presence or absence of AP20187 at the indicated concentrations). ROCK inhibitor was then withdrawn for the remaining 23 hours of culture; that is, hPSCs were cultured in mTeSR1 (in the presence or absence of AP20187). Subsequently, to quantify the percentage of surviving cells, the cultures were dissociated with TrypLE Express. Cells in TrypLE Express were diluted 1:10 in DMEM/F12 and centrifuged (pelleted) at 500 g for 5 minutes. Each cell pellet was resuspended in FACS buffer (PBS+1 mM EDTA [Invitrogen]+2% v/v FBS [Atlanta Bio]+1% Penicillin/Streptomycin [Gibco]) supplemented with DAPI (1:10,000, Biolegend) to discriminate live vs. dead cells. YFP$^+$ (i.e., NANOG$^+$) cells were analyzed (Beckman Coulter CytoFlex Analyzer) to count live cells for both untreated and AP20187-treated groups. In some experiments, YFP$^+$ (i.e., NANOG$^+$) cells were sorted (BD FACS Aria II) and cultured in mTeSR1 to test whether they were actually still living and could form hPSC colonies.

Quantification of cell death after ganciclovir treatment. NANOG$^{iCasp9\text{-}YFP}$;ACTB-TK$^{HSV}$-mPlum hPSCs ($5\times10^5$ cells) were plated and treated with ganciclovir (GCV) at varying concentrations (0.5-2 μM) for 24 hours in mTeSR1; subsequently, GCV was withdrawn and hPSCs were cultured in mTeSR1 alone for 6 further days. Three days post-GCV treatment, cell death was observed in hPSCs. At the end of 6 days of culture in mTeSR1 alone, the number of surviving live cells was counted.

Ablation of undifferentiated hPSCs in a heterogeneous cell population. To assess whether AP20187 could kill undifferentiated hPSCs within a heterogeneous cell population, we simulated a cell-therapy manufacturing error; to that end undifferentiated hPSCs were deliberately spiked into a differentiated cell population. Specifically, $1\times10^6$ NANOG$^{iCasp9\text{-}YFP}$ hPSCs were dissociated with Accutase and mixed with $1\times10^5$ NANOG$^{iCasp9\text{-}YFP}$ hPSC-derived day 5 sclerotome cells. This mixed cell population was seeded in sclerotome media (CDM2 base media+1 μM C59+5 nM SAG 21K [described above])+100 ng/mL FGF2 (to help undifferentiated hPSCs survive)+10 μM Y-27632 (to help single, dissociated hPSCs adhere and survive), in the presence or absence of 1 nM AP20187 for 1 hour. For the remaining 23 hours, ROCK inhibitor was removed; that is, the heterogeneous cell populations were cultured in sclerotome media+100 ng/mL FGF2 in the presence or absence of AP20187.

Construction of Safety Switches. Genetic cassettes encoding the respective safety switches and flanking homology arms for homologous recombination (NANOG-iCasp9-YFP and ACTB-TK$^{HSV}$-mPlum) were cloned into the pAAV-MCS plasmid (Agilent Technologies) containing AAV2 ITRs. Both vectors were designed to replace the stop codon of each respective gene (NANOG or ACTB) and to insert each respective safety switch immediately downstream of the coding sequence of each gene, in lieu of the stop codon.

AAV6 Cloning and Production. For AAV production, safety switch plasmids were cloned using NEBuilder® HiFi DNA Assembly Cloning Kit. Plasmids were grown in *E. coli* (NEB® Stable Comptent *E. Coli* (Cat #03040I) and produced using Invitrogen's Endotoxin-Free Maxi Plasmid Purification Kit (Cat #A33073). Following DNA purification, 50 million 293FT cells (Life Technologies) were plated in 15 cm$^2$ dishes. The cells were transfected the next day using 120 μL (1 mg/mL) of PEI (MW 25K) (Polysciences), 6 μg of donor plasmid, and 22 μg pDGM6 (which carried AAV6 cap, AAV2 rep, and adenoviral helper genes) (gift from D. Russell). 72 hours post-transfection, cells were harvested and purified using the Takara AAVpro Purification Kit (Cat. 6666) according to the manufacturer's protocol. AAV6 vector titer was determined using ddPCR to measure vector genome concentration.

Alkaline phosphatase staining. Alkaline phosphatase staining was done using the Alkaline Phosphatase Staining Kit (Red) (ab242286) using the manufacturer's protocol. In brief, hPSCs were washed with PBS, fixed, and stained for 20 minutes using the alkaline phosphatase kit.

Imaging. Fluorescent images were taken using the BZ-X710 All-in-One Fluorescence Microscope (Keyence) or the EVOS FL cell imaging system (Thermo Fisher).

AAV6/Cas9 genome editing of hPSCs. H9 hPSCs were used throughout this study, and were genetically engineered as described previously (Martin et al., 2019). In brief, H9 hPSCs were treated with 10 μM ROCK inhibitor (Y-27632) 24 hours prior to editing. Cells at 70-80% confluence were dissociated using Accutase (Life Technologies) followed by neutralization with ROCK inhibitor-supplemented mTeSR1 media. Prior to electroporation, RNP complex was formed by combining 5 μg of HiFi Cas9 (Integrated DNA Technologies) and 1.75 μg of sgRNA for 10 minutes at room temperature, which was then diluted with 20 μL of P3 Primary Cell solution (Lonza). For each reaction, 500,000 cells were mixed with the nucleofection solution containing Cas9/sgRNA RNP. Nucleofection was performed using 16-well Nucleocuvette Strip with 4D Nucleofector system (Lonza) using the CA137 electroporation code. Following electroporation, cells were transferred into one well of a Matrigel-coated 24-well plate containing 500 μL of mTeSR1 media supplemented with 10 μM Y-27632. AAV6 donor vector was added at 100K MOI directly to cells after plating in a 24 well coated with Matrigel. Cells were then incubated at 37° C. for 24 hours. Media was changed 24 hours post-editing and 10 μm Y-27632 was removed 48 hours after.

The NANOG and ACTB synthetic sgRNAs were purchased from Synthego with chemically-modified nucleotides at the three terminal positions at both the 5' and 3' ends. Modified nucleotides contained 2'-O-methyl 3'-phosphorothioate. The genomic sgRNA target sequences, with the PAM sequence in bold, were:

NANOG:

(SEQ ID NO: 61)
5'-ACTCATCTTCACACGTCTTCAGG-3'

ACTB:

(SEQ ID NO: 62)
5'-CCGCCTAGAAGCATTTGCGGCGG-3'.

Generation of AkaLuc-expressing hPSCs. PiggyBac donor plasmid (pPB_CAG_AkaLuc_Puro) was constructed by using pPB_CAG_rtTAM2_IN and replacing rtTAM2_IN with AkaLuc and Puro, using In-Fusion® HD Cloning Plus.

Karyotype Analysis. Karyotype analysis was performed by the Cytogenetics lab at Stanford University. Cells were growing in T25 flasks on Matrigel and harvested for analysis. Chromosomes were analyzed using the GTW banding method. Twenty metaphase cells were analyzed, all of which were concluded to have a normal karyotype (46, XY).

Immunofluorescence. hPSCs or their differentiated progeny were fixed in 4% paraformaldehyde for 15 minutes; permeabilized in 0.2% Triton X-100 in PBS; and then blocked with blocking buffer (0.1% Triton-X and 2% FBS in PBS). For primary staining, anti-NANOG (RRID: AB_10559205), anti-SOX2 (RRID: AB_2195767), and anti-TWIST1 (RRID: AB_883292) antibodies were diluted 200-fold with blocking buffer and stained at 4° C. overnight. Cells were then washed three times and then secondary staining was performed with 1:500 diluted Cy5 Donkey Anti-Rabbit IgG (RRID: AB_2340607) for 1 hour. Cells were washed again and DAPI (RRID: AB_2629482) staining was used on the third wash.

For live staining, cells were treated with 5 μg/mL of Hoescht (Invitrogen™ Cat #H3569) for 30 minutes, washed with PBS, and then imaged using the EVOS FL cell imaging system.

TABLE 3

| Antibody | Dilution | Catalog # |
|---|---|---|
| Anti-human TWIST1 | 1:200 | RRID: AB_883292 |
| Anti-human NANOG | 1:200 | RRID: AB_10559205 |
| Anti-human SOX2 | 1:200 | RRID: AB_2195767 |
| Cy ™5 AffiniPure Donkey Anti-Rabbit IgG (H + L) | 1:500 | RRID: AB_2340607 |
| DAPI | 1:5000 | RRID: AB_2629482 |
| Hoescht live stain | 1:2000 | Invitrogen ™ Cat# H3569 |

Genotyping and Sequence Analysis. To confirm successful genetic targeting of the NANOG and ACTB loci, genomic DNA was isolated from NANOG$^{iCasp9\text{-}YFP}$;ACTB-TK$^{HSV}$-mPlum hPSCs using QuickExtract DNA Extraction Solution (Epicentre) following the manufacturer's instructions. Then, genomic PCR was performed using Phusion Green HSII Master Mix (Thermo Fisher) and the primer sequences listed below. For DNA sequencing of the targeted alleles, PCR amplicons were gel-extracted and submitted for Sanger sequencing through MCLab (South San Francisco, CA, USA). Off-target editing events were predicted for each sgRNA by COSMID46 tool. Based on these predictions, we identified NANOGP8 as a possible "off-target" locus and analyzed this possibility using primers detailed in the table below:

TABLE 4

| Primer | Sequence | Notes | Gene Amplified |
|---|---|---|---|
| FW1 | (SEQ ID NO: 63) CCACCATTATAGATCTCT | NANOG specific | NANOG |
| REV1 | (SEQ ID NO: 64) TGTCATTACGATGCAGCAAA | NANOG specific | NANOG |
| FW2 | (SEQ ID NO: 65) AGTTCATGCGCTTCAAGGAG | Binds to mPlum | ACTB |
| REV2 | (SEQ ID NO: 66) TGAATGGGGGTTGAATGATTA | ACTB specific | ACTB |
| FW3 | (SEQ ID NO: 67) CTCAGATCATTGCTCCTCC | ACTB specific | ACTB |
| REV3 | (SEQ ID NO: 68) AGAAGTGGGGTGGCTTTTAG | ACTB specific | ACTB |
| FW4 | (SEQ ID NO: 69) GCACATCTTGCCAGGATTTTA | NANOGP8 specific | NANOGP8 |
| REV4 | (SEQ ID NO: 70) TCCTATGAAGGATGGGAGGA | NANOGP8 specific | NANOGP8 |

Design of Orthogonal Safety Switches. NANOG-iCasp9-YFP: Encodes iCasp9 (Caspase9-FKBP$^{F36V}$) linked to the end of the endogenous NANOG gene. Insertion was made by removing the stop codon of NANOG and inserting Sequence 1 (below). NANOG-iCasp9 is activated by the small molecule AP20187.

Genome editing. hPSCs were propagated in mTeSR1 (StemCell Technologies)+1% penicillin/streptomycin (Gibco). Genome editing was performed as previously described by Martin et al. Cell Stem Cell 24, 821-828.e825. In brief, hPSCs were electroporated with ribonucleoprotein complexes carrying an engineered, high-specificity HiFi Cas9 variant complexed with chemically-modified sgRNAs together with AAV6 vectors carrying templates for homologous recombination. The genomic sgRNA target sequences with PAM in bold are (SEQ ID NO:1) NANOG: 5'-ACTCATCTTCACACGTCTTCAGG-3' and (SEQ ID NO:2) ACTB: 5'-CCGCCTAGAAGCATTTGCGGTGG-3'. Single hPSCs were expanded as clonal lines for genomic sequencing to confirm successful knock-ins.

hPSC differentiation. hPSCs were sequentially differentiated towards 1) anterior most primitive streak, definitive endoderm, and liver bud progenitors; or 2) anterior primitive streak, paraxial mesoderm and sclerotome (bone) progenitors; or 3) ectoderm, neural ectoderm and forebrain progenitors as previously described, all in defined and feeder-free conditions.

Specific and rapid elimination of hPSCs using AP20187. NANOG-2A-iCasp9 hPSCs or their differentiated progeny were treated with AP20187 (1 nM, or other doses as indicated) for 24 hours to deplete pluripotent cells.

Elimination of teratomas using Ganciclovir in vivo. After transplantation into adult NSG mice, ACTB-2A-$^{HSV}$TK hPSCs or their differentiated progeny were treated with ganciclovir (50 mg/kg) daily for 4 weeks. Experimental details are provided in the Supplementary Methods.

REFERENCES

Guhr, A. et al. Recent Trends in Research with Human Pluripotent Stem Cells: Impact of Research and Use of Cell Lines in Experimental Research and Clinical Trials. Stem Cell Reports 11, 485-496, doi:10.1016/j.stemcr.2018.06.012 (2018).

Wang, X. et al. Cloning and variation of ground state intestinal stem cells. Nature 522, 173-178, doi:10.1038/nature14484 (2015).

McKnight, K., Wang, P. & Kim, S. K. Deconstructing pancreas development to reconstruct human islets from pluripotent stem cells. Cell Stem Cell 6, 300-308 (2010).

Lee, A. S. et al. Effects of cell number on teratoma formation by human embryonic stem cells. Cell Cycle 8, 2608-2612 (2009).

Haridass, D. et al. Repopulation Efficiencies of Adult Hepatocytes, Fetal Liver Progenitor Cells, and Embryonic Stem Cell-Derived Hepatic Cells in Albumin-Promoter-Enhancer Urokinase-Type Plasminogen Activator Mice. The American Journal of Pathology 175, 1483-1492, doi:10.2353/ajpath.2009.090117 (2010).

Kroon, E. et al. Pancreatic endoderm derived from human embryonic stem cells generates glucose-responsive insulin-secreting cells in vivo. Nat Biotechnol 26, 443-452 (2008).

Rezania, A. et al. Maturation of human embryonic stem cell-derived pancreatic progenitors into functional islets capable of treating pre-existing diabetes in mice. Diabetes (2012).

Rostovskaya, M., Bredenkamp, N. & Smith, A. Towards consistent generation of pancreatic lineage progenitors from human pluripotent stem cells. Philosophical transactions of the Royal Society of London. Series B, Biological sciences 370, 20140365, doi:10.1098/rstb.2014.0365 (2015).

Ganat, Y. M. et al. Identification of embryonic stem cell-derived midbrain dopaminergic neurons for engraftment. Journal of Clinical Investigation 122, 2928-2939, doi:10.1172/JCI58767 (2012).

Manley, N. C., Priest, C. A., Denham, J., Wirth, E. D. & Lebkowski, J. S. Human Embryonic Stem Cell-Derived Oligodendrocyte Progenitor Cells: Preclinical Efficacy and Safety in Cervical Spinal Cord Injury. Stem Cells Translational Medicine 6, 1917-1929, doi:10.1002/sctm.17-0065 (2017).

Han, X. et al. Generation of hypoimmunogenic human pluripotent stem cells. Proceedings of the National Academy of Sciences of the United States of America 2014, 201902566, doi:10.1073/pnas.1902566116 (2019).

Deuse, T. et al. Hypoimmunogenic derivatives of induced pluripotent stem cells evade immune rejection in fully immunocompetent allogeneic recipients. Nature Biotechnology 116, 1346, doi:10.1038/s41587-019-0016-3 (2019).

Draper, J. S., Pigott, C., Thomson, J. A. & Andrews, P. W. Surface antigens of human embryonic stem cells: changes upon differentiation in culture*. Journal of anatomy 200, 249-258, doi:10.1046/j.1469-7580.2002.00030.x (2002).

Choo, A. B. et al. Selection against undifferentiated human embryonic stem cells by a cytotoxic antibody recognizing podocalyxin-like protein-1. Stem Cells 26, 1454-1463, doi:10.1634/stemcells.2007-0576 (2008).

Liang, Q. et al. Linking a cell-division gene and a suicide gene to define and improve cell therapy safety. Nature 563, 701-704, doi:10.1038/s41586-018-0733-7 (2018).

Qadir, M. M. F. et al. A Double Fail-Safe Approach to Prevent Tumorigenesis and Select Pancreatic β Cells from Human Embryonic Stem Cells. Stem Cell Reports, 1-26, doi:10.1016/j.stemcr.2019.01.012 (2019).

Ben-David, U. et al. Selective elimination of human pluripotent stem cells by an oleate synthesis inhibitor discovered in a high-throughput screen. Cell Stem Cell 12, 167-179, doi:10.1016/j.stem.2012.11.015 (2013).

Bedel, A. et al. Preventing Pluripotent Cell Teratoma in Regenerative Medicine Applied to Hematology Disorders. Stem Cells Translational Medicine 6, 382-393, doi:10.5966/sctm.2016-0201 (2017).

Lee, M.-O. et al. Inhibition of pluripotent stem cell-derived teratoma formation by small molecules. Proceedings of the National Academy of Sciences of the United States of America 110, E3281-3290, doi:10.1073/pnas.1303669110 (2013).

Loh, K. M. et al. Efficient Endoderm Induction from Human Pluripotent Stem Cells by Logically Directing Signals Controlling Lineage Bifurcations. Cell Stem Cell 14, 237-252 (2014).

Ang, L. et al. A roadmap for human liver differentiation from pluripotent stem cells. Cell Reports 22, 2190-2205 (2018).

Loh, K. M. et al. Mapping the Pairwise Choices Leading from Pluripotency to Human Bone, Heart, and Other Mesoderm Cell Types. Cell 166, 451-467, doi:10.1016/j.cell.2016.06.011 (2016).

Maroof, A. M. et al. Directed differentiation and functional maturation of cortical interneurons from human embryonic stem cells. Cell Stem Cell 12, 559-572, doi:10.1016/j.stem.2013.04.008 (2013).

Loh, K. M. & Lim, B. A precarious balance: pluripotency factors as lineage specifiers. Cell Stem Cell 8, 363-369 (2011).

Martin, R. M. et al. Highly Efficient and Marker-free Genome Editing of Human Pluripotent Stem Cells by CRISPR-Cas9 RNP and AAV6 Donor-Mediated Homologous Recombination. Cell Stem Cell 24, 821-828.e825, doi:10.1016/j.stem.2019.04.001 (2019).

Straathof, K. C. et al. An inducible caspase 9 safety switch for T-cell therapy. Blood 105, 4247-4254, doi:10.1182/blood-2004-11-4564 (2005).

Wang, Z., Oron, E., Nelson, B., Razis, S. & Ivanova, N. Distinct lineage specification roles for NANOG, OCT4, and SOX2 in human embryonic stem cells. Cell Stem Cell 10, 440-454 (2012).

Miyanari, Y. & Torres-Padilla, M.-E. Control of ground-state pluripotency by allelic regulation of Nanog. Nature, 1-6, doi:10.1038/nature10807 (2012).

Iwano, S. et al. Single-cell bioluminescence imaging of deep tissue in freely moving animals. Science 359, 935-939, doi:10.1126/science.aaq1067 (2018).

Fillat, C., Carrió, M., Cascante, A. & Sangro, B. Suicide gene therapy mediated by the Herpes Simplex virus thymidine kinase gene/Ganciclovir system: fifteen years of application. Current gene therapy 3, 13-26 (2003).

Shawlot, W., Deng, J. M., Fohn, L. E. & Behringer, R. R. Restricted beta-galactosidase expression of a hygromycin-lacZ gene targeted to the beta-actin locus and embryonic lethality of beta-actin mutant mice. Transgenic research 7, 95-103, doi:10.1023/a:1008816308171 (1998).

Itakura, G. et al. Fail-Safe System against Potential Tumorigenicity after Transplantation of iPSC Derivatives. Stem Cell Reports, doi:10.1016/j.stemcr.2017.02.003 (2017).

Ando, M. et al. A Safeguard System for Induced Pluripotent Stem Cell-Derived Rejuvenated T Cell Therapy. Stem Cell Reports, doi:10.1016/j.stemcr.2015.07.011 (2015).

Bayle, J. H. et al. Rapamycin analogs with differential binding specificity permit orthogonal control of protein activity. Chemistry & Biology 13, 99-107, doi:10.1016/j.chembiol.2005.10.017 (2006).

Di Stasi, A. et al. Inducible apoptosis as a safety switch for adoptive cell therapy. New England Journal of Medicine 365, 1673-1683, doi:10.1056/NEJMoa1106152 (2011).

Takashima, Y. et al. Resetting transcription factor control circuitry toward ground-state pluripotency in human. Cell 158, 1254-1269, doi:10.1016/j.cell.2014.08.029 (2014).

What is claimed is:

1. A genetically engineered cell comprising:

a first safety switch integrated in-frame at a first target locus in the genome where it is operably linked to the promoter of a first gene of interest without disrupting expression of the gene of interest, which gene of interest is selectively expressed in pluripotent cells, wherein the gene of interest is NANOG; and wherein the safety switch encodes an inducible caspase protein lacking native caspase activation domain and fused to a dimerization domain of FKBP or FRB, that is activated by a first orthologous activating agent;

wherein the cell further comprises a second safety switch which is integrated at a second target locus in the genome where it is operably linked to the promoter of a second gene of interest without disrupting expression of the second gene of interest, which second gene of interest is ubiquitously expressed and required for cell viability;

wherein the second safety switch encodes a switch protein that is activated by a second orthologous activating agent and is not activated by the first orthologous activating agent, and wherein the first safety switch when activated causes a greater than $10^6$-fold killing of pluripotent cells in vitro.

2. The genetically engineered cell of claim 1, wherein the second gene of interest encodes a cytoskeletal protein, optionally beta actin (ACTB).

3. The genetically engineered cell of claim 1, wherein the second safety switch is integrated to replace the stop codon of the second gene of interest, and/or the second switch protein is flanked by self-cleaving peptide sequences.

4. The genetically engineered cell of claim 1, wherein the inducible caspase protein is Δ caspase 9.

5. The genetically engineered cell of claim 1, wherein the inducible caspase protein is fused to a dimerization domain of FKBP and FRB, optionally an F36V mutant of human FKBP domain ($FKBP^{F36V}$).

6. The genetically engineered cell of claim 1, wherein the second safety switch encodes a herpesvirus thymidine kinase.

7. A genetically engineered cell comprising:

(i) a first safety switch integrated at NANOG locus in the genome where it is operably linked to the promoter of NANOG without disrupting expression of NANOG, wherein the safety switch encodes an inducible caspase protein lacking native caspase activation domain and fused to $FKBP^{F36V}$, activated by a first orthologous activating agent and wherein the safety switch when activated causes a greater than $10^6$-fold killing of pluripotent cells in vitro; and (ii) a second safety switch integrated at a second target locus in the genome where it is operably linked to the promoter of a second gene of interest without disrupting expression of the second gene of interest, which second gene of interest is ubiquitously expressed and required for cell viability; wherein the second safety switch encodes a viral thymidine kinase protein that is activated by a second orthologous activating agent and is not activated by the first orthologous activating agent.

* * * * *